(12) United States Patent
Gerona-Navarro et al.

(10) Patent No.: US 11,345,725 B2
(45) Date of Patent: May 31, 2022

(54) BIS-THIOETHER STAPLED PEPTIDES AS INHIBITORS OF PRC2 FUNCTION

(71) Applicant: Research Foundation of the City University of New York, New York, NY (US)

(72) Inventors: Guillermo Gerona-Navarro, New York, NY (US); Gan Zhang, Brooklyn, NY (US); Flavia Barragan, Berlin (DE)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 17/022,900

(22) Filed: Sep. 16, 2020

(65) Prior Publication Data

US 2021/0079044 A1     Mar. 18, 2021

Related U.S. Application Data

(60) Provisional application No. 62/900,964, filed on Sep. 16, 2019.

(51) Int. Cl.
    *C07K 7/08*     (2006.01)

(52) U.S. Cl.
    CPC ..................... *C07K 7/08* (2013.01)

(58) Field of Classification Search
    None
    See application file for complete search history.

(56) References Cited

U.S. PATENT DOCUMENTS

| 5,811,515 A | 9/1998 | Grubbs et al. |
| 7,960,506 B2 | 6/2011 | Nash |
| 8,586,707 B2 | 11/2013 | Lin et al. |
| 2015/0376579 A1 | 12/2015 | Smith, III et al. |

FOREIGN PATENT DOCUMENTS

| WO | WO2008121767 | 10/2008 |
| WO | WO2011008260 | 1/2011 |
| WO | WO2012174423 | 12/2012 |
| WO | WO2013150338 | 10/2013 |
| WO | WO2013179143 | 12/2013 |
| WO | WO2014149001 | 9/2014 |
| WO | WO2014201370 | 12/2014 |
| WO | WO2016209978 | 12/2016 |
| WO | WO2017092691 | 6/2017 |
| WO | WO2017147283 | 8/2017 |

OTHER PUBLICATIONS

Rai et al. ('Elements of the polycomb repressor SU(Z)12 needed for histone H3-K27 methylation, the interface with E(Z), and in vivo function' Molecular and Cellular Biology v33(24) Dec. 2013) pp. 4844-4856) (Year: 2013).*

Zhang supplement (Supporting information for A solid-phase approach to accessing bisthioether-stapled peptides resulting in a potent inhibitor of PRC2 catalytic activity Angew Chem Int Ed Engl Nov. 26, 2018 printed as pp. 1-51) (Year: 2018).*
Read, Jon A. et al.; Rapid Identification of Novel Allosteric PRC2 Inhibitors; ACS Chem. Biol. Sep. 16, 2019, 14, pp. 21347-2140.
Khanna, Avinash et al.; Design, Synthesis and Pharmacological Evaluation of Second Generation EZH3 Inhibitors with Long Residence Time; ACS Med. Chem. Lett. 2020, 11, pp. 1205-1212; Mar. 26, 2020.
Li, Yansheng et al.; A Compound AC1Q3QWB Selectivity Disrupts HOTAIR-Mediated Recruitment of PRC2 and Enhances Cancer Therapy of DZNep; Theran ostics Jun. 24, 2019, vol. 9, Issue 16; pp. 4608-4623.
Qi Wei et al.; Selective Inhibition of Ezh2 by a small molecule inhibitor blocks tumor cells proliferation; Proceedings of the National Academy of Sciences; Dec. 26, 2012 vol. 109, No. 52; pp. 21360-21365.
Kim, Woojin et al.; Targeted disruption of the EZH-2-EED complex inhibits EZH2-dependent cancer; Nature Chemical Biology; Published online Aug. 25, 2013; 10 pages.
Richart, Laia et al.; Drugging histone methyltransferases in cancer; Current Opinion in Chemical Biology; Jan. 23, 2020, 56; pp. 51-62.
Ma, Anqi; Discovery of a first-in-class EZH2 selective degrader; Nat. Chem. Biol. Feb. 2020; 16(2): 214-222.
Qi, Wei et al.; An allosteric PRC2 inhibitors targeting the H3K27me3 binding pocket of EED, Nature Chemical Biology, vol. 13, Jan. 20, 2017; pp. 381-391.
He, Yupeng et al.; The EED protein-protein interaction inhibitor A-395 inactivates the PRC2 complex; Nature Chemical Biology, vol. 13, Jan. 30, 2017; pp. 389-399.
Knutson, Sarah et al.; A selective inhibitor of EZH2 blocked H3K27 methylation and kills mutant lymphoma cells; Nature Chemical Biology, vol. 8, Sep. 30, 2012; pp. 890-896.
Italiano, Antoine et al.; Tazemetostat, an EZH2 inhibitor, in relapsed or refractory B-cell non-Hodgkin lymphoma and advanced solid tumours: a first-in-human, open-label, phase 1 study; Lancet Oncol. Apr. 9, 2018; 19(5): 649-659.
Martin, Cynthia et al.; Small Molecule Approaches for Targeting the Polycomb Repressive Complex 2 (PRC2) in Cancer; J. Med. Chem. Dec. 7, 2020; 27 pages.
Kung, Pei-Pei et al.; Optimization of Orally Bioavailable Enhancer of Zeste Homolog 2 (EZH2) Inhibitors Using Ligand and Property-Based Design Strategies: Identification of Development Candidate (R)-5,8-Dichloro-7-(methoxy (oxetan-3-yl)methyl)-2-((4-methoxy-6-methyl-2-oxo-1,2-dihydropyridin-3-yl)methyl)-3,4-dihydroisoquinolin-1(2H)-one (PF-06821497); J. Med. Chem. Dec. 6, 2017, 61, 650-665.

(Continued)

*Primary Examiner* — Ronald T Niebauer
(74) *Attorney, Agent, or Firm* — Peter J. Mikesell; Schmeiser, Olsen & Watts, LLP

(57) ABSTRACT

This disclosure describes three novel bisthioether stapled peptides as allosteric inhibitors of Polycomb Repressive Complex 2 (PRC2) catalytic function with demonstrated cell permeability, potent activity in physiological conditions, and strong antiproliferative effects on cancer cells. These inhibitors target, for the first time, two protein interfaces in PRC2 that are crucial for its proper assembling and thus for its histone methyltransferase activity.

2 Claims, 58 Drawing Sheets
Specification includes a Sequence Listing.

(56) References Cited

OTHER PUBLICATIONS

Huang, Ying et al.; Discovery of First-in-Class, Potent, and Orally Bioavailable Embryonic Ectoderm Development (EED) Inhibitor with Robust Anticancer Efficacy; J Med. Chem. Jan. 16, 2017; vol. 60, pp. 2215-2226.

Yang, Chao-Yie et al.; Allosteric Inactivation of Polycomb Repressive Complex 2 (PRC2) by Inhibiting Its Adapter Protein: Embryonic Ectodomain Development (EED), J. Med. Chem. Mar. 3, 2017, 60, 2212-2214.

Vaswani; Rishi et al.; Identification of (R)-N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas, J. Med. Chem. Oct. 14, 2016, 59, 9928-9941.

Dockerill, Milly; Targeting PRC2 for the treatment of cancer: an updated patent review (2016-2020), Expert Opinion on Therapeutic Patents, Oct. 24, 2020; 37 pages.

Fioravanti, Rossella; Six Years (2012-2018) of Researches on Catalytic EZH2 Inhibitors: The Boom of the 2-Pyridone Compounds, Chem Rec. Oct. 19, 2018; 18(12): 1818-1832.

Hsu, Jessie Hao-Ru; EED-Targeted PROTACs Degrade EED, EZH2, and SUZ12 in the PRC2 Complex; Cell Chemical Biology 27, 41-46, Jan. 16, 2020.

Zhou, Yan et al.; Identification of catalytic and non-catalytic activity inhibitors against PRC2-EZH2 complex through multiple high-throughput screening campaigns; Chem Biol Drug Des. Oct. 2020; 96:1024-1050.

Honma Daisuke et al.; Novel orally bioavailable EZH1/2 dual inhibitors with greater antitumor efficacy than an EZH2 selective inhibitor; Cancer Sci 108 (2017) 2069-2078.

Eich, Marie-Lisa et al.; EZH2-Targeted Therapies in Cancer: Hype or a Reality, Cancer Research. Sep. 25, 2020; 11 Pages.

Zhang Kai-li et al.; AZD9291 inactivates the PRC2 complex to mediate tumor growth inhibition; Acta Pharmacologica Sinica (Jun. 6, 2019) 40:1587-1595.

Harb W. et al.; A phase 1 study of CPI-1205, a small molecule inhibitor of EZH2, preliminary safety in patients with B-cell lymphomas; Annals of Oncology, Abstracts of Proffered Papers (Oral), vol. 29, No. 3, Mar. 1, 2018.

Zhang, Gan et al.; A Solid-Phase Approach to Accessing Bisthioether-Stapled Peptides Resulting in a Potent Inhibitor of PRC2 Catalytic Activity; Angew Chem Int Ed Engl Angew Chem Int Ed Engl. Nov. 26, 2018;57 (52):17073-17078.

* cited by examiner

S4
SEQ ID NO: 37

| Cpd | Structure | Linker | SEQ ID NO: | Helicity (%) | IC50 (uM) |
|---|---|---|---|---|---|
| 1 | Ac-TVDKIASALSVLAEEVPQN-CONH2 | --- | SEQ ID NO: 4 | 4.80% | 89 |
| 2 (GN-ZB2) | Ac-TVD[CIASC]LSVLAEEVPQN-CONH2 | CH2CH2CH2 | SEQ ID NO: 1 | 23 | 0.17±0.02 |
| 3 | Ac-TVD[CIASC]LSVLAEEVPQN-CONH2 | CH2(CH2)3CH2 | SEQ ID NO: 5 | 9.7 | 8.8±1.1 |
| 4 | Ac-TVDKIASA[CSVLAEEC]PQN-CONH2 | CH2(CH2)4CH2 | SEQ ID NO: 6 | 8.7 | 10.1±1.1 |
| 5 | Ac-TVDKIASA[CSVLAEEC]PQN-CONH2 | CH2(CH2)5CH2 | SEQ ID NO: 7 | 13.7 | 27.1±1.2 |
| 6 | Ac-TVDKIASA[CSVLAEEC]PQN-CONH2 | CH2(CH2)6CH2 | SEQ ID NO: 8 | 12.1 | 17±1.4 |

FIG. 2A

SEQ ID NO: 39

SEQ ID NO: 40

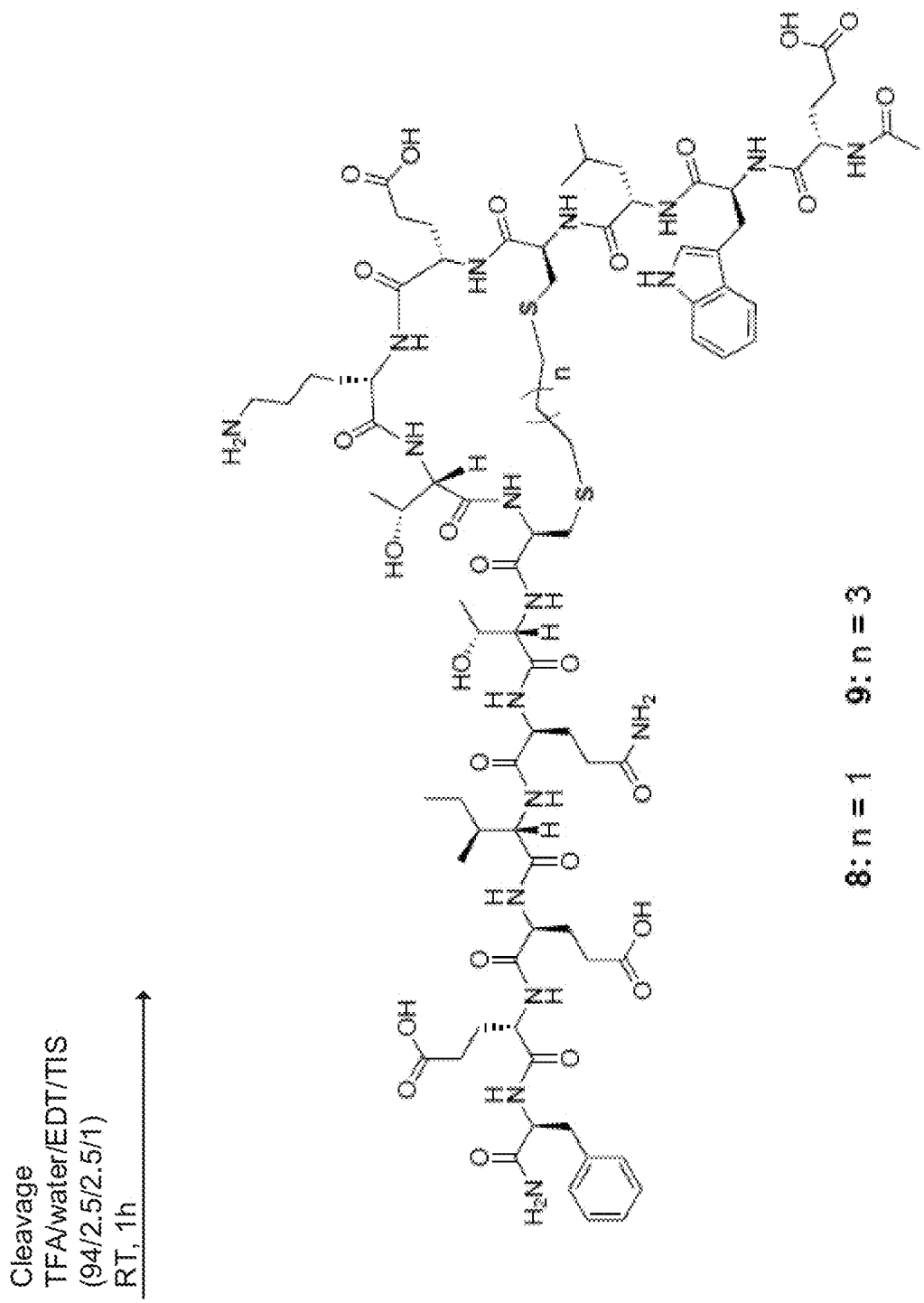

SEQ ID NO: 41

SEQ ID NO: 42

| Cpd | Structure | Linker | SEQ ID NO: |
|---|---|---|---|
| 7 | EWLREKTITQIEEF | --- | SEQ ID NO: 9 |
| 8 | EWL[SEKTC]TQIEEF | CH2CH2CH2 | SEQ ID NO: 10 |
| 9 | EWL[SEKTC]TQIEEF | CH2(CH2)3CH2 | SEQ ID NO: 11 |
| 10 | LCRNFMLHLVSMHDFLI | --- | SEQ ID NO: 12 |
| 11 (GN-ZW11) | LCRN[CMLHC]VSMHDFLI | CH2CH2CH2 | SEQ ID NO: 2 |
| 12 | LCRN[CMLHC]VSMHDFLI | CH2(CH2)3CH2 | SEQ ID NO: 13 |

| Cpd | Proteolytic Stability (Chymotripsin, t1/2) | Proteolytic Stability (Plasma, t1/2) | Helicity (%) | H3K27Me3 Inhibition (% at 1 mM) |
|---|---|---|---|---|
| 7 | 7.6 min | 5.9 min | 20.9 | 33.4 |
| 8 | 2.1 h | 1.8 h | 38.4 | 54.9 |
| 9 | 3 h | 2.2 h | 19.7 | 31.1 |
| 10 | 8.9 min | 7.7 min | 59.9 | 78.3 |
| 11 (GN-ZW11) | 14.4 h | 7.3 h | 95.1 | 98.3 |
| 12 | 7.2 h | 7.1 h | 61.6 | 38.5 |

FIG. 5A

| Compound: | IC$_{50}$ (µM) |
|---|---|
| 10 | 3.21 ± 1.47 |
| 11 (Nuclear extract) | 0.32 ± 0.10 |
| 11 (Recombinant PRC2) | 0.49 ± 0.11 |
| GSK126 | 0.10 ± 0.01 |

SEQ ID NO: 43

SEQ ID NO: 44

| Cpd | Sequence | Linker | SEQ ID NO. | HPLC Purity % | LC/MS Purity % | Helicity |
|---|---|---|---|---|---|---|
| 13 | Ac-VINEEYKIWKKNTPFL | --- | SEQ ID NO. 14 | 99.3 | 99.1 | 16.38 |
| 14 | Ac-VI[CEEYC]IWKKNTPFL | CH2CH2CH2 | SEQ ID NO. 15 | 98.7 | 98.6 | 12.67 |
| 15 | Ac-VI[CEEYC]IWKKNTPFL | CH2CH2CH2CH2 | SEQ ID NO. 16 | 99.3 | 98.9 | 11.49 |
| 16 | Ac-VI[CEEYC]IWKKNTPFL | CH2CHCHCH2 | SEQ ID NO. 17 | 99.5 | 98.6 | 18.97 |
| 17 | Ac-VI[CEEYC]IWKKNTPFL | CH2CH2CH2CH2CH2 | SEQ ID NO. 18 | 96.7 | 97.6 | 10.98 |
| 18 | Ac-VI[CEEYC]IWKKNTPFL | CH2CH2CH2CH2CH2CH2 | SEQ ID NO. 19 | 97.7 | 96.9 | 19.41 |
| 19 | Ac-VINEEY[CIWKC]NTPFL | CH2CH2CH2 | SEQ ID NO. 20 | 98.6 | 98.9 | 18.36 |
| 20 | Ac-VINEEY[CIWKC]NTPFL | CH2CH2CH2CH2 | SEQ ID NO. 21 | 97.3 | 96.8 | 16.49 |
| 21 | Ac-VINEEY[CIWKC]NTPFL | CH2CHCHCH2 | SEQ ID NO. 22 | 98.1 | 97.1 | 24.2 |
| 22 | Ac-VINEEY[CIWKC]NTPFL | CH2CH2CH2CH2CH2 | SEQ ID NO. 23 | 97.1 | 97 | 5.68 |
| 23 | Ac-VINEEY[CIWKC]NTPFL | CH2CH2CH2CH2CH2CH2 | SEQ ID NO. 24 | 96.9 | 97 | 19.41 |
| 24 | Ac-VINEEC[KIWKKC]NTPFL | CH2CH2CH2 | SEQ ID NO. 3 | 96.9 | 97 | 97 |
| 25 | Ac-V[CNEEC]KIWKKNTPFL | CH2CH2CH2CH2 | SEQ ID NO. 25 | 97.8 | 99.1 | 99.1 |
| 26 | Ac-V[CNEEC]KIWKKNTPFL | CH2CHCHCH2 | SEQ ID NO. 26 | 96.8 | 95.1 | 95.1 |
| 27 | Ac-V[CNEEC]KIWKKNTPFL | CH2CH2CH2CH2CH2 | SEQ ID NO. 27 | 97.8 | 98 | 98 |
| 28 | Ac-V[CNEEC]KIWKKNTPFL | CH2CH2CH2CH2CH2CH2 | SEQ ID NO. 28 | 97.8 | 99.1 | 99.1 |
| 29 | VINEEYKIWKKN[CPFLC] | CH2CH2CH2 | SEQ ID NO. 29 | 96.8 | 95.9 | 95.9 |
| 30 | VINEEYKIWKKN[CPFLC] | CH2CH2CH2CH2 | SEQ ID NO. 30 | 97.6 | 97.2 | 97.2 |
| 31 | VINEEYKIWKKN[CPFLC] | CH2CHCHCH2 | SEQ ID NO. 31 | 99.1 | 99 | 99 |
| 32 | VINEEYKIWKKN[CPFLC] | CH2CH2CH2CH2CH2 | SEQ ID NO. 32 | 98.9 | 98.3 | 98.3 |
| 33 | VINEEYKIWKKN[CPFLC] | CH2CH2CH2CH2CH2CH2 | SEQ ID NO. 33 | 97.1 | 96 | 96 |

FIG. 8A

SEQ ID NO: 47

Chemoselective Mmt deprotection
2% TFA
10% TIS
88% DCM

SEQ ID NO: 48

SEQ ID NO: 49

SEQ ID NO: 55

SEQ ID NO: 56

SEQUENCE LISTING

<160> NUMBER OF SEQ ID NOS: 56

<210> SEQ ID NO 1
<211> LENGTH: 19
<212> TYPE: PRT
<213> ORGANISM: Artificial Sequence
<220> FEATURE:
<223> OTHER INFORMATION: Synthetic bisthioether stapled peptide; GN-ZB2
<220> FEATURE:
<221> NAME/KEY: THIOETH
<222> LOCATION: (4)..(8)
<223> OTHER INFORMATION: (CH2)3 linker between residues 4 and 8

<400> SEQUENCE: 1

Thr Val Asp Cys Ile Ala Ser Cys Leu Ser Val Leu Ala Glu Glu Val
1               5                   10                  15

Pro Gln Asn

<210> SEQ ID NO 2
<211> LENGTH: 17
<212> TYPE: PRT
<213> ORGANISM: Artificial Sequence
<220> FEATURE:
<223> OTHER INFORMATION: Synthetic bisthioether stapled peptide; GN-ZW11
<220> FEATURE:
<221> NAME/KEY: THIOETH
<222> LOCATION: (5)..(9)
<223> OTHER INFORMATION: (CH2)3 linker between residues 5 and 9

<400> SEQUENCE: 2

Leu Cys Arg Asn Cys Met Leu His Cys Val Ser Met His Asp Phe Leu
1               5                   10                  15

Ile

<210> SEQ ID NO 3
<211> LENGTH: 16
<212> TYPE: PRT
<213> ORGANISM: Artificial Sequence
<220> FEATURE:
<223> OTHER INFORMATION: Synthetic bisthioether stapled peptide; GN-Z24
<220> FEATURE:
<221> NAME/KEY: THIOETH
<222> LOCATION: (2)..(6)
<223> OTHER INFORMATION: (CH2)3 linker between residues 2 and 6

<400> SEQUENCE: 3

Val Cys Asn Glu Glu Cys Lys Ile Trp Lys Lys Asn Thr Pro Phe Leu
1               5                   10                  15

<210> SEQ ID NO 4
<211> LENGTH: 19
<212> TYPE: PRT
<213> ORGANISM: Artificial Sequence
<220> FEATURE:
<223> OTHER INFORMATION: wild type linear peptide; compound 1

<400> SEQUENCE: 4

Thr Val Asp Lys Ile Ala Ser Ala Leu Ser Val Leu Ala Glu Glu Val
1               5                   10                  15

Pro Gln Asn

<210> SEQ ID NO 5
<211> LENGTH: 19
<212> TYPE: PRT
<213> ORGANISM: Artificial Sequence
<220> FEATURE:
<223> OTHER INFORMATION: Synthetic bisthioether stapled peptide;

```
     compound 3
<220> FEATURE:
<221> NAME/KEY: THIOETH
<222> LOCATION: (4)..(8)
<223> OTHER INFORMATION: (CH2)5 linker between residues 4 and 8

<400> SEQUENCE: 5

Thr Val Asp Cys Ile Ala Ser Cys Leu Ser Val Leu Ala Glu Glu Val
1               5                   10                  15

Pro Gln Asn

<210> SEQ ID NO 6
<211> LENGTH: 19
<212> TYPE: PRT
<213> ORGANISM: Artificial Sequence
<220> FEATURE:
<223> OTHER INFORMATION: Synthetic bisthioether stapled peptide;
      compound 4
<220> FEATURE:
<221> NAME/KEY: THIOETH
<222> LOCATION: (9)..(16)
<223> OTHER INFORMATION: (CH2)6 linker between residues 9 and 16

<400> SEQUENCE: 6

Thr Val Asp Lys Ile Ala Ser Ala Cys Ser Val Leu Ala Glu Glu Cys
1               5                   10                  15

Pro Gln Asn

<210> SEQ ID NO 7
<211> LENGTH: 19
<212> TYPE: PRT
<213> ORGANISM: Artificial Sequence
<220> FEATURE:
<223> OTHER INFORMATION: Synthetic bisthioether stapled peptide;
      Compound 5
<220> FEATURE:
<221> NAME/KEY: THIOETH
<222> LOCATION: (9)..(16)
<223> OTHER INFORMATION: (CH2)7 linker between residues 9 and 16

<400> SEQUENCE: 7

Thr Val Asp Lys Ile Ala Ser Ala Cys Ser Val Leu Ala Glu Glu Cys
1               5                   10                  15

Pro Gln Asn

<210> SEQ ID NO 8
<211> LENGTH: 19
<212> TYPE: PRT
<213> ORGANISM: Artificial Sequence
<220> FEATURE:
<223> OTHER INFORMATION: Synthetic bisthioether stapled peptide;
      Compound 6
<220> FEATURE:
<221> NAME/KEY: THIOETH
<222> LOCATION: (9)..(16)
<223> OTHER INFORMATION: (CH2)8 linker between residues 9 and 16

<400> SEQUENCE: 8

Thr Val Asp Lys Ile Ala Ser Ala Cys Ser Val Leu Ala Glu Glu Cys
1               5                   10                  15

Pro Gln Asn

<210> SEQ ID NO 9
<211> LENGTH: 14
<212> TYPE: PRT
<213> ORGANISM: Artificial Sequence
<220> FEATURE:
```

```
<223> OTHER INFORMATION: Synthetic wildtype linear peptide, compound 7

<400> SEQUENCE: 9

Glu Trp Leu Arg Glu Lys Thr Ile Thr Gln Ile Glu Glu Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic bisthioether stapled peptide;
      compound 8
<220> FEATURE:
<221> NAME/KEY: THIOETH
<222> LOCATION: (4)..(8)
<223> OTHER INFORMATION: (CH2)3 linker between residues 4 and 8

<400> SEQUENCE: 10

Glu Trp Leu Cys Glu Lys Thr Cys Thr Gln Ile Glu Glu Phe
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic bisthioether stapled peptide;
      compound 9
<220> FEATURE:
<221> NAME/KEY: THIOETH
<222> LOCATION: (4)..(8)
<223> OTHER INFORMATION: (CH2)5 linker between residues 4 and 8

<400> SEQUENCE: 11

Glu Trp Leu Cys Glu Lys Thr Cys Thr Gln Ile Glu Glu Phe
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic wildtype linear peptide, compound 10

<400> SEQUENCE: 12

Leu Cys Arg Asn Phe Met Leu His Leu Val Ser Met His Asp Phe Leu
1               5                   10                  15

Ile

<210> SEQ ID NO 13
<211> LENGTH: 17
<212> TYPE: PRT
<213> ORGANISM: Artificial Sequence
<220> FEATURE:
<223> OTHER INFORMATION: Synthetic bisthioether stapled peptide;
      compound 12
<220> FEATURE:
<221> NAME/KEY: THIOETH
<222> LOCATION: (5)..(9)
<223> OTHER INFORMATION: (CH2)5 linker between residues 5 and 9

<400> SEQUENCE: 13

Leu Cys Arg Asn Cys Met Leu His Cys Val Ser Met His Asp Phe Leu
1               5                   10                  15

Ile
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetic wildtype linear protein; compound 13

<400> SEQUENCE: 14

Val Ile Asn Glu Glu Tyr Lys Ile Trp Lys Lys Asn Thr Pro Phe Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 14
<220> FEATURE:
<221> NAME/KEY: THIOETH
<222> LOCATION: (3)..(7)
<223> OTHER INFORMATION: (CH2)3 linker between residues 3 and 7

<400> SEQUENCE: 15

Val Ile Cys Glu Glu Tyr Cys Ile Trp Lys Lys Asn Thr Pro Phe Leu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic bisthioether stapled peptide;
      compound 15
<220> FEATURE:
<221> NAME/KEY: THIOETH
<222> LOCATION: (3)..(7)
<223> OTHER INFORMATION: (CH2)4 linker between residues 3 and 7

<400> SEQUENCE: 16

Val Ile Cys Glu Glu Tyr Cys Ile Trp Lys Lys Asn Thr Pro Phe Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 16
<220> FEATURE:
<221> NAME/KEY: THIOETH
<222> LOCATION: (3)..(8)
<223> OTHER INFORMATION: CH2CHCHCH2 linker between residues 3 and 7

<400> SEQUENCE: 17

Val Ile Cys Glu Glu Tyr Cys Ile Trp Lys Lys Asn Thr Pro Phe Leu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 17
<220> FEATURE:
<221> NAME/KEY: THIOETH
<222> LOCATION: (3)..(7)
<223> OTHER INFORMATION: (CH2)5 linker between residues 3 and 7
```

```
<400> SEQUENCE: 18

Val Ile Cys Glu Glu Tyr Cys Ile Trp Lys Lys Asn Thr Pro Phe Leu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 18
<220> FEATURE:
<221> NAME/KEY: THIOETH
<222> LOCATION: (3)..(7)
<223> OTHER INFORMATION: (CH2)6 linker between residues 3 and 7

<400> SEQUENCE: 19

Val Ile Cys Glu Glu Tyr Cys Ile Trp Lys Lys Asn Thr Pro Phe Leu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 19
<220> FEATURE:
<221> NAME/KEY: THIOETH
<222> LOCATION: (7)..(11)
<223> OTHER INFORMATION: (CH2)3 linker between residues 7 and 11

<400> SEQUENCE: 20

Val Ile Asn Glu Glu Tyr Cys Ile Trp Lys Cys Asn Thr Pro Phe Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 20
<220> FEATURE:
<221> NAME/KEY: THIOETH
<222> LOCATION: (7)..(11)
<223> OTHER INFORMATION: (CH2)4 linker between residues 7 and 11

<400> SEQUENCE: 21

Val Ile Asn Glu Glu Tyr Cys Ile Trp Lys Cys Asn Thr Pro Phe Leu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 21
<220> FEATURE:
<221> NAME/KEY: THIOETH
<222> LOCATION: (7)..(11)
<223> OTHER INFORMATION: CH2CHCHCH2 linker between residues 7 and 11

<400> SEQUENCE: 22

Val Ile Asn Glu Glu Tyr Cys Ile Trp Lys Cys Asn Thr Pro Phe Leu
1               5                   10                  15

<210> SEQ ID NO 23
```

```
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 22
<220> FEATURE:
<221> NAME/KEY: THIOETH
<222> LOCATION: (7)..(11)
<223> OTHER INFORMATION: (CH2)5 linker between residues 7 and 11

<400> SEQUENCE: 23

Val Ile Asn Glu Glu Tyr Cys Ile Trp Lys Cys Asn Thr Pro Phe Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 23
<220> FEATURE:
<221> NAME/KEY: THIOETH
<222> LOCATION: (7)..(11)
<223> OTHER INFORMATION: (CH2)6 linker between residues 7 and 11

<400> SEQUENCE: 24

Val Ile Asn Glu Glu Tyr Cys Ile Trp Lys Cys Asn Thr Pro Phe Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 25
<220> FEATURE:
<221> NAME/KEY: THIOETH
<222> LOCATION: (2)..(6)
<223> OTHER INFORMATION: (CH2)4 linker between residues 2 and 6

<400> SEQUENCE: 25

Val Cys Asn Glu Glu Cys Lys Ile Trp Lys Lys Asn Thr Pro Phe Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 26
<220> FEATURE:
<221> NAME/KEY: THIOETH
<222> LOCATION: (2)..(6)
<223> OTHER INFORMATION: CH2CHCHCH2 linker between residues 2 and 6

<400> SEQUENCE: 26

Val Cys Asn Glu Glu Cys Lys Ile Trp Lys Lys Asn Thr Pro Phe Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic bisthioether stapled peptide;
      Compound 27
<220> FEATURE:
```

```
<221> NAME/KEY: THIOETH
<222> LOCATION: (2)..(6)
<223> OTHER INFORMATION: (CH2)5 linker between residues 2 and 6

<400> SEQUENCE: 27

Val Cys Asn Glu Glu Cys Lys Ile Trp Lys Lys Asn Thr Pro Phe Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic bisthioether stapled peptide;
      compound 28
<220> FEATURE:
<221> NAME/KEY: THIOETH
<222> LOCATION: (2)..(6)
<223> OTHER INFORMATION: (CH2)6 linker between residues 2 and 6

<400> SEQUENCE: 28

Val Cys Asn Glu Glu Cys Lys Ile Trp Lys Lys Asn Thr Pro Phe Leu
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Synthetic bisthioether stapled peptide;
      Compound 29
<220> FEATURE:
<221> NAME/KEY: THIOETH
<222> LOCATION: (13)..(17)
<223> OTHER INFORMATION: (CH2)3 linker between residues 13 and 17

<400> SEQUENCE: 29

Val Ile Asn Glu Glu Tyr Lys Ile Trp Lys Lys Asn Cys Pro Phe Leu
1               5                   10                  15
Cys

<210> SEQ ID NO 30
<211> LENGTH: 17
<212> TYPE: PRT
<213> ORGANISM: Artificial Sequence
<220> FEATURE:
<223> OTHER INFORMATION: Synthetic bisthioether stapled peptide;
      Compound 30
<220> FEATURE:
<221> NAME/KEY: THIOETH
<222> LOCATION: (13)..(17)
<223> OTHER INFORMATION: (CH2)4 linker between residues 13 and 17

<400> SEQUENCE: 30

Val Ile Asn Glu Glu Tyr Lys Ile Trp Lys Lys Asn Cys Pro Phe Leu
1               5                   10                  15
Cys

<210> SEQ ID NO 31
<211> LENGTH: 17
<212> TYPE: PRT
<213> ORGANISM: Artificial Sequence
<220> FEATURE:
<223> OTHER INFORMATION: Synthetic bisthioether stapled peptide;
      Compound 31
<220> FEATURE:
<221> NAME/KEY: THIOETH
<222> LOCATION: (13)..(17)
<223> OTHER INFORMATION: CH2CHCHCH2 linker between residues 13 and 17
```

```
<400> SEQUENCE: 31

Val Ile Asn Glu Glu Tyr Lys Ile Trp Lys Lys Asn Cys Pro Phe Leu
1               5                   10                  15

Cys

<210> SEQ ID NO 32
<211> LENGTH: 17
<212> TYPE: PRT
<213> ORGANISM: Artificial Sequence
<220> FEATURE:
<223> OTHER INFORMATION: Synthetic bisthioether stapled peptide;
      Compound 32
<220> FEATURE:
<221> NAME/KEY: THIOETH
<222> LOCATION: (13)..(17)
<223> OTHER INFORMATION: (CH2)5 linker between residues 13 and 17

<400> SEQUENCE: 32

Val Ile Asn Glu Glu Tyr Lys Ile Trp Lys Lys Asn Cys Pro Phe Leu
1               5                   10                  15

Cys

<210> SEQ ID NO 33
<211> LENGTH: 17
<212> TYPE: PRT
<213> ORGANISM: Artificial Sequence
<220> FEATURE:
<223> OTHER INFORMATION: Synthetic bisthioether stapled peptide;
      Compound 32
<220> FEATURE:
<221> NAME/KEY: THIOETH
<222> LOCATION: (13)..(17)
<223> OTHER INFORMATION: (CH2)6 linker between residues 13 and 17

<400> SEQUENCE: 33

Val Ile Asn Glu Glu Tyr Lys Ile Trp Lys Lys Asn Cys Pro Phe Leu
1               5                   10                  15

Cys

<210> SEQ ID NO 34
<211> LENGTH: 19
<212> TYPE: PRT
<213> ORGANISM: Artificial Sequence
<220> FEATURE:
<223> OTHER INFORMATION: Synthetic bisthioether stapled peptide;
      Compound GN-ZB2a
<220> FEATURE:
<221> NAME/KEY: THIOETH
<222> LOCATION: (4)..(8)
<223> OTHER INFORMATION: (CH2)3 linker between residues 4 and 8

<400> SEQUENCE: 34

Lys Arg Val Cys Ser Glu Tyr Cys Arg Leu Arg Gln Leu Lys Arg Phe
1               5                   10                  15

Arg Arg Ala

<210> SEQ ID NO 35
<211> LENGTH: 19
<212> TYPE: PRT
<213> ORGANISM: Artificial Sequence
<220> FEATURE:
<223> OTHER INFORMATION: Synthetic bisthioether peptide; Compound S2
<220> FEATURE:
<221> NAME/KEY: MISC_FEATURE
<222> LOCATION: (1)..(1)
<223> OTHER INFORMATION: Protected as t-butyl ether
```

-continued

```
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (7)..(7)
<223> OTHER INFORMATION: Protected as cyclic ether
<220> FEATURE:
<221> NAME/KEY: MISC_FEATURE
<222> LOCATION: (10)..(10)
<223> OTHER INFORMATION: Protected as cyclic ether
<220> FEATURE:
<221> NAME/KEY: MISC_FEATURE
<222> LOCATION: (14)..(15)
<223> OTHER INFORMATION: Protected as t-butyl ester
<220> FEATURE:
<221> NAME/KEY: MISC_FEATURE
<222> LOCATION: (18)..(19)
<223> OTHER INFORMATION: Protected as trityl

<400> SEQUENCE: 35

Thr Val Asp Cys Ile Ala Ser Cys Leu Ser Val Leu Ala Glu Glu Val
1               5                   10                  15

Pro Gln Asn

<210> SEQ ID NO 36
<211> LENGTH: 19
<212> TYPE: PRT
<213> ORGANISM: Artificial Sequence
<220> FEATURE:
<223> OTHER INFORMATION: Synthetic bisthioether peptide; Compound S1
<220> FEATURE:
<221> NAME/KEY: MISC_FEATURE
<222> LOCATION: (1)..(1)
<223> OTHER INFORMATION: Protected as t-butyl ether
<220> FEATURE:
<221> NAME/KEY: MISC_FEATURE
<222> LOCATION: (3)..(3)
<223> OTHER INFORMATION: Protected as t-butyl ether
<220> FEATURE:
<221> NAME/KEY: MISC_FEATURE
<222> LOCATION: (4)..(4)
<223> OTHER INFORMATION: Protected as monomethoxytrityl
<220> FEATURE:
<221> NAME/KEY: MISC_FEATURE
<222> LOCATION: (7)..(7)
<223> OTHER INFORMATION: Protected as cyclic ether
<220> FEATURE:
<221> NAME/KEY: MISC_FEATURE
<222> LOCATION: (8)..(8)
<223> OTHER INFORMATION: Protected as monomethoxytrityl
<220> FEATURE:
<221> NAME/KEY: MISC_FEATURE
<222> LOCATION: (10)..(10)
<223> OTHER INFORMATION: Protected as cyclic ether
<220> FEATURE:
<221> NAME/KEY: MISC_FEATURE
<222> LOCATION: (14)..(15)
<223> OTHER INFORMATION: Protected as t-butyl ester
<220> FEATURE:
<221> NAME/KEY: MISC_FEATURE
<222> LOCATION: (18)..(19)
<223> OTHER INFORMATION: Protected as trityl

<400> SEQUENCE: 36

Thr Val Asp Cys Ile Ala Ser Cys Leu Ser Val Leu Ala Glu Glu Val
1               5                   10                  15

Pro Gln Asn

<210> SEQ ID NO 37
<211> LENGTH: 18
<212> TYPE: PRT
```

```
<213> ORGANISM: Artificial Sequence
<220> FEATURE:
<223> OTHER INFORMATION: Synthetic bisthioether peptide, compound S4
<220> FEATURE:
<221> NAME/KEY: MISC_FEATURE
<222> LOCATION: (1)..(1)
<223> OTHER INFORMATION: Protected as t-butyl ether
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (4)..(4)
<223> OTHER INFORMATION: Protected as N-Boc
<220> FEATURE:
<221> NAME/KEY: MISC_FEATURE
<222> LOCATION: (7)..(7)
<223> OTHER INFORMATION: Protected as cyclic ether
<220> FEATURE:
<221> NAME/KEY: MISC_FEATURE
<222> LOCATION: (9)..(9)
<223> OTHER INFORMATION: Protected as monomethoxytrityl
<220> FEATURE:
<221> NAME/KEY: MISC_FEATURE
<222> LOCATION: (10)..(10)
<223> OTHER INFORMATION: Protected as t-butyl ether
<220> FEATURE:
<221> NAME/KEY: MISC_FEATURE
<222> LOCATION: (14)..(15)
<223> OTHER INFORMATION: Protected as t-butyl ester
<220> FEATURE:
<221> NAME/KEY: MISC_FEATURE
<222> LOCATION: (17)..(18)
<223> OTHER INFORMATION: Protected as trityl

<400> SEQUENCE: 37

Thr Val Asp Lys Ile Ala Ser Ala Cys Ser Val Leu Ala Glu Glu Cys
1               5                   10                  15

Gln Asn

<210> SEQ ID NO 38
<211> LENGTH: 18
<212> TYPE: PRT
<213> ORGANISM: Artificial Sequence
<220> FEATURE:
<223> OTHER INFORMATION: Synthetic bisthioether peptide, compound S5
<220> FEATURE:
<221> NAME/KEY: MISC_FEATURE
<222> LOCATION: (1)..(1)
<223> OTHER INFORMATION: Protected as t-butyl ether
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (4)..(4)
<223> OTHER INFORMATION: Protected as N-Boc
<220> FEATURE:
<221> NAME/KEY: MISC_FEATURE
<222> LOCATION: (7)..(7)
<223> OTHER INFORMATION: Protected as cyclic ether
<220> FEATURE:
<221> NAME/KEY: MISC_FEATURE
<222> LOCATION: (10)..(10)
<223> OTHER INFORMATION: Protected as cyclic ether
<220> FEATURE:
<221> NAME/KEY: MISC_FEATURE
<222> LOCATION: (14)..(15)
<223> OTHER INFORMATION: Protected as t-butyl ester
<220> FEATURE:
<221> NAME/KEY: MISC_FEATURE
<222> LOCATION: (17)..(18)
<223> OTHER INFORMATION: Protected as trityl
```

<400> SEQUENCE: 38

Thr Val Asp Lys Ile Ala Ser Ala Cys Ser Val Leu Ala Glu Glu Cys
1               5                   10                  15

Gln Asn

<210> SEQ ID NO 39
<211> LENGTH: 14
<212> TYPE: PRT
<213> ORGANISM: Artificial Sequence
<220> FEATURE:
<223> OTHER INFORMATION: Synethic bisthioether peptide
<220> FEATURE:
<221> NAME/KEY: MISC_FEATURE
<222> LOCATION: (1)..(1)
<223> OTHER INFORMATION: Protected as t-butyl ester
<220> FEATURE:
<221> NAME/KEY: MISC_FEATURE
<222> LOCATION: (2)..(2)
<223> OTHER INFORMATION: Protected as N-Boc
<220> FEATURE:
<221> NAME/KEY: MISC_FEATURE
<222> LOCATION: (4)..(4)
<223> OTHER INFORMATION: Protected as monomethoxytrityl
<220> FEATURE:
<221> NAME/KEY: MISC_FEATURE
<222> LOCATION: (5)..(5)
<223> OTHER INFORMATION: Protected as t-butyl ester
<220> FEATURE:
<221> NAME/KEY: MISC_FEATURE
<222> LOCATION: (6)..(6)
<223> OTHER INFORMATION: Protected as N-Boc
<220> FEATURE:
<221> NAME/KEY: MISC_FEATURE
<222> LOCATION: (7)..(7)
<223> OTHER INFORMATION: Protected as t-butyl ether
<220> FEATURE:
<221> NAME/KEY: MISC_FEATURE
<222> LOCATION: (8)..(8)
<223> OTHER INFORMATION: Protected as monomethoxytrityl
<220> FEATURE:
<221> NAME/KEY: MISC_FEATURE
<222> LOCATION: (9)..(9)
<223> OTHER INFORMATION: Protected as t-butyl ether
<220> FEATURE:
<221> NAME/KEY: MISC_FEATURE
<222> LOCATION: (10)..(10)
<223> OTHER INFORMATION: Protected as trityl
<220> FEATURE:
<221> NAME/KEY: MISC_FEATURE
<222> LOCATION: (12)..(13)
<223> OTHER INFORMATION: Protected as t-butyl ester

<400> SEQUENCE: 39

Glu Trp Leu Cys Glu Lys Thr Cys Thr Gln Ile Glu Glu Phe
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (1)..(1)
<223> OTHER INFORMATION: Protected as t-butyl ester
<220> FEATURE:
<221> NAME/KEY: MISC_FEATURE
<222> LOCATION: (2)..(2)
<223> OTHER INFORMATION: Protected as N-Boc
<220> FEATURE:
<221> NAME/KEY: MISC_FEATURE
<222> LOCATION: (5)..(5)
<223> OTHER INFORMATION: Protected as t-butyl ester

```
<220> FEATURE:
<221> NAME/KEY: MISC_FEATURE
<222> LOCATION: (6)..(6)
<223> OTHER INFORMATION: Protected as N-Boc
<220> FEATURE:
<221> NAME/KEY: MISC_FEATURE
<222> LOCATION: (7)..(7)
<223> OTHER INFORMATION: Protected as t-butyl ether
<220> FEATURE:
<221> NAME/KEY: MISC_FEATURE
<222> LOCATION: (9)..(9)
<223> OTHER INFORMATION: Protected as t-butyl ether
<220> FEATURE:
<221> NAME/KEY: MISC_FEATURE
<222> LOCATION: (10)..(10)
<223> OTHER INFORMATION: Protected as trityl
<220> FEATURE:
<221> NAME/KEY: MISC_FEATURE
<222> LOCATION: (12)..(13)
<223> OTHER INFORMATION: Protected as t-butyl ester

<400> SEQUENCE: 40

Glu Trp Leu Cys Glu Lys Thr Cys Thr Gln Ile Glu Glu Phe
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Synthetic bisthioether peptide, compound 10
<220> FEATURE:
<221> NAME/KEY: MISC_FEATURE
<222> LOCATION: (2)..(2)
<223> OTHER INFORMATION: Protected as t-butyl thioether
<220> FEATURE:
<221> NAME/KEY: MISC_FEATURE
<222> LOCATION: (3)..(3)
<223> OTHER INFORMATION: Protected as Pbf
<220> FEATURE:
<221> NAME/KEY: MISC_FEATURE
<222> LOCATION: (4)..(4)
<223> OTHER INFORMATION: Protected as trityl
<220> FEATURE:
<221> NAME/KEY: MISC_FEATURE
<222> LOCATION: (5)..(5)
<223> OTHER INFORMATION: Protected as monomethoxytrityl
<220> FEATURE:
<221> NAME/KEY: MISC_FEATURE
<222> LOCATION: (8)..(8)
<223> OTHER INFORMATION: Protected as trityl
<220> FEATURE:
<221> NAME/KEY: MISC_FEATURE
<222> LOCATION: (9)..(9)
<223> OTHER INFORMATION: Protected as monomethoxytrityl
<220> FEATURE:
<221> NAME/KEY: MISC_FEATURE
<222> LOCATION: (11)..(11)
<223> OTHER INFORMATION: Protected as t-butyl ether
<220> FEATURE:
<221> NAME/KEY: MISC_FEATURE
<222> LOCATION: (13)..(13)
<223> OTHER INFORMATION: Protected as trityl
<220> FEATURE:
<221> NAME/KEY: MISC_FEATURE
<222> LOCATION: (14)..(14)
<223> OTHER INFORMATION: Protected as t-butyl ester

<400> SEQUENCE: 41

Leu Cys Arg Asn Cys Met Leu His Cys Val Ser Met His Asp Phe Leu
1               5                   10                  15

Ile

<210> SEQ ID NO 42
```

```
<211> LENGTH: 17
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (2)..(2)
<223> OTHER INFORMATION: Protected as t-butyl thioether
<220> FEATURE:
<221> NAME/KEY: MISC_FEATURE
<222> LOCATION: (3)..(3)
<223> OTHER INFORMATION: Protected as Pbf
<220> FEATURE:
<221> NAME/KEY: MISC_FEATURE
<222> LOCATION: (4)..(4)
<223> OTHER INFORMATION: Protected as trityl
<220> FEATURE:
<221> NAME/KEY: MISC_FEATURE
<222> LOCATION: (8)..(8)
<223> OTHER INFORMATION: Protected as t-butyl ether
<220> FEATURE:
<221> NAME/KEY: MISC_FEATURE
<222> LOCATION: (11)..(11)
<223> OTHER INFORMATION: Protected as t-butyl ether
<220> FEATURE:
<221> NAME/KEY: MISC_FEATURE
<222> LOCATION: (13)..(13)
<223> OTHER INFORMATION: Protected as trityl
<220> FEATURE:
<221> NAME/KEY: MISC_FEATURE
<222> LOCATION: (14)..(14)
<223> OTHER INFORMATION: Protected as t-butyl ester

<400> SEQUENCE: 42

Leu Cys Arg Asn Cys Met Leu His Cys Val Ser Met His Asp Phe Leu
1               5                   10                  15

Ile

<210> SEQ ID NO 43
<211> LENGTH: 16
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (2)..(2)
<223> OTHER INFORMATION: Protected as Mmt
<220> FEATURE:
<221> NAME/KEY: MISC_FEATURE
<222> LOCATION: (3)..(3)
<223> OTHER INFORMATION: Protected as trityl
<220> FEATURE:
<221> NAME/KEY: MISC_FEATURE
<222> LOCATION: (4)..(5)
<223> OTHER INFORMATION: Protected as t-butyl ester
<220> FEATURE:
<221> NAME/KEY: MISC_FEATURE
<222> LOCATION: (6)..(6)
<223> OTHER INFORMATION: Protected as Mmt
<220> FEATURE:
<221> NAME/KEY: MISC_FEATURE
<222> LOCATION: (7)..(7)
<223> OTHER INFORMATION: Protected as N-Boc
<220> FEATURE:
<221> NAME/KEY: MISC_FEATURE
<222> LOCATION: (9)..(9)
<223> OTHER INFORMATION: Protected as trityl
<220> FEATURE:
<221> NAME/KEY: MISC_FEATURE
<222> LOCATION: (10)..(11)
<223> OTHER INFORMATION: Protected as N-Boc
<220> FEATURE:
<221> NAME/KEY: MISC_FEATURE
<222> LOCATION: (12)..(12)
```

<223> OTHER INFORMATION: Protected as trityl
<220> FEATURE:
<221> NAME/KEY: MISC_FEATURE
<222> LOCATION: (13)..(13)
<223> OTHER INFORMATION: Protected as t-ether

<400> SEQUENCE: 43

Val Cys Asn Glu Glu Cys Lys Ile Trp Lys Lys Asn Thr Pro Phe Leu
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (3)..(3)
<223> OTHER INFORMATION: Protected as Trt
<220> FEATURE:
<221> NAME/KEY: MISC_FEATURE
<222> LOCATION: (4)..(5)
<223> OTHER INFORMATION: Protected as t-butyl ester
<220> FEATURE:
<221> NAME/KEY: MISC_FEATURE
<222> LOCATION: (7)..(7)
<223> OTHER INFORMATION: Protected as N-Boc
<220> FEATURE:
<221> NAME/KEY: MISC_FEATURE
<222> LOCATION: (9)..(9)
<223> OTHER INFORMATION: Protected as trityl
<220> FEATURE:
<221> NAME/KEY: MISC_FEATURE
<222> LOCATION: (10)..(11)
<223> OTHER INFORMATION: Protected as N-Boc
<220> FEATURE:
<221> NAME/KEY: MISC_FEATURE
<222> LOCATION: (12)..(12)
<223> OTHER INFORMATION: Protected as trityl
<220> FEATURE:
<221> NAME/KEY: MISC_FEATURE
<222> LOCATION: (13)..(13)
<223> OTHER INFORMATION: Protected as t-butyl ether

<400> SEQUENCE: 44

Val Cys Asn Glu Glu Cys Lys Ile Trp Lys Lys Asn Thr Pro Phe Leu
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (1)..(1)
<223> OTHER INFORMATION: Protected as Mmt
<220> FEATURE:
<221> NAME/KEY: MISC_FEATURE
<222> LOCATION: (2)..(2)
<223> OTHER INFORMATION: Protected as t-butyl ether
<220> FEATURE:
<221> NAME/KEY: MISC_FEATURE
<222> LOCATION: (4)..(4)
<223> OTHER INFORMATION: Protected as t-butyl ether
<220> FEATURE:
<221> NAME/KEY: MISC_FEATURE
<222> LOCATION: (5)..(5)
<223> OTHER INFORMATION: Protected as Mmt
<220> FEATURE:
<221> NAME/KEY: MISC_FEATURE
<222> LOCATION: (8)..(8)
<223> OTHER INFORMATION: Protected as t-butyl ether -continued

```
<400> SEQUENCE: 45

Cys Ser Leu Ser Cys Leu Ile Ser Leu Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (2)..(2)
<223> OTHER INFORMATION: Protected as t-butyl ether
<220> FEATURE:
<221> NAME/KEY: MISC_FEATURE
<222> LOCATION: (4)..(4)
<223> OTHER INFORMATION: Protected as t-butyl ether
<220> FEATURE:
<221> NAME/KEY: MISC_FEATURE
<222> LOCATION: (8)..(8)
<223> OTHER INFORMATION: Protected as t-butyl ether

<400> SEQUENCE: 46

Cys Ser Leu Ser Cys Leu Ile Ser Leu Ile
1               5                   10

<210> SEQ ID NO 47
<211> LENGTH: 19
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (5)..(5)
<223> OTHER INFORMATION: Protected as cyclic ether
<220> FEATURE:
<221> NAME/KEY: MISC_FEATURE
<222> LOCATION: (6)..(7)
<223> OTHER INFORMATION: Protected as N-Boc
<220> FEATURE:
<221> NAME/KEY: MISC_FEATURE
<222> LOCATION: (9)..(9)
<223> OTHER INFORMATION: Protected as cyclic ether
<220> FEATURE:
<221> NAME/KEY: MISC_FEATURE
<222> LOCATION: (10)..(10)
<223> OTHER INFORMATION: Protected as Mmt
<220> FEATURE:
<221> NAME/KEY: MISC_FEATURE
<222> LOCATION: (11)..(11)
<223> OTHER INFORMATION: Protected as trityl
<220> FEATURE:
<221> NAME/KEY: MISC_FEATURE
<222> LOCATION: (13)..(13)
<223> OTHER INFORMATION: Protected as trityl
<220> FEATURE:
<221> NAME/KEY: MISC_FEATURE
<222> LOCATION: (14)..(14)
<223> OTHER INFORMATION: Protected as MMt
<220> FEATURE:
<221> NAME/KEY: MISC_FEATURE
<222> LOCATION: (17)..(17)
<223> OTHER INFORMATION: Protected as cyclic ether

<400> SEQUENCE: 47

Ile Phe Glu Ala Ser Lys Lys Val Thr Cys Ser Leu Ser Cys Leu Ile
1               5                   10                  15
```

Ser Leu Ile

<210> SEQ ID NO 48
<211> LENGTH: 19
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (5)..(5)
<223> OTHER INFORMATION: Protected as cyclic ether
<220> FEATURE:
<221> NAME/KEY: MISC_FEATURE
<222> LOCATION: (6)..(7)
<223> OTHER INFORMATION: Protected as N-Boc
<220> FEATURE:
<221> NAME/KEY: MISC_FEATURE
<222> LOCATION: (9)..(9)
<223> OTHER INFORMATION: Protected as cyclic ether
<220> FEATURE:
<221> NAME/KEY: MISC_FEATURE
<222> LOCATION: (11)..(11)
<223> OTHER INFORMATION: Protected as trityl
<220> FEATURE:
<221> NAME/KEY: MISC_FEATURE
<222> LOCATION: (13)..(13)
<223> OTHER INFORMATION: Protected as trityl
<220> FEATURE:
<221> NAME/KEY: MISC_FEATURE
<222> LOCATION: (17)..(17)
<223> OTHER INFORMATION: Protected as cyclic ether

<400> SEQUENCE: 48

Ile Phe Glu Ala Ser Lys Lys Val Thr Cys Ser Leu Ser Cys Leu Ile
1               5                   10                  15

Ser Leu Ile

<210> SEQ ID NO 49
<211> LENGTH: 19
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (5)..(5)
<223> OTHER INFORMATION: Protected as cyclic ether
<220> FEATURE:
<221> NAME/KEY: MISC_FEATURE
<222> LOCATION: (6)..(7)
<223> OTHER INFORMATION: Protected as N-Boc
<220> FEATURE:
<221> NAME/KEY: MISC_FEATURE
<222> LOCATION: (9)..(9)
<223> OTHER INFORMATION: Protected as cyclic ether
<220> FEATURE:
<221> NAME/KEY: MISC_FEATURE
<222> LOCATION: (10)..(10)
<223> OTHER INFORMATION: Protected as Mmt
<220> FEATURE:
<221> NAME/KEY: MISC_FEATURE
<222> LOCATION: (11)..(11)
<223> OTHER INFORMATION: Protected as t-butyl ether
<220> FEATURE:
<221> NAME/KEY: MISC_FEATURE
<222> LOCATION: (13)..(13)
<223> OTHER INFORMATION: Protected as cyclic ether
<220> FEATURE:
<221> NAME/KEY: MISC_FEATURE

```
<222> LOCATION: (14)..(14)
<223> OTHER INFORMATION: Protected as trityl
<220> FEATURE:
<221> NAME/KEY: MISC_FEATURE
<222> LOCATION: (17)..(17)
<223> OTHER INFORMATION: Protected as Mmt

<400> SEQUENCE: 49

Ile Phe Ile Ala Ser Lys Lys Val Thr Cys Ser Leu Ser Asn Leu Ile
1               5                   10                  15

Cys Leu Ile

<210> SEQ ID NO 50
<211> LENGTH: 19
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (5)..(5)
<223> OTHER INFORMATION: Protected as cyclic ether
<220> FEATURE:
<221> NAME/KEY: MISC_FEATURE
<222> LOCATION: (6)..(7)
<223> OTHER INFORMATION: Protected as N-Boc
<220> FEATURE:
<221> NAME/KEY: MISC_FEATURE
<222> LOCATION: (9)..(9)
<223> OTHER INFORMATION: Protected as cyclic ether
<220> FEATURE:
<221> NAME/KEY: MISC_FEATURE
<222> LOCATION: (10)..(10)
<223> OTHER INFORMATION: Protected as Mmt
<220> FEATURE:
<221> NAME/KEY: MISC_FEATURE
<222> LOCATION: (11)..(11)
<223> OTHER INFORMATION: Protected as t-butyl ether
<220> FEATURE:
<221> NAME/KEY: MISC_FEATURE
<222> LOCATION: (13)..(13)
<223> OTHER INFORMATION: Protected as cyclic ether
<220> FEATURE:
<221> NAME/KEY: MISC_FEATURE
<222> LOCATION: (14)..(14)
<223> OTHER INFORMATION: Protected as trityl
<220> FEATURE:
<221> NAME/KEY: MISC_FEATURE
<222> LOCATION: (17)..(17)
<223> OTHER INFORMATION: Protected as trityl

<400> SEQUENCE: 50

Ile Phe Ile Ala Ser Lys Lys Val Thr Cys Ser Leu Ser Asn Leu Ile
1               5                   10                  15

Cys Leu Ile

<210> SEQ ID NO 51
<211> LENGTH: 13
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (1)..(1)
<223> OTHER INFORMATION: Protected as trityl
<220> FEATURE:
<221> NAME/KEY: MISC_FEATURE
<222> LOCATION: (2)..(2)
<223> OTHER INFORMATION: Protected as trityl
<220> FEATURE:
<221> NAME/KEY: MISC_FEATURE
<222> LOCATION: (3)..(3)
```

```
<223> OTHER INFORMATION: Protected as N-Boc
<220> FEATURE:
<221> NAME/KEY: MISC_FEATURE
<222> LOCATION: (4)..(4)
<223> OTHER INFORMATION: Protected as t-butyl
<220> FEATURE:
<221> NAME/KEY: MISC_FEATURE
<222> LOCATION: (5)..(5)
<223> OTHER INFORMATION: Protected as Mmt
<220> FEATURE:
<221> NAME/KEY: MISC_FEATURE
<222> LOCATION: (6)..(6)
<223> OTHER INFORMATION: Protected as t-butyl
<220> FEATURE:
<221> NAME/KEY: MISC_FEATURE
<222> LOCATION: (7)..(7)
<223> OTHER INFORMATION: Protected as Pbf
<220> FEATURE:
<221> NAME/KEY: MISC_FEATURE
<222> LOCATION: (9)..(9)
<223> OTHER INFORMATION: Protected as Mmt
<220> FEATURE:
<221> NAME/KEY: MISC_FEATURE
<222> LOCATION: (10)..(10)
<223> OTHER INFORMATION: Protected as N-Boc
<220> FEATURE:
<221> NAME/KEY: MISC_FEATURE
<222> LOCATION: (11)..(11)
<223> OTHER INFORMATION: Protected as t-butyl ester

<400> SEQUENCE: 51

Gln Asn Lys Cys Cys Ser Arg Leu Ser Lys Asp Leu Leu
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (2)..(2)
<223> OTHER INFORMATION: Protected as trityl
<220> FEATURE:
<221> NAME/KEY: MISC_FEATURE
<222> LOCATION: (3)..(3)
<223> OTHER INFORMATION: Protected as N-Boc
<220> FEATURE:
<221> NAME/KEY: MISC_FEATURE
<222> LOCATION: (4)..(4)
<223> OTHER INFORMATION: Functionalized with S-tert-butyl
<220> FEATURE:
<221> NAME/KEY: MISC_FEATURE
<222> LOCATION: (5)..(5)
<223> OTHER INFORMATION: Protected as Mmt
<220> FEATURE:
<221> NAME/KEY: MISC_FEATURE
<222> LOCATION: (6)..(6)
<223> OTHER INFORMATION: Protected as t-butyl ether
<220> FEATURE:
<221> NAME/KEY: MISC_FEATURE
<222> LOCATION: (7)..(7)
<223> OTHER INFORMATION: Protected as Pbf
<220> FEATURE:
<221> NAME/KEY: MISC_FEATURE
<222> LOCATION: (9)..(9)
<223> OTHER INFORMATION: Protected as Mmt
<220> FEATURE:
<221> NAME/KEY: MISC_FEATURE
<222> LOCATION: (10)..(10)
<223> OTHER INFORMATION: Protected as N-Boc
<220> FEATURE:
<221> NAME/KEY: MISC_FEATURE
<222> LOCATION: (11)..(11)
<223> OTHER INFORMATION: Protected as t-butyl ester
```

```
<400> SEQUENCE: 52

Gln Asn Lys Cys Cys Ser Arg Leu Ser Lys Asp Leu Leu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (2)..(2)
<223> OTHER INFORMATION: Protected as trityl
<220> FEATURE:
<221> NAME/KEY: MISC_FEATURE
<222> LOCATION: (3)..(3)
<223> OTHER INFORMATION: Protected as N-Boc
<220> FEATURE:
<221> NAME/KEY: MISC_FEATURE
<222> LOCATION: (4)..(4)
<223> OTHER INFORMATION: Protected as t-butyl ether
<220> FEATURE:
<221> NAME/KEY: MISC_FEATURE
<222> LOCATION: (5)..(5)
<223> OTHER INFORMATION: Protected as Mmt
<220> FEATURE:
<221> NAME/KEY: MISC_FEATURE
<222> LOCATION: (6)..(6)
<223> OTHER INFORMATION: Protected as t-butyl ether
<220> FEATURE:
<221> NAME/KEY: MISC_FEATURE
<222> LOCATION: (7)..(7)
<223> OTHER INFORMATION: Protected as Pbf
<220> FEATURE:
<221> NAME/KEY: MISC_FEATURE
<222> LOCATION: (9)..(9)
<223> OTHER INFORMATION: Protected as Mmt
<220> FEATURE:
<221> NAME/KEY: MISC_FEATURE
<222> LOCATION: (10)..(10)
<223> OTHER INFORMATION: Protected as N-Boc
<220> FEATURE:
<221> NAME/KEY: MISC_FEATURE
<222> LOCATION: (11)..(11)
<223> OTHER INFORMATION: Protected as t-butyl ester

<400> SEQUENCE: 53

Gln Asn Lys Cys Cys Ser Arg Leu Ser Lys Asp Leu Leu
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic bisthioether peptide
<220> FEATURE:
<221> NAME/KEY: MISC_FEATURE
<222> LOCATION: (2)..(2)
<223> OTHER INFORMATION: Protected as trityl
<220> FEATURE:
<221> NAME/KEY: MISC_FEATURE
<222> LOCATION: (3)..(3)
<223> OTHER INFORMATION: Protected as N-Boc
<220> FEATURE:
<221> NAME/KEY: MISC_FEATURE
<222> LOCATION: (4)..(4)
<223> OTHER INFORMATION: Functionalized as S-tert-butyl
<220> FEATURE:
<221> NAME/KEY: MISC_FEATURE
<222> LOCATION: (5)..(5)
<223> OTHER INFORMATION: Protected as Mmt
<220> FEATURE:
<221> NAME/KEY: MISC_FEATURE
```

```
<222> LOCATION: (6)..(6)
<223> OTHER INFORMATION: Protected as t-butyl ether
<220> FEATURE:
<221> NAME/KEY: MISC_FEATURE
<222> LOCATION: (7)..(7)
<223> OTHER INFORMATION: Protected as Pbf
<220> FEATURE:
<221> NAME/KEY: MISC_FEATURE
<222> LOCATION: (9)..(9)
<223> OTHER INFORMATION: Protected as Mmt
<220> FEATURE:
<221> NAME/KEY: MISC_FEATURE
<222> LOCATION: (10)..(10)
<223> OTHER INFORMATION: Protected as N-Boc
<220> FEATURE:
<221> NAME/KEY: MISC_FEATURE
<222> LOCATION: (11)..(11)
<223> OTHER INFORMATION: Protected as t-butyl ester

<400> SEQUENCE: 54

Gln Asn Lys Cys Cys Ser Arg Leu Ser Lys Asp Leu Leu
1               5                   10

<210> SEQ ID NO 55
<211> LENGTH: 19
<212> TYPE: PRT
<213> ORGANISM: Artificial Sequence
<220> FEATURE:
<223> OTHER INFORMATION: Synthetic bisthioether peptide, Compound S10
<220> FEATURE:
<221> NAME/KEY: MISC_FEATURE
<222> LOCATION: (1)..(1)
<223> OTHER INFORMATION: Protected as t-butyl ether
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (4)..(4)
<223> OTHER INFORMATION: Protected as Mmt
<220> FEATURE:
<221> NAME/KEY: MISC_FEATURE
<222> LOCATION: (7)..(7)
<223> OTHER INFORMATION: Protected as t-butyl ether
<220> FEATURE:
<221> NAME/KEY: MISC_FEATURE
<222> LOCATION: (10)..(10)
<223> OTHER INFORMATION: Protected as t-butyl ether
<220> FEATURE:
<221> NAME/KEY: MISC_FEATURE
<222> LOCATION: (11)..(11)
<223> OTHER INFORMATION: Functionalized as S-tert-butyl
<220> FEATURE:
<221> NAME/KEY: MISC_FEATURE
<222> LOCATION: (14)..(14)
<223> OTHER INFORMATION: Protected as t-butyl ester
```

```
<220> FEATURE:
<221> NAME/KEY: MISC_FEATURE
<222> LOCATION: (15)..(15)
<223> OTHER INFORMATION: Functionalized as S-tert-butyl
<220> FEATURE:
<221> NAME/KEY: MISC_FEATURE
<222> LOCATION: (18)..(18)
<223> OTHER INFORMATION: Functionalized as trityl
<220> FEATURE:
<221> NAME/KEY: MISC_FEATURE
<222> LOCATION: (19)..(19)
<223> OTHER INFORMATION: Functionalized as trityl

<400> SEQUENCE: 55

Thr Val Asp Cys Ile Ala Ser Cys Leu Ser Cys Leu Ala Glu Cys Val
1               5                   10                  15

Pro Gln Asn

<210> SEQ ID NO 56
<211> LENGTH: 19
<212> TYPE: PRT
<213> ORGANISM: Artificial Sequence
<220> FEATURE:
<223> OTHER INFORMATION: Synthetic bisthioether peptide, Compound S10
<220> FEATURE:
<221> NAME/KEY: MISC_FEATURE
<222> LOCATION: (1)..(1)
<223> OTHER INFORMATION: Protected as t-butyl ether
<220> FEATURE:
<221> NAME/KEY: MISC_FEATURE
<222> LOCATION: (3)..(3)
<223> OTHER INFORMATION: Protected as t-butyl ester
<220> FEATURE:
<221> NAME/KEY: MISC_FEATURE
<222> LOCATION: (4)..(4)
<223> OTHER INFORMATION: Protected as Mmt
<220> FEATURE:
<221> NAME/KEY: MISC_FEATURE
<222> LOCATION: (7)..(7)
<223> OTHER INFORMATION: Protected as t-butyl ether
<220> FEATURE:
<221> NAME/KEY: MISC_FEATURE
<222> LOCATION: (10)..(10)
<223> OTHER INFORMATION: Protected as t-butyl ether
<220> FEATURE:
<221> NAME/KEY: MISC_FEATURE
<222> LOCATION: (14)..(14)
<223> OTHER INFORMATION: Protected as t-butyl ester
<220> FEATURE:
<221> NAME/KEY: MISC_FEATURE
<222> LOCATION: (18)..(18)
<223> OTHER INFORMATION: Protected as trityl
<220> FEATURE:
<221> NAME/KEY: MISC_FEATURE
<222> LOCATION: (19)..(19)
<223> OTHER INFORMATION: Protected as trityl

<400> SEQUENCE: 56

Thr Val Asp Cys Ile Ala Ser Cys Leu Ser Cys Leu Ala Glu Cys Val
1               5                   10                  15

Pro Gln Asn
```

BIS-THIOETHER STAPLED PEPTIDES AS INHIBITORS OF PRC2 FUNCTION

CROSS-REFERENCE TO RELATED APPLICATIONS

This application is a non-provisional of, and claims priority to, U.S. Patent Application 62/900,964 (filed Sep. 16, 2019), the entirety of which is incorporated herein by reference.

STATEMENT OF FEDERALLY SPONSORED RESEARCH OR DEVELOPMENT

This invention was made with government support under grant numbers SC2GM111231 and 1SC1GM136635-01 awarded by the National Science Foundation. The government has certain rights in the invention.

REFERENCE TO A SEQUENCE LISTING

This application contains a Sequence Listing in computer readable form. The computer readable form is incorporated herein by reference.

BACKGROUND OF THE INVENTION

Polycomb group proteins (PcG) are transcriptional repressors that bind the promoters of genes encoding proteins with key roles in multicellular growth, stem cell biology and neoplastic development. These proteins form large multimeric complexes of two general types, PRC1 and PRC2. PRC2 is involved in the initiation of gene repression and it has intrinsic histone methyltransferase activity, with specificity for lysine 27 of histone H3 (H3K27), whereas PRC1 is important for effecting transcriptional repression. The catalytic activity of PRC2 is conferred by the SET domain of EZH2 in mammals, and also to the other subunits of the core complex; the zinc-finger containing Suz12, and the WD40 repeat proteins EED and RbAp48. These core PRC2 proteins are strongly linked to tumorigenesis, poor prognosis and tumor proliferation. Thus, targeting them for the inactivation of the PRC2 complex has emerged as a high-priority strategy in the field of cancer epigenetics.

The potential of targeting PRC2 complex function for the treatment PCR2-dependent human cancers have been extensively demonstrated. Indeed, several inhibitors of the catalytic SET domain of EZH2 are currently undergoing human phase 1/2 clinical trials. Unfortunately, recent reports indicate that extended dosing of these drugs leads to secondary EZH2 mutants resistant to treatment. An improved inhibitor is therefore desired.

The discussion above is merely provided for general background information and is not intended to be used as an aid in determining the scope of the claimed subject matter.

SUMMARY

This disclosure describes three novel bisthioether stapled peptides as allosteric inhibitors of Polycomb Repressive Complex 2 (PRC2) catalytic function with demonstrated cell permeability, potent activity in physiological conditions, and strong antiproliferative effects on cancer cells. These inhibitors target, for the first time, two protein interfaces in PRC2 that are crucial for its proper assembling and thus for its histone methyltransferase activity.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 2A depicts the results of biochemical assays showing structure of the synthesized stapled peptides, and their correspondent helicity and $IC_{50}$ values for inhibition of H3K27 trimethylation in vitro, as determined by a histone methyltransferase colorimetric assay optimized using endogenous PRC2 extracted from a human clear cell renal carcinoma cell line (Caki-1);

FIG. 4A, FIG. 4B, FIG. 4C and FIG. 4D depict a synthetic scheme for the preparation of single turn stapled peptides (i, i+4) mimetics of the SUZ12-VEFS domain, residues 590-603, as inhibitors of PRC2 methyltransferase activity;

FIG. 5A shows the structure of the designed stapled peptides and summary of results obtained in the biochemical assays;

FIG. 8A shows the structure and helicity of all the synthesized stapled peptides;

DETAILED DESCRIPTION OF THE INVENTION

Figure 1A:
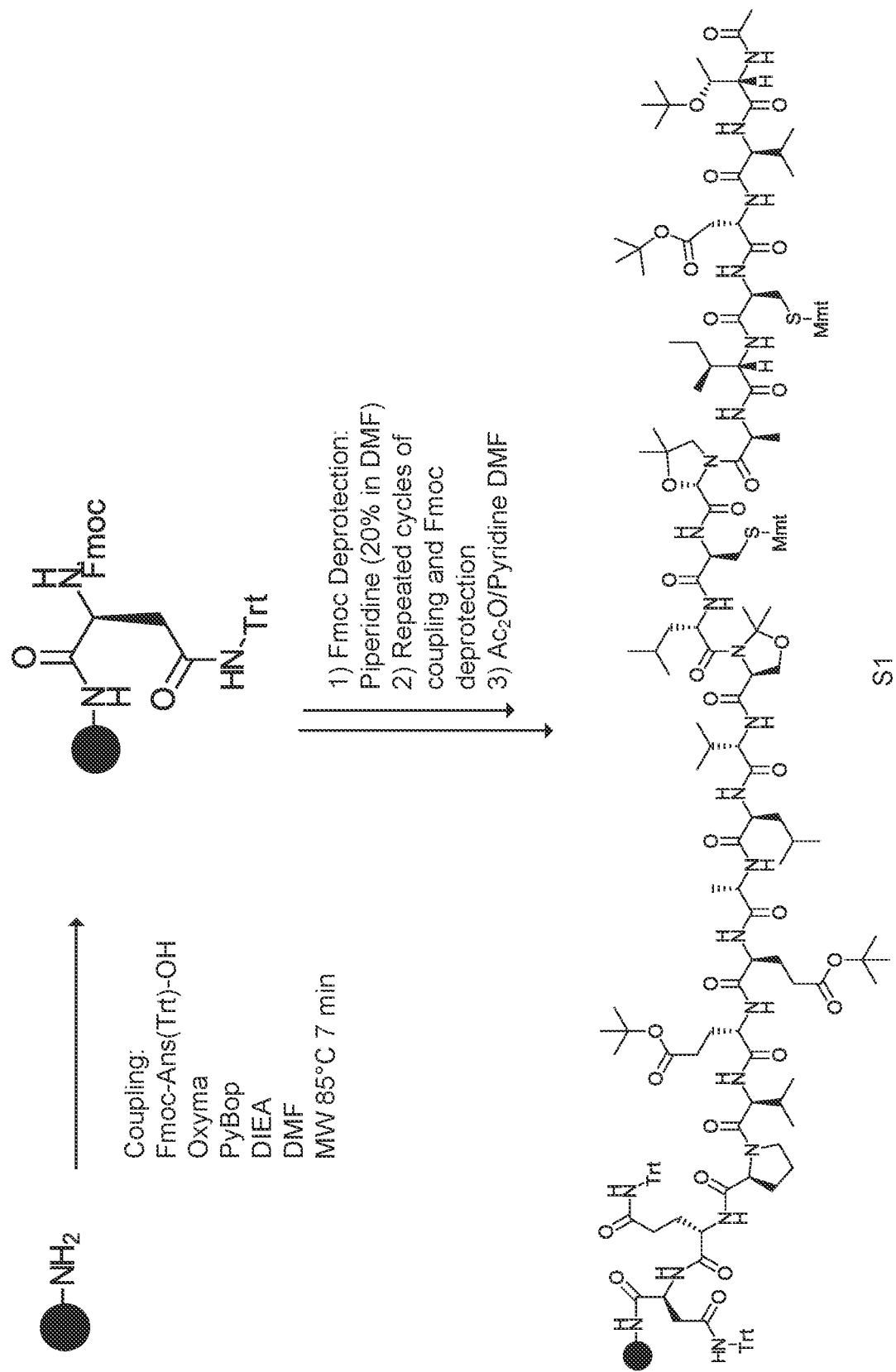
FIG. 1A, FIG. 1B and FIG. 1C depict a synthetic scheme for the chemoselective preparation of single turn stapled peptides (i,i+4) inhibitors of the trimolecular SANT1L-SBD interaction in EZH2.
Figure 1B:
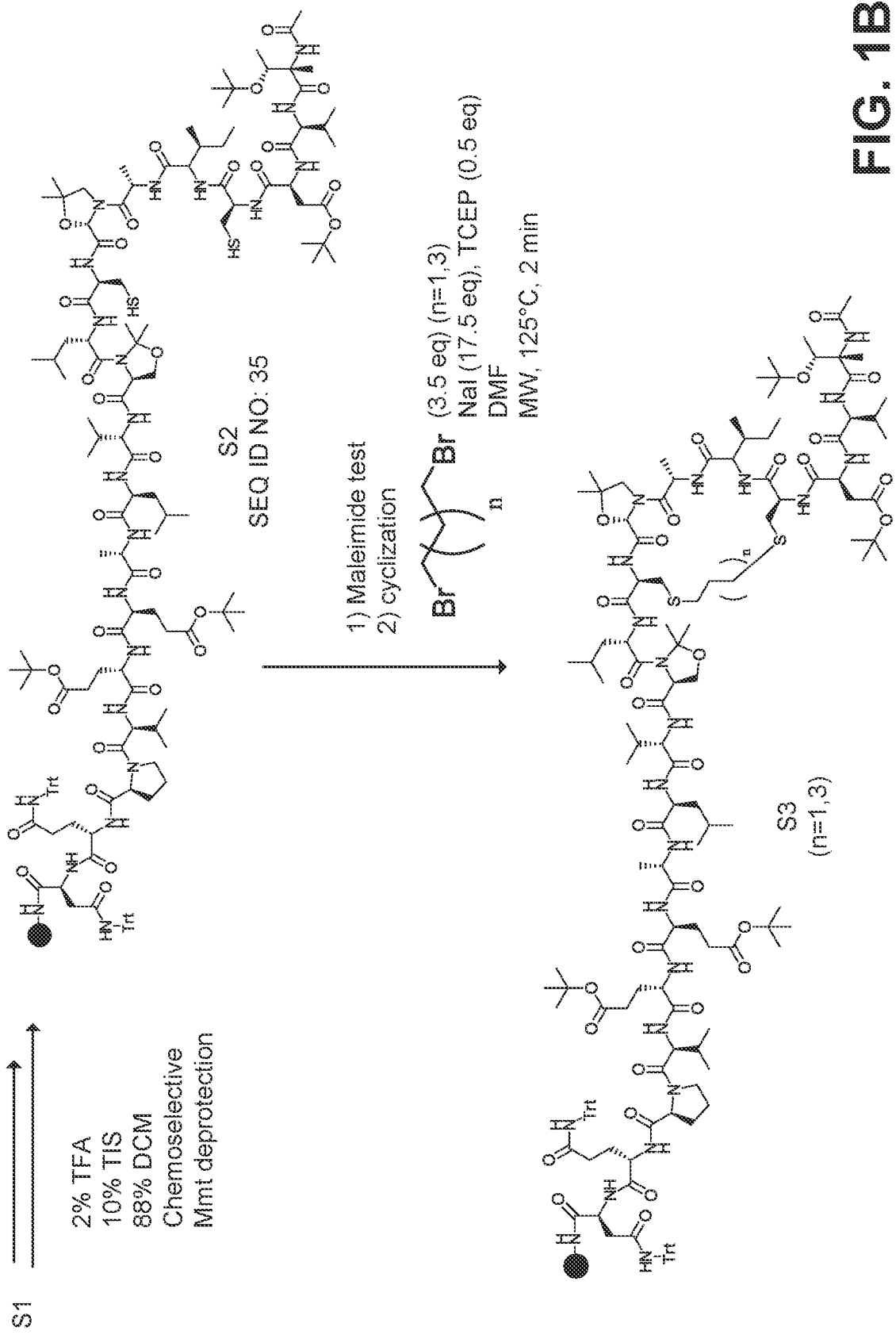
Figure 1C:
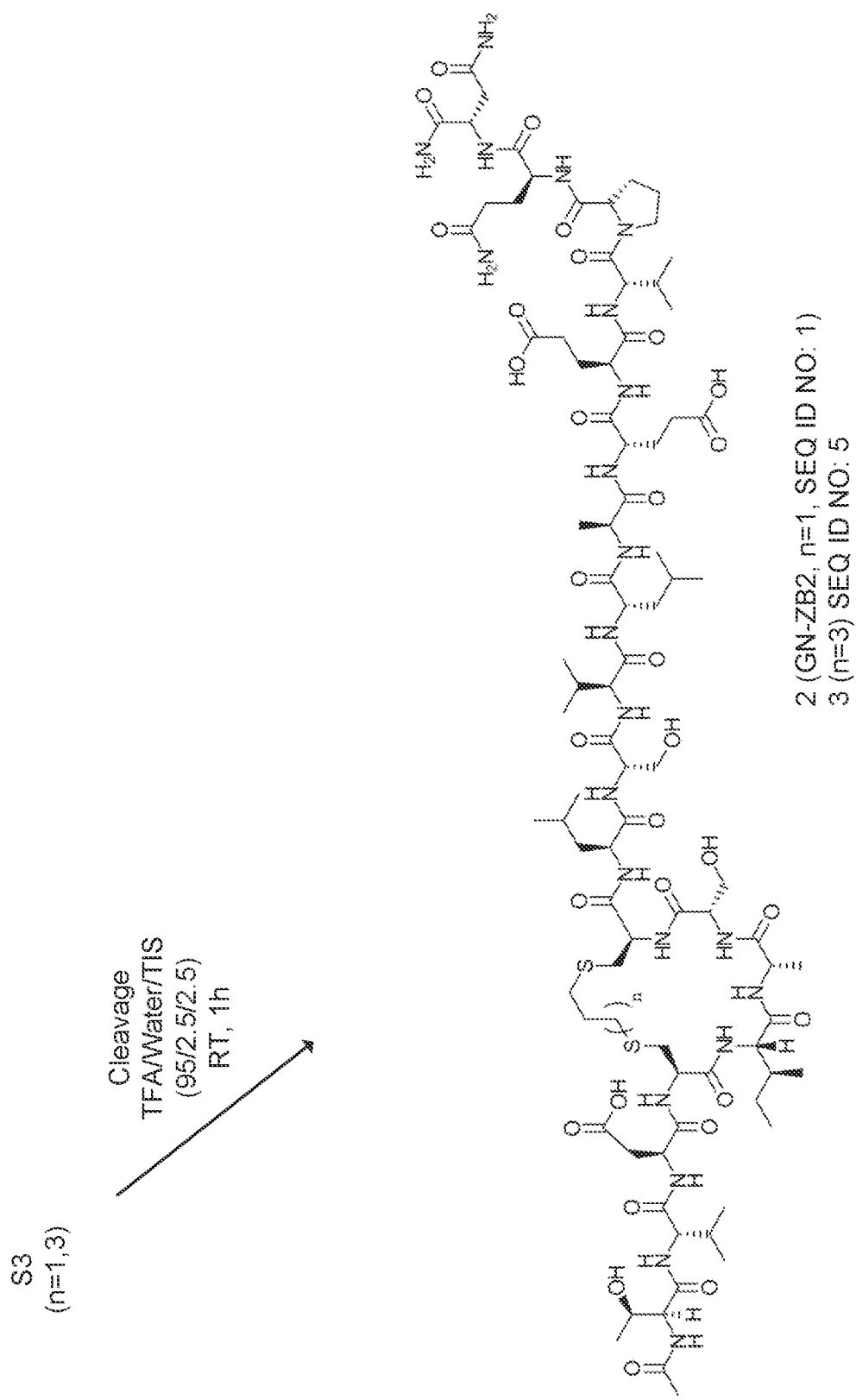
Figure 1D:
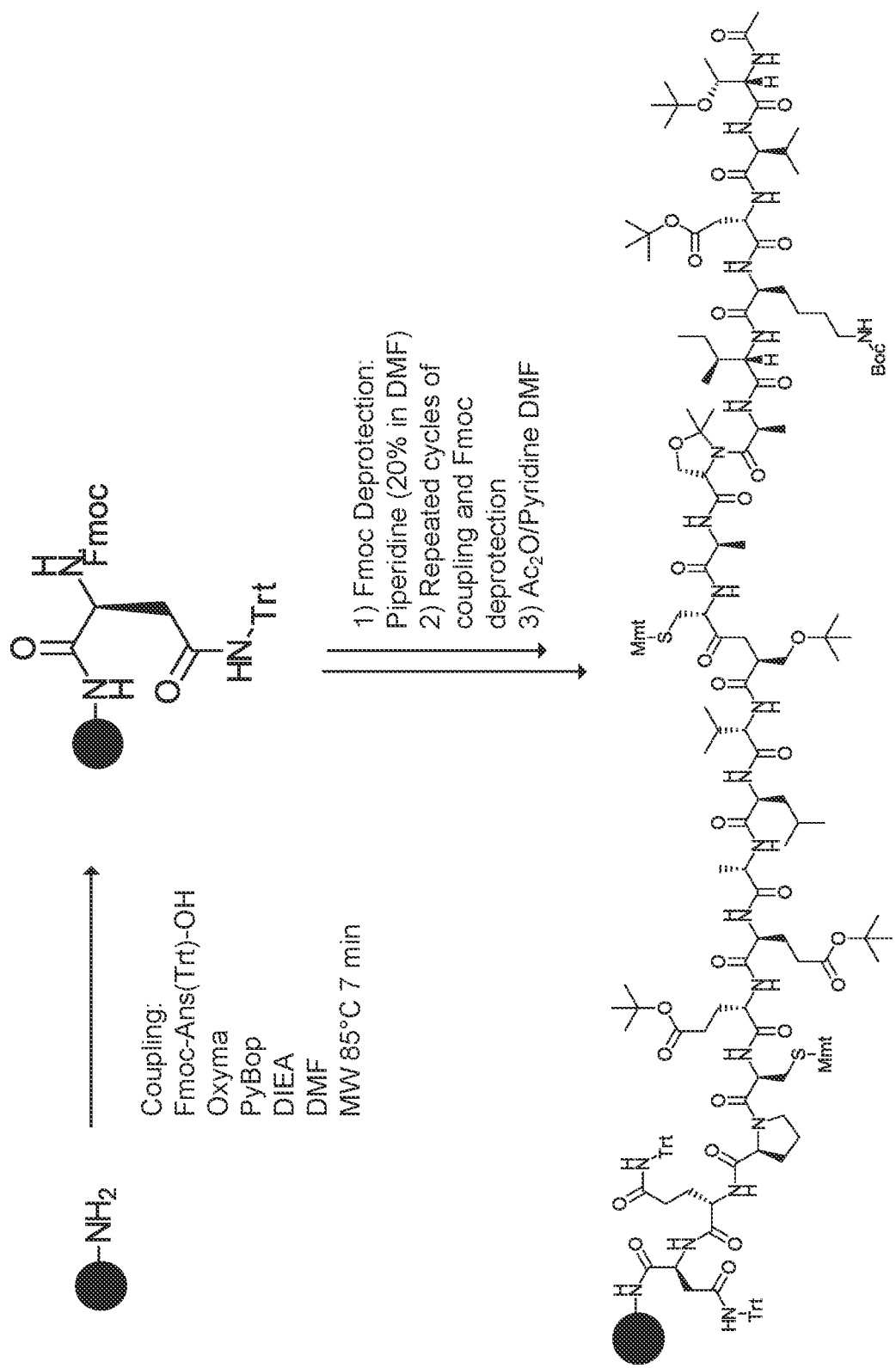
FIG. 1D, FIG. 1E, FIG. 1F and FIG. 1G depict a synthetic scheme for the chemoselective preparation of double turn stapled peptides (i,i+7) inhibitors of the intramolecular SANT1L-SBD interaction in EZH2.
Figure 1E:
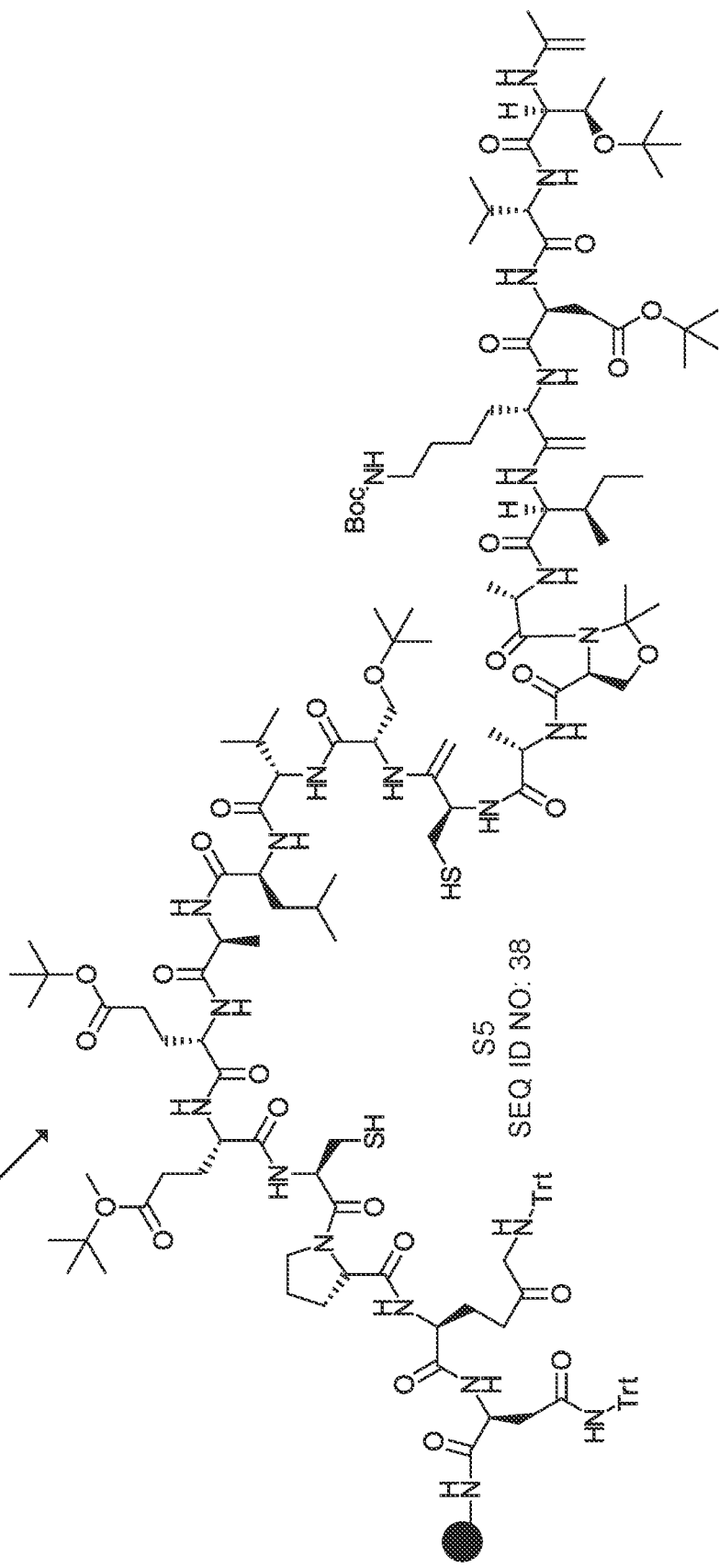
Figure 1F:
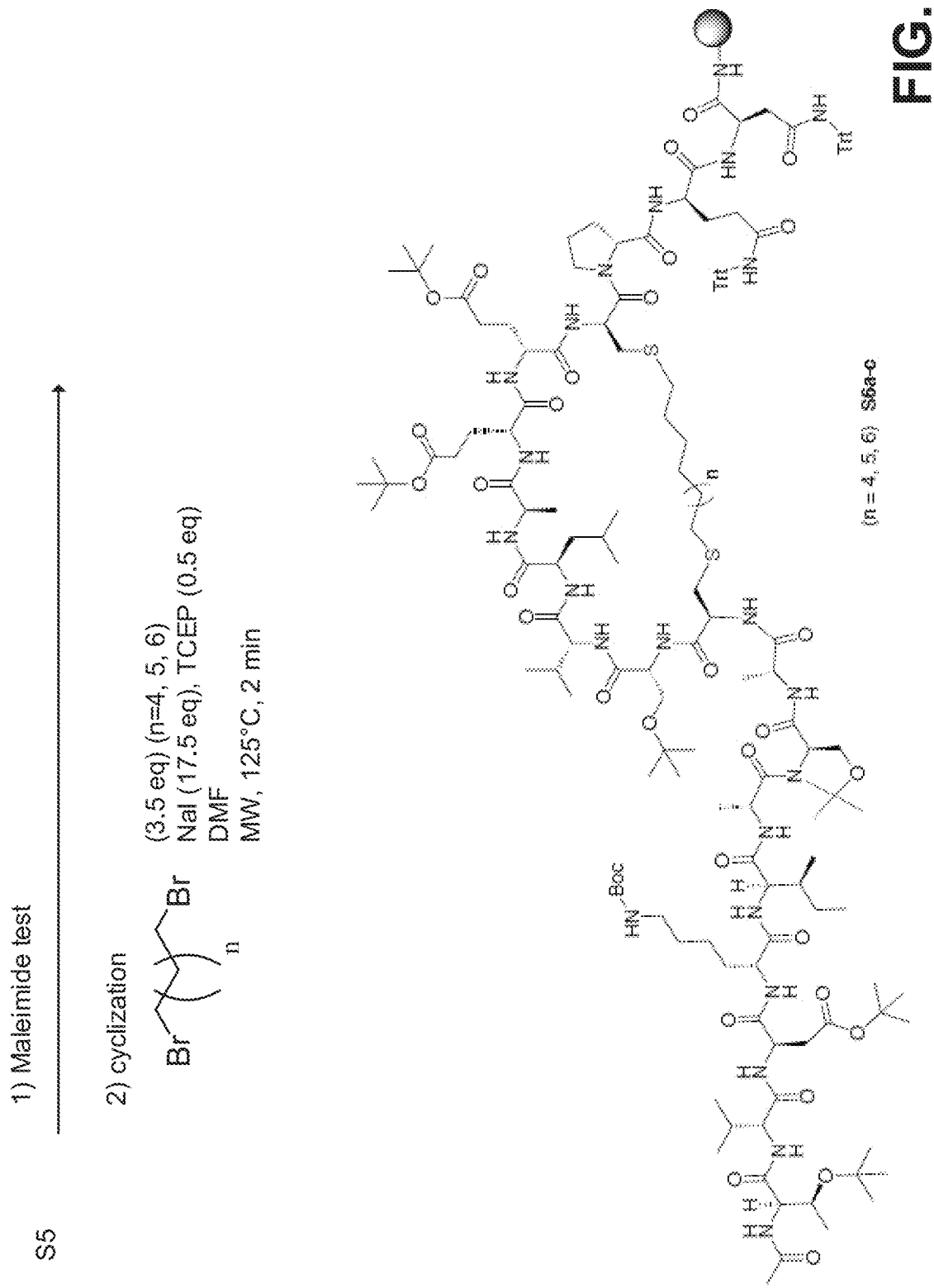
Figure 1G:
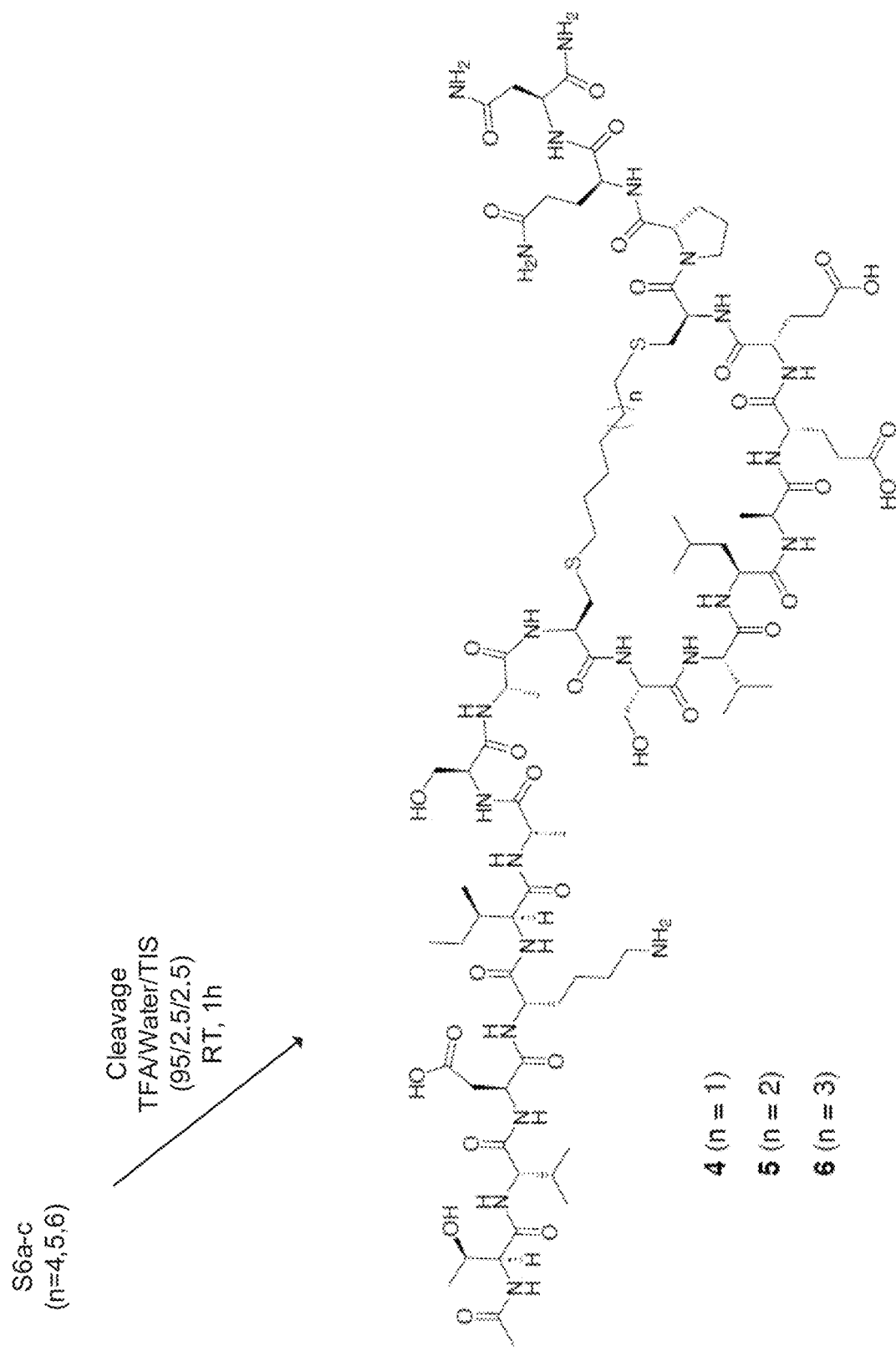

This disclosure describes three novel bisthioether stapled peptides as allosteric inhibitors of Polycomb Repressive Complex 2 (PRC2) catalytic function with demonstrated cell permeability, potent activity in physiological conditions, and strong antiproliferative effects on cancer cells. These inhibitors target, for the first time, two protein interfaces in PRC2 that are crucial for its proper assembling and thus for its histone methyltransferase activity.

This disclosure provides a design, synthesis and biological evaluation of bisthioether stapled peptides inhibitors of the catalytic function of the master of transcriptional regulation EZH2, the catalytic subunit of PRC2 of proteins. PRC2 is responsible for the methylation of lysine 27 on Histone H3, a post-translational modification associated with transcriptional silencing and linked to the development and progression of different types of cancer.

Three families of novel allosteric inhibitors of PRC2 function are disclosed. The first family targets a key intramolecular interaction in EZH2, formed by its SANT1L-like domain and its SANT1L-binding domain (SBD). The second family of cyclopeptides is designed to target another EZH2 domain, SANT2, which stablishes an important interaction with the VEFS domain of SUZ12 (SUZ12-VEFS), another core member of the PRC2 complex. The third family targets an alpha helical interaction between Nurff55 and SUZ12, that plays a key role in the complex recruitment onto nucleosomes and thus in its H3K27 methyltransferase activity. The three families of stapled peptides described herein constitute the first allosteric inhibitors of PRC2 activity targeting such protein interfaces, previously reported to play a crucial role for both the assembly of the complex and its and catalytic function.

The first lead compound, GN-ZB2, has been designed to disrupt a crucial intermolecular interaction in EZH2, the catalytic subunit of PRC2. Remarkably, this cyclopeptide is almost as effective at inhibiting H3K27 trimethylation as GSK126, an EZH2-SET domain inhibitor currently in clinical development, in both in vitro ($IC_{50}$=0.17±0.02 µM) and in cellular assays ($IC_{50}$=0.4±0.2 µM). The compound shows marked synergistic effects when used in combination with GSK126. This data strongly suggests that GNB-SBDC3 inhibits PRC2 catalytic function allosterically, likely by disrupting the key intramolecular SANT1L-SBD interaction in EZH2.

GN-ZB2     TVD[CIASC](CH$_2$)$_3$LSVLAEEVPQN     SEQ ID NO: 1

The second lead compound, GN-ZW11 also targets EZH2, but in this case at its SANT2 domain, which stablishes a crucial intermolecular interaction with SUZ12-VEFS. This compound also shows potent in vitro H3K27me3 inhibition ($IC_{50}$=0.32±0.10 µM), and strong ability to target and functionally block PRC2-mediated H3K27 trimethylation in a human clear cell renal carcinoma cell line (Caki-1, $IC_{50}$=1.04±1.34 µM).

GN-ZW11    LCRN[CMLHC](CH$_2$)$_3$VSMHDFLI     SEQ ID NO: 2

The third lead compound, GN-Z24, has been designed to target an alpha helical interaction between Nurff55 and SUZ12, another two core members of PRC2, that play a key role in the complex recruitment onto nucleosomes and thus in its catalytic activity. More specifically, this compound mimics the helix a1 of Nurf55, which interacts with the NBE (Nurf55 binding epitope) domain of SUZ12. Therefore, GNZ-NSC3 may inhibit PRC2-mediated H3K27 trimethylation by disrupting the crucial S/H-NBE binary complex formed by the interaction of the correspondent Nurf 55 and SUZ12 domains. The potency shown by this compound in both in vitro ($IC_{50}$=1.33±1.36 µM) and cellular assays ($IC_{50}$=2.06±1.26 µM) almost matches that of GSK126 and the GNB-SBDC3 and GNK-SANTC3 cyclopeptides.

GN-Z24     V[CNEEC](CH$_2$)$_3$KIWKKNTPFL     SEQ ID NO: 3

Several small molecule inhibitors of PRC2 function are already in clinical trials. Interestingly, all of them compete with SAM (S-adenosyl methionine) for the catalytic SET domain of EZH2, although their specific binding mode is still unknown. However, recent reports indicate that extended dosing with such small molecules leads to secondary EZH2 mutants that become resistant to treatment. Allosteric PRC2 inhibitors constitute an effective alternative solution to address such resistance profiles. Indeed, the promising potential of this class of compounds has been recently proven with both a potent stapled peptide and two small molecule inhibitors targeting a binding pocket in EED, another PRC2 core member, crucial for its catalytic activity.

The bis-thioether stapled peptides reported herein constitute a new and different class of PRC2 inhibitors. The potency of these compounds, together with their remarkable selectivity for H3K27me3 inhibition, and low cytotoxicity to non-cancerous cells demonstrate these molecule's potential to develop future epigenetic cancer therapies.

GN-ZB2

Using the published crystal structure of an active PRC2 ortholog from yeast, five macrocycles (compounds 2 (GN-ZB2), 3, 4, 5 and 6) were strategically designed and synthesized according to FIG. 1A, FIG. 1B, FIG. 1C, FIG. 1D, FIG. 1E, FIG. 1F and FIG. 1G.

Figure 2B:
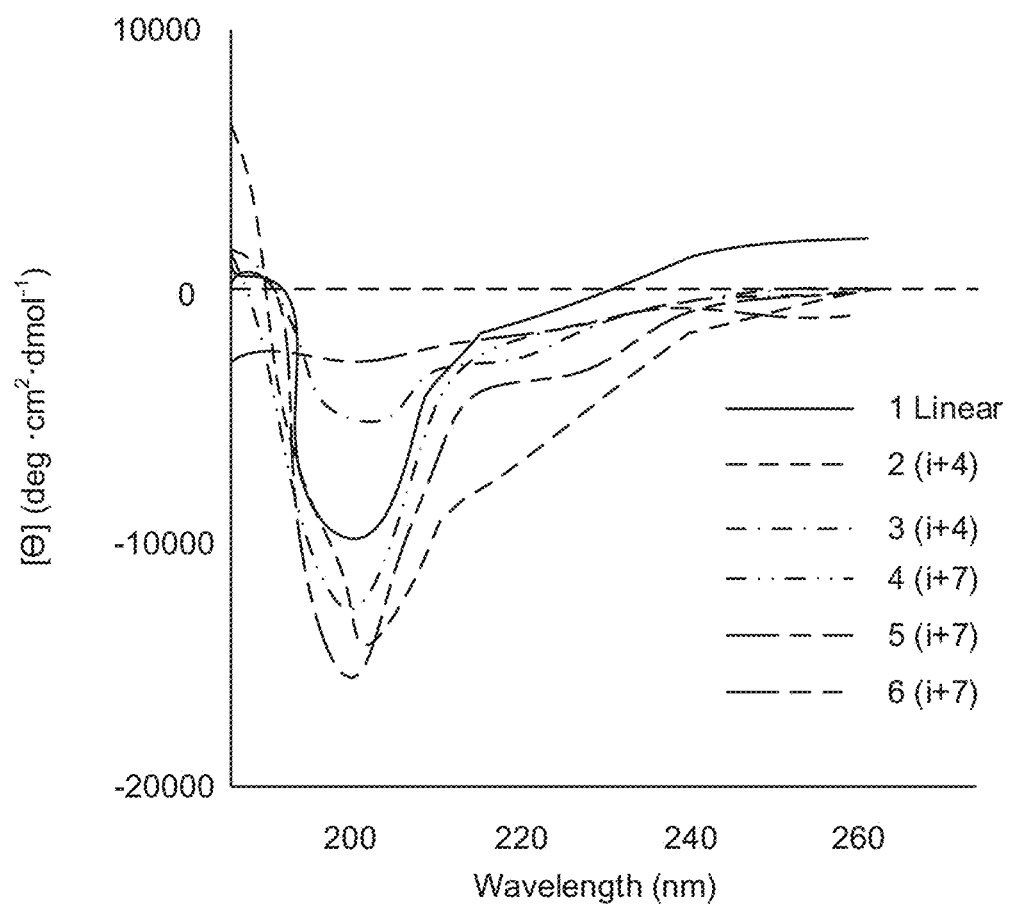
FIG. 2B depicts a CD spectra of stapled peptides and their linear counterparts measured in water at 20° C.

The impact of the staple on the secondary structure of the synthesized macrocycles was investigated by circular dichroism (CD). The analysis of the linear wild type peptide 1 revealed that it was only 4.8% helical in solution, indicating that this sequence is almost disordered when it is removed from the full protein structure. Interestingly, incorporation of the hydrocarbon brace resulted in enhanced helical character for both single- and double-turn stapled peptides. Remarkably, compound 2 (GN-ZB2) showed the best result, with an overall improvement of 18% in helicity (FIG. 2A and FIG. 2B).

Figure 2C:
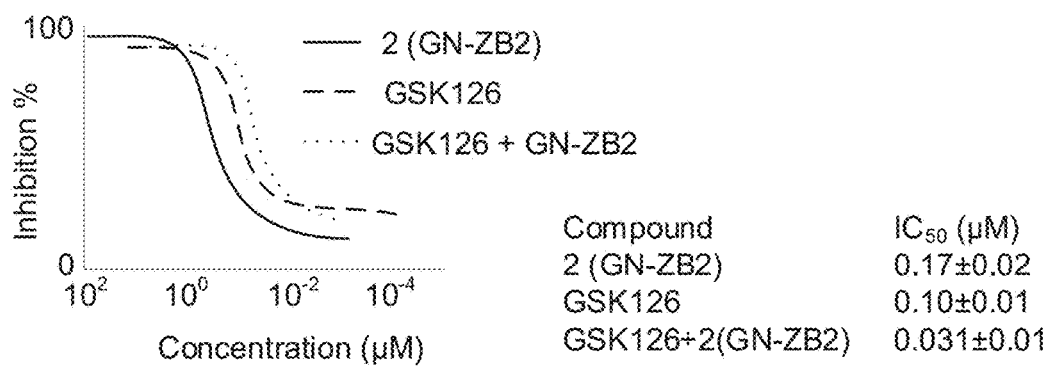
FIG. 2C illustrates a plot of H3K27 trimethylation inhibition using the enzymatic in vitro assay described in FIG. 2A, with varying concentrations of 2 (GN-ZB2), positive control GSK126, and using an equimolar combination of both compounds to test their synergistic effects. A summary of the $IC_{50}$ values for inhibition of H3K27me3 determined from the experiments is also presented. Calculation of the combination index using the equation described by Chou et al. indicated a marked synergistic effect (CI=0.53) of 2 (GN-ZB2) and GSK126.

The cyclopeptides were tested for their ability to inhibit H3K27 trimethylation in vitro. To this end, a histone methyltransferase colorimetric assay was optimized using as catalytic complex endogenous PRC2 extracted from a human clear cell renal carcinoma cell line (Caki-1). A well-characterized EZH2-SET domain inhibitor (GSK126) was used as a positive control for determining optimal assay conditions. Both single- and double-turn stapled peptides showed concentration dependent inhibition of PRC2 catalytic function. In line with the CD data, the best inhibitor was compound 2 (GN-ZB2) with an $IC_{50}$ value of 0.17±0.02 µM. This staple peptide was virtually as potent as GSK126 in the same assay conditions and over 500 times better than its linear wild type counterpart 1 (FIG. 2A). Aiming at gaining insights about the mechanism of action of cyclopeptide 2 (GN-ZB2) for PRC2 inhibition, its potential synergy with the EZH2-SET domain inhibitor GSK126 was explored. The previously optimized enzymatic in vitro assay was performed using an equimolar combination of both compounds. To quantitatively assess synergy, the combination index (CI) equation of Chou et al. was used, for which a value of CI<1 is indicative of a more than additive outcome. Notably, the equimolar mixture of 2 (GN-ZB2)

and GSK126 yielded an IC$_{50}$ value of 0.031±0.001 μM, which corresponded to a CI of 0.53. This data suggest that the compound works synergistically when applied in combination with an inhibitor of the catalytic SET domain of EZH2, and therefore, that it may likely function by blocking a different PRC2 domain, key for its function, i.e, in an allosteric fashion (FIG. 2C).

Figure 2D:
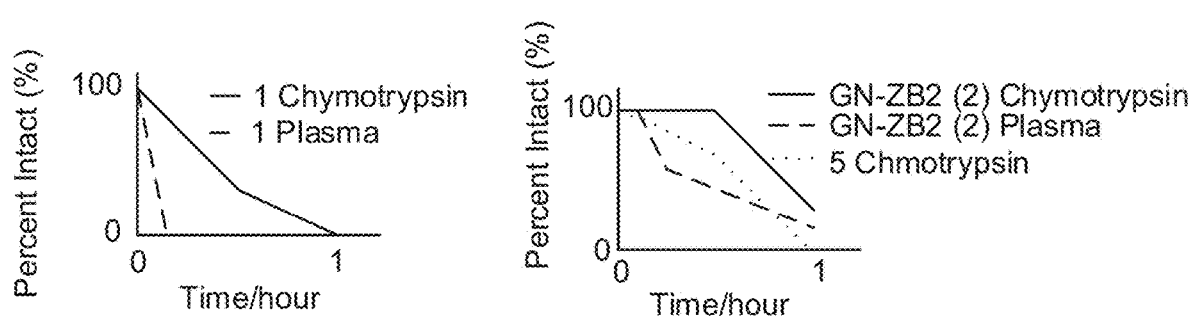
FIG. 2D show both Chymotrypsin-based proteolytic degradation as well as the plasma assay show remarkable stability of the disclosed i, i+4 and i, i+7 12 bisthioether stapled peptides. The rate of peptide proteolysis was monitored by HPLC and HPLC-MS analysis.

The proteolytic stability of these compounds by subjecting two representative examples to a chymotrypsin-based assay previously validated to evaluate the stability of stapled peptides. For comparison, their linear counterparts were also studied. HPLC and LC/MS analysis of the enzymatic reactions showed complete protection of both i+4 and i+7 cyclopeptides against enzymatic degradation after 24h, whereas its linear analogue underwent full hydrolytic cleavage one hour after the reaction started (FIG. 2D). In addition, the stability of cyclopeptide 2 (GN-ZB2) and its parent linear sequence 1 in plasma was tested. In line with the in vitro assay results, the macrocycle showed high resistance to proteolysis in these conditions, resulting also markedly superior to peptide 1, which was fully degraded after 5 minutes (FIG. 2D). Overall, the stapling reaction leads to significant protection against enzymatic degradation, thus making this family of constrained peptides suitable for cellular and biological assays.

Given the encouraging in vitro H3K27me3 inhibition data and the proteolytic stability shown by the stapled peptides, the cellular uptake of compound 2 (GN-ZB2) was explored by confocal microscopy, using an FITC-labeled derivative of it. Confocal imaging after incubation of caki-1 cells with fluorescently-tagged 2 (GN-ZB2-FITC) showed significant membrane translocation of the stapled peptide. More importantly, these experiments also confirmed that this compound is able to reach the nuclei, where the targeted PRC2 complex is localized.

Figure 3A:
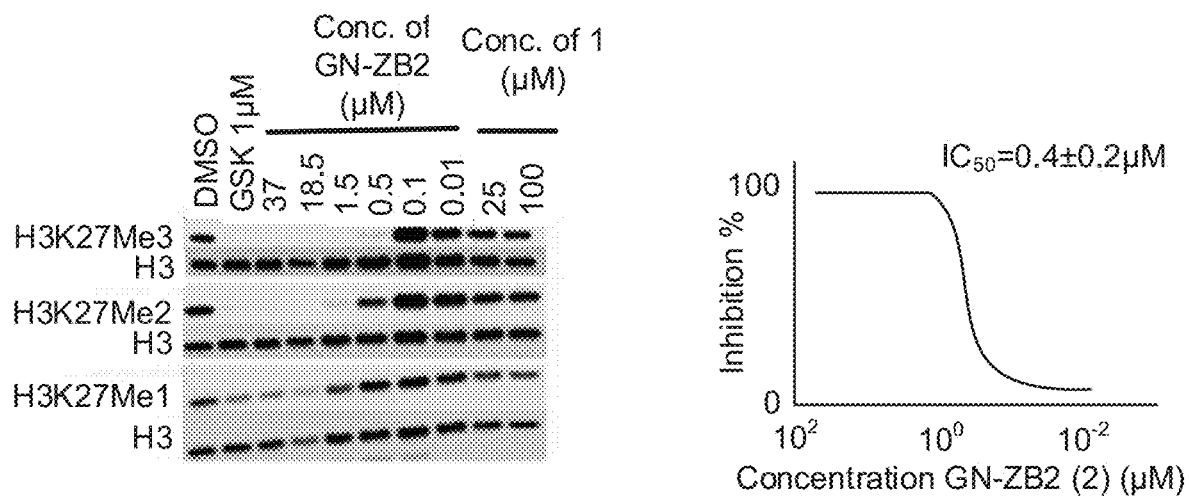
FIG. 3A depicts a Western blot analysis shows dose-dependent response of H3K27me3, H3K27me2 and H3K27me1 within metastatic human clear-cells renal carcinoma cells (Caki-1), after treatment with stapled peptide 2 (GN-ZB2) once daily for 72h. Single concentration treatment with GSK126 (positive control) and linear wild type sequence (1, negative control) in the same experimental conditions are also shown. Quantitation of H3K27me3 using and absorbance-based colorimetric assay yielded an IC50 value of 0.4±0.2 µM. Protein loading was accurately corrected by measuring total H3 using an absorbance-based colorimetric assay.
Figure 3B:
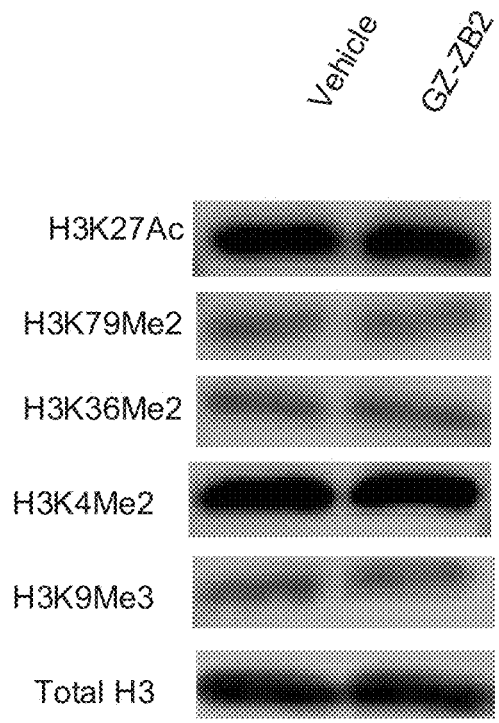
FIG. 3B shows selectivity of H3K27 trimethylation inhibition over a broad panel of histone post-translational modifications. Cells were treated with stapled peptide 2 (GN-ZB2, 5 µM) or vehicle, once daily for 72h.

To further explore the ability of cyclopeptide 2 (GN-ZB2) to target and functionally block PRC2-mediated H3K27 methylation, Caki-1 cells were treated for 72h with varying concentrations of 2 (GN-ZB2) and analyzed all degrees of methylation on K27 by western blot. GSK126 (1 μM) and the linear wild type peptide sequence 1 (25 μM, 100 μM) were used as positive and negative control, respectively. The results showed a clear concentration-dependent inhibition of 2 (GN-ZB2), most pronounced for trimethylation but also significant for H3K27me2 and H3K27 monomethylation (FIG. 3A). Further quantitation of H3K27me3 by an absorbance based colorimetric assay yielded an IC$_{50}$ of 0.4±0.2 μM, similar to that obtained in the in vitro enzymatic functional assay (FIG. 3A). The stapled peptide is cell permeable and a potent inhibitor of relevant physiological methylation of the PRC2 substrate. Remarkably, compound 2 (GN-ZB2) also shows exceptional selectivity for H3K27 trimethylation inhibition. Thus, western blot analysis of histones isolated from cells treated with either high concentration of the cyclopeptide 2 (GN-ZB2, 5 μM) or vehicle control showed no effect on H3K4me3, H3K9me3, H3K36me2, H3K79me2 and H3K27Ac, whereas total inhibition of H3K27me3 was observed in the same experimental conditions (FIG. 3B).

Figure 3C:
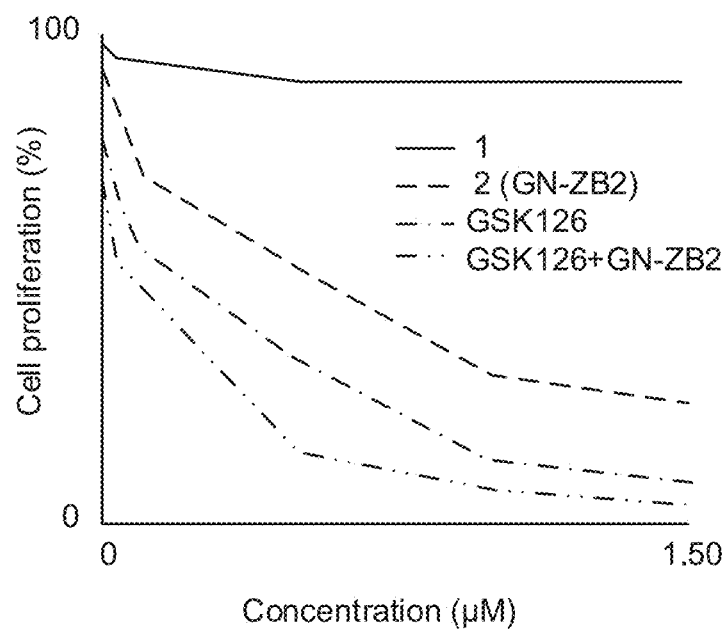
FIG. 3C shows the results of treatment of Caki-1 cells with cyclopeptide 2 (GN-ZB2), control compound GSK126, and an equimolar combination of both molecules significantly inhibits cell proliferation. Proliferation was measured after 72h of daily treatment with the correspondent compound. The data is presented as a mean of two independent experiments each with triplicate measurements.
Figure 3D:
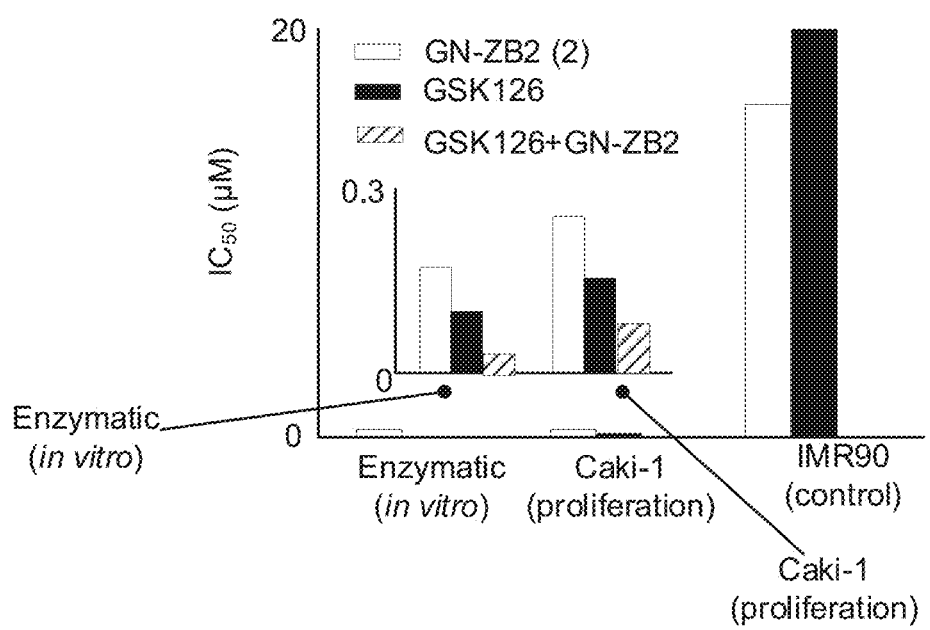
FIG. 3D shows a plot of $IC_{50}$ values obtained when testing compound 2 (GN-ZB2), GSK126 and a combination of both in: (d.1) an enzymatic in vitro assay monitoring H3K27me3 inhibition, using endogenous PRC2 extracted from a human clear cell renal carcinoma cell line (Caki-1), (d.2) a proliferation colorimetric assay with Caki-1 cells, (d.3) in non-cancerous human fibroblast IMR90 cells. Calculation of the combination index using the equation described by Chou et al. indicated a marked synergistic antiproliferative effect (CI=0.61) when both compounds are used together.
Figure 4A:
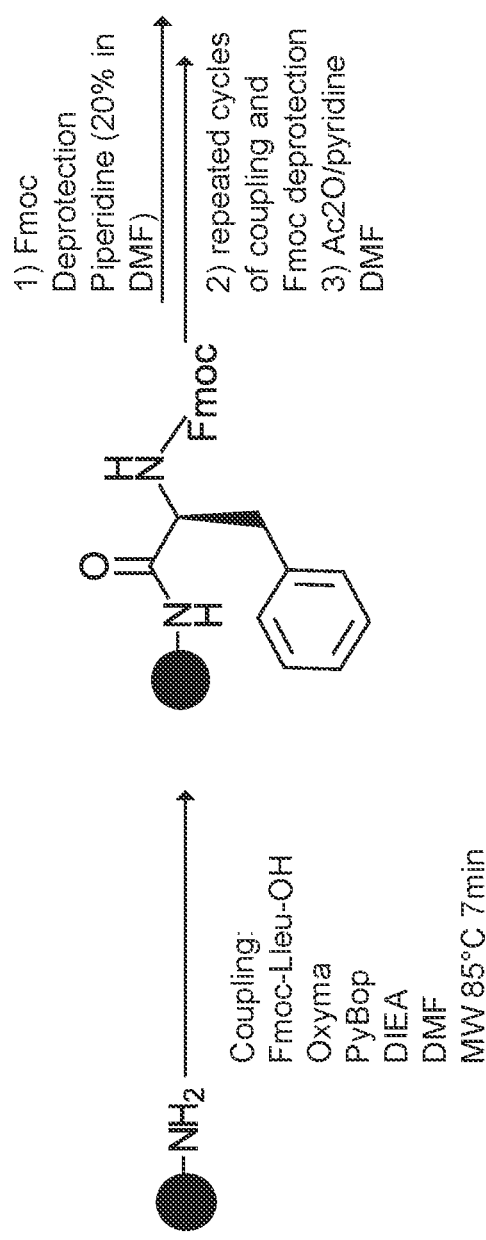
Figure 4A:
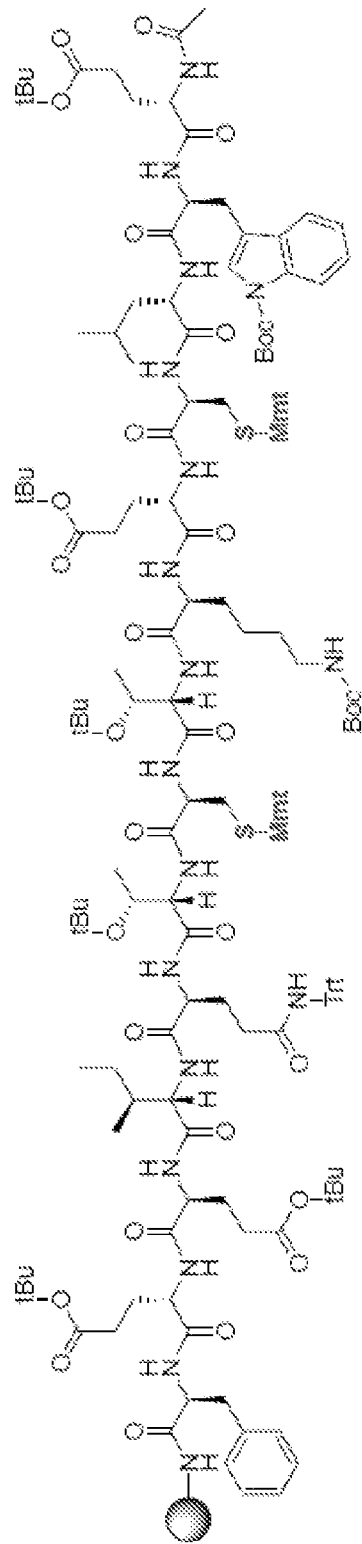
Figure 4B:
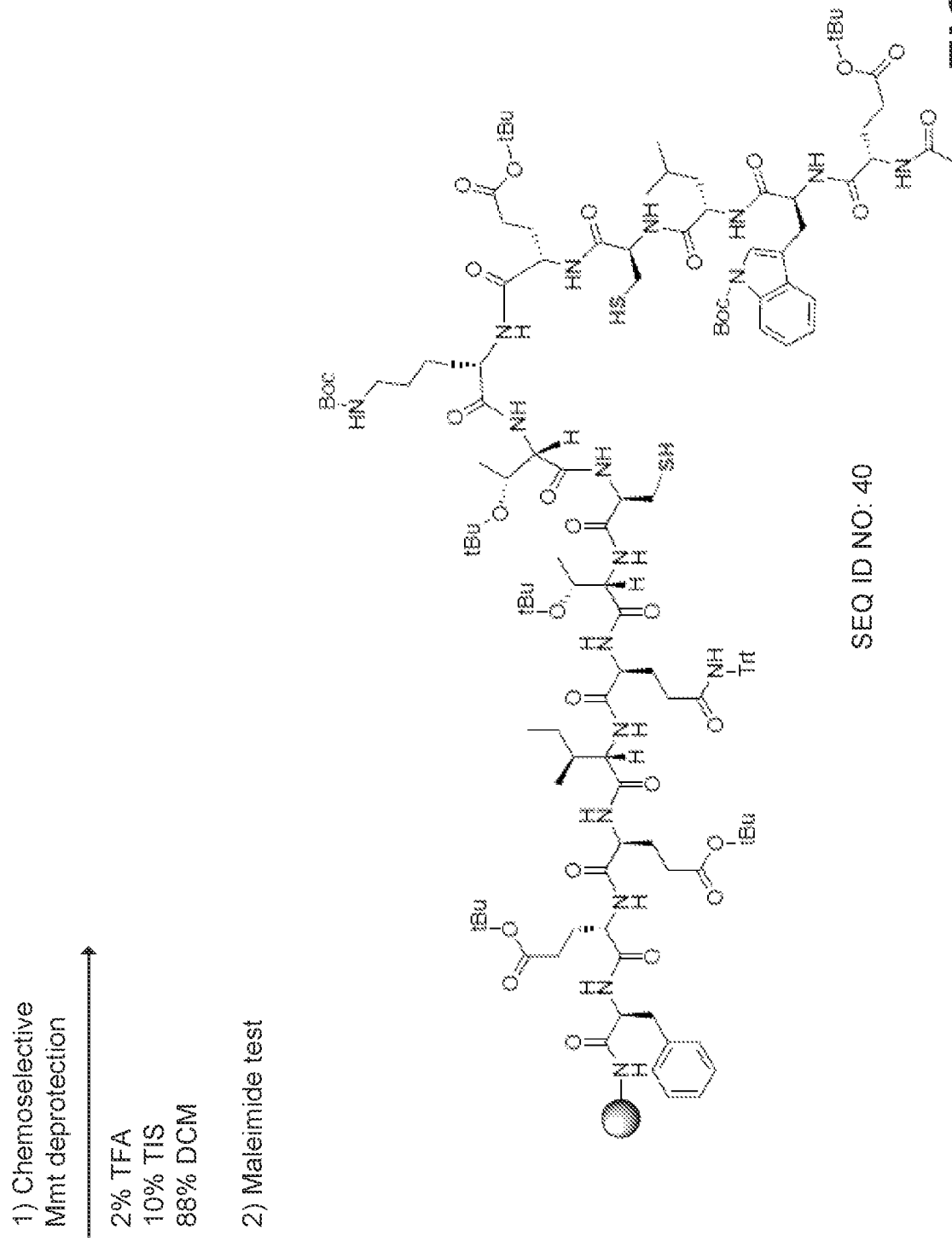
Figure 4C:
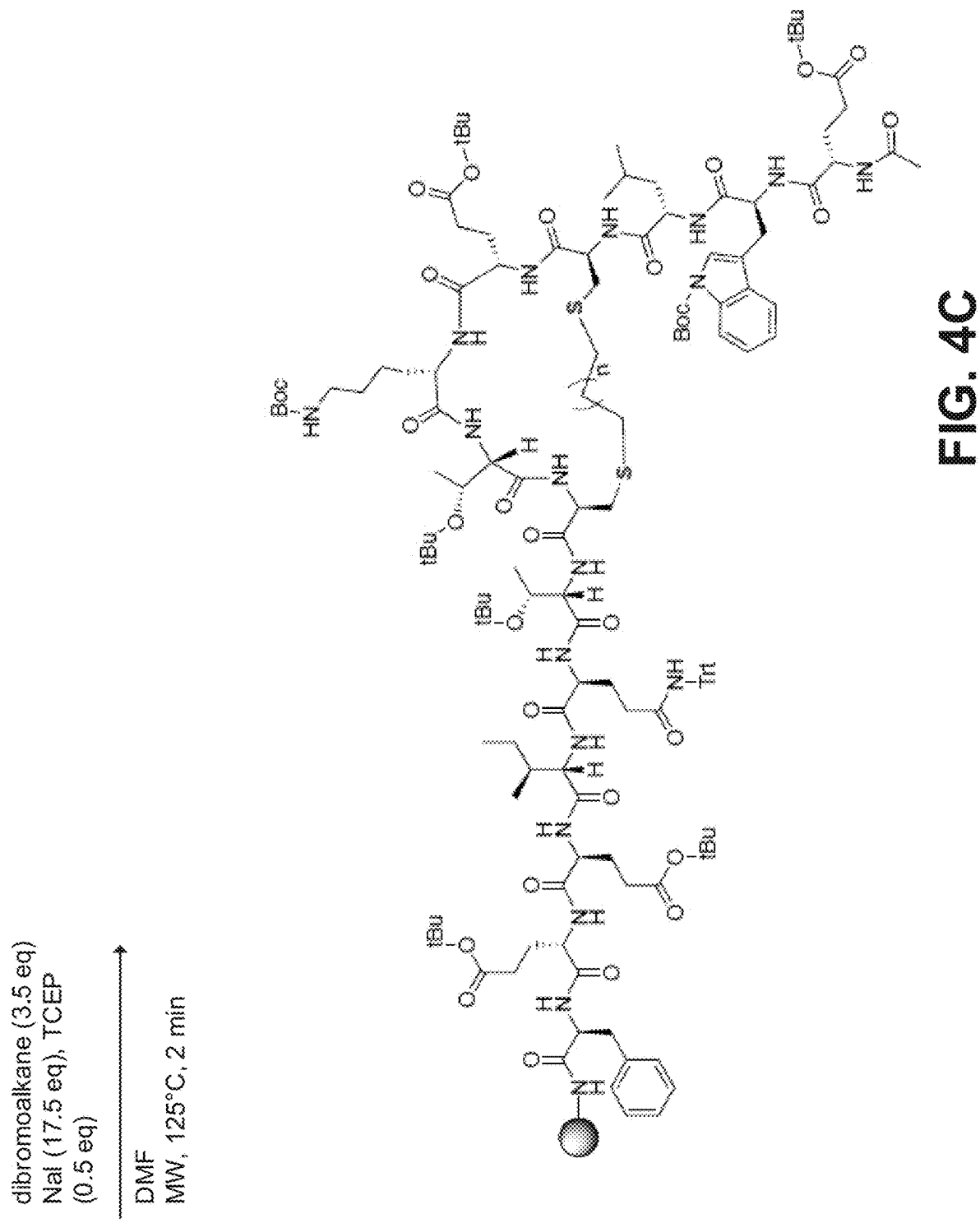
Figure 4E:
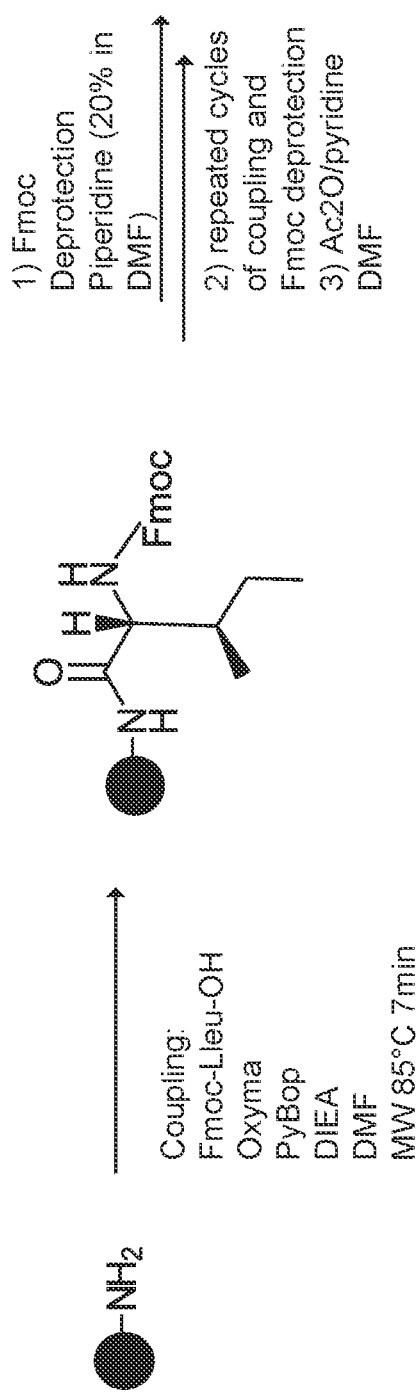
FIG. 4E, FIG. 4F, FIG. 4G, FIG. 4H, FIG. 4I depict a synthetic scheme for the preparation of single turn stapled peptides (i, i+4) mimetics of the SUZ12-VEFS domain, residues 652-669, as inhibitors of PRC2 methyltransferase activity.
Figure 4E:
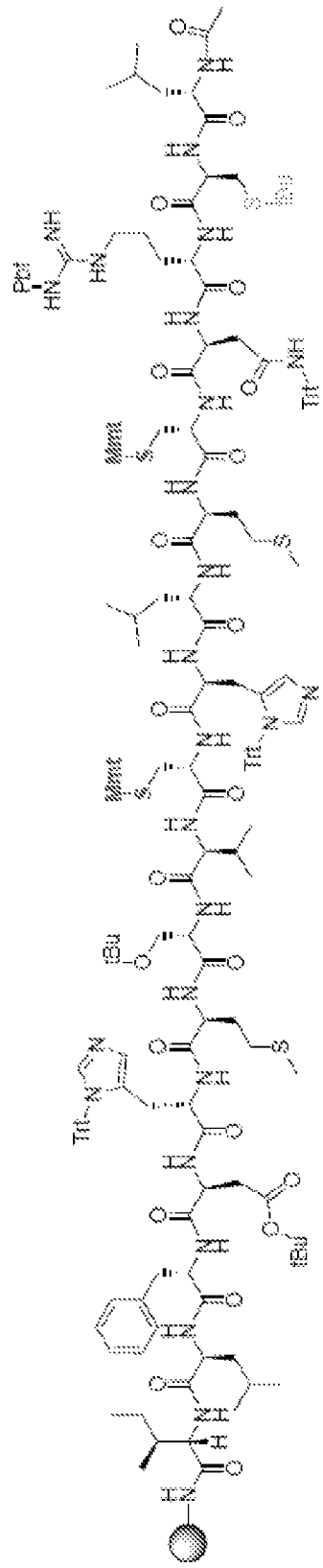
Figure 4F:
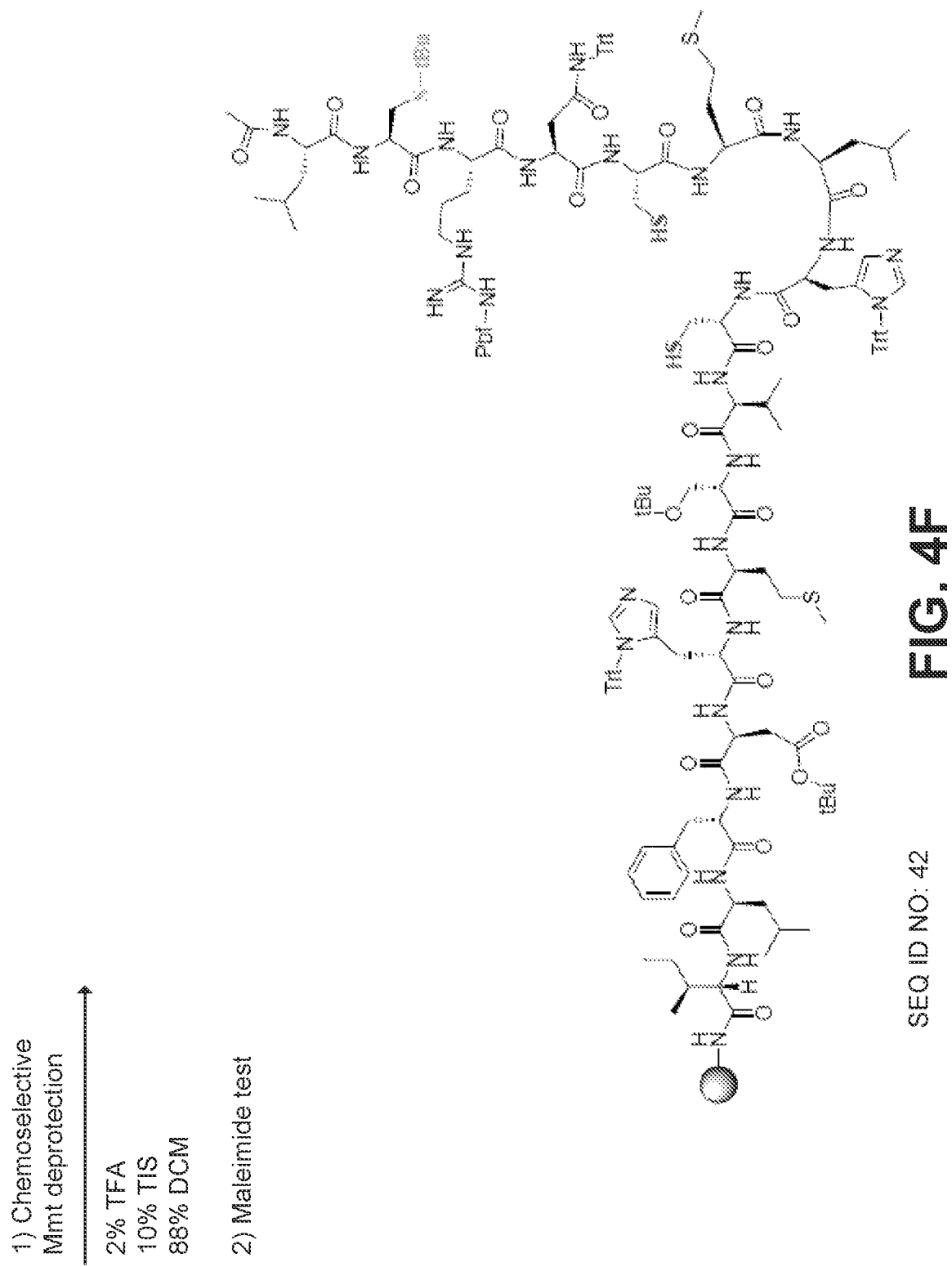
Figure 4G:
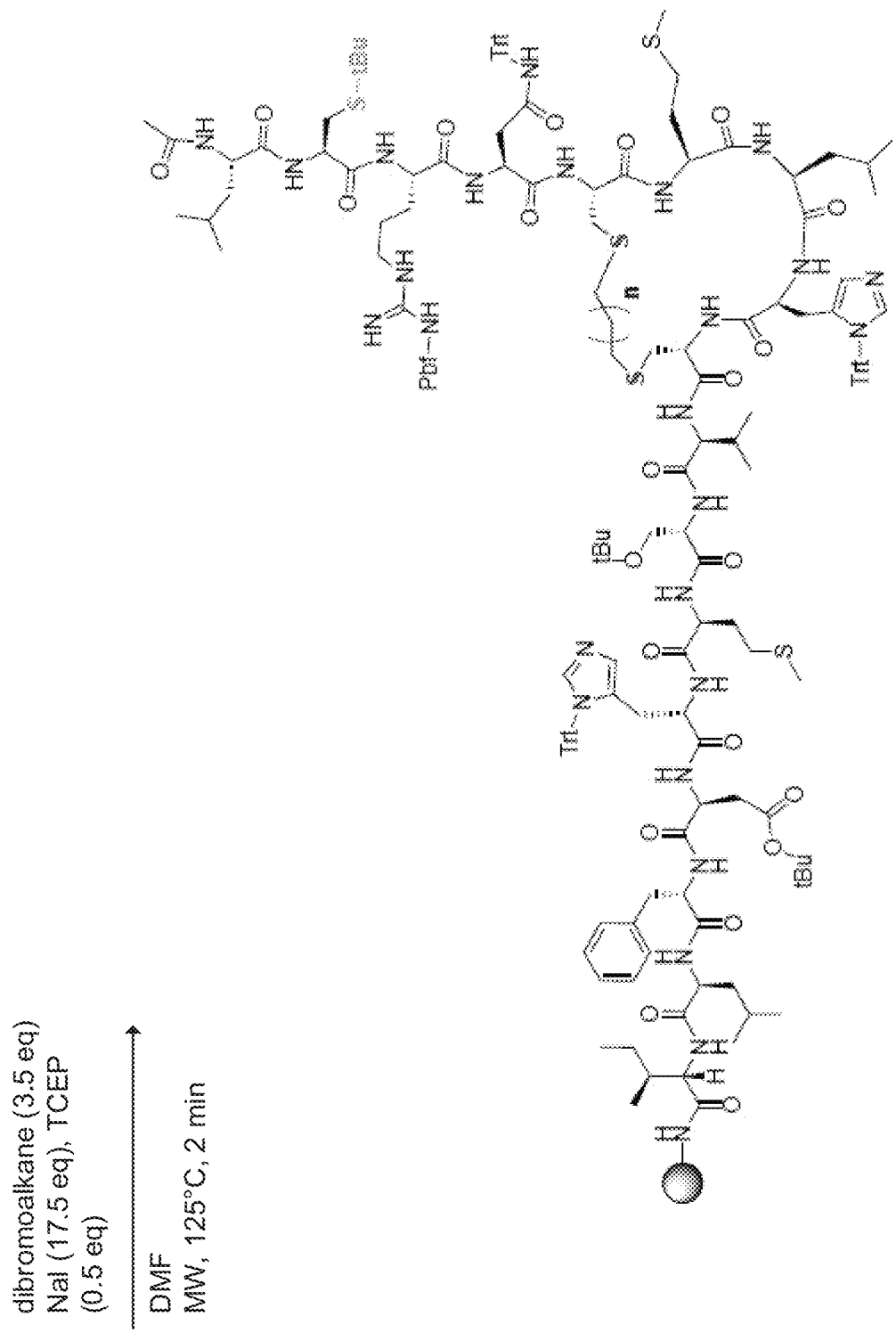
Figure 4H:
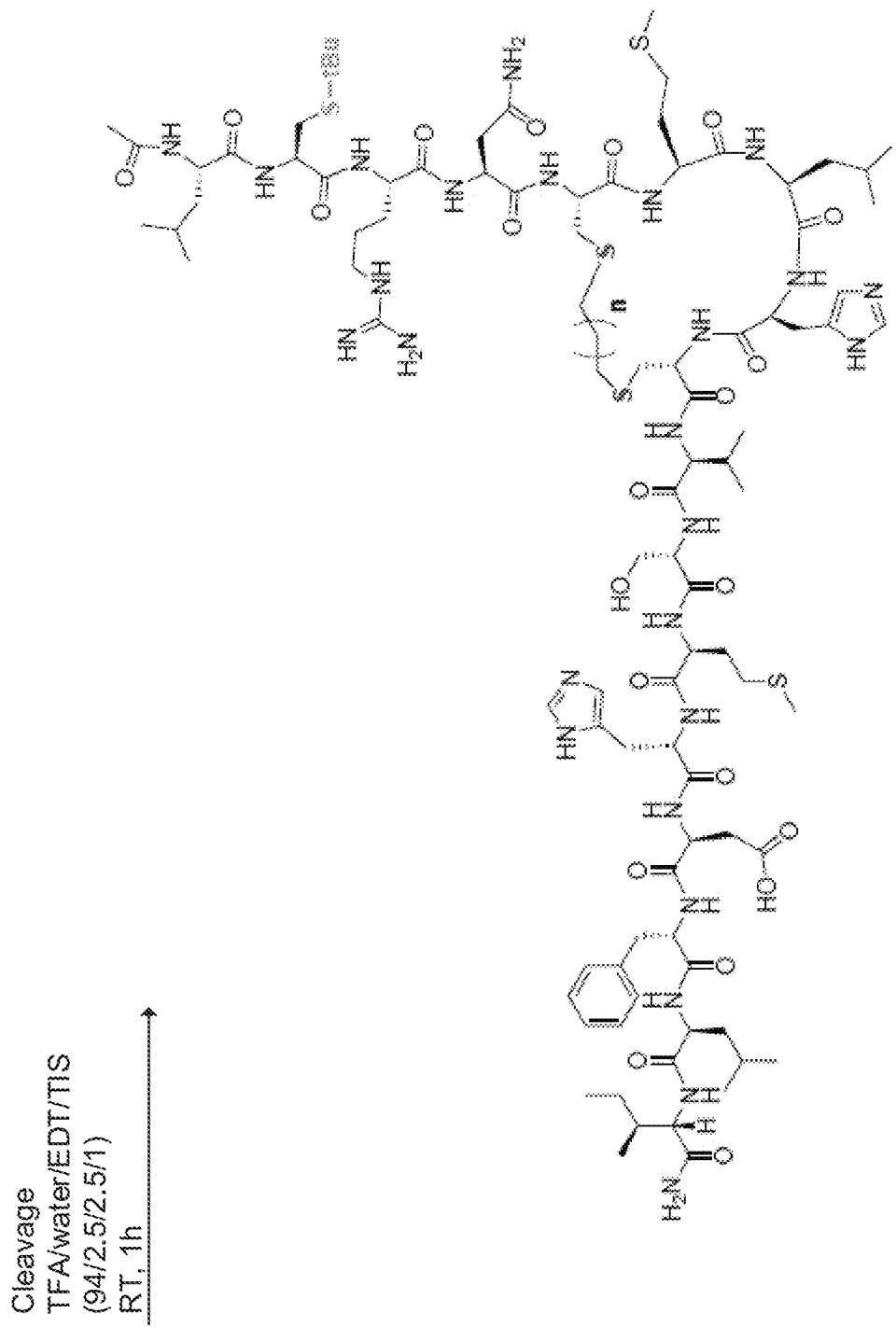
Figure 4I:
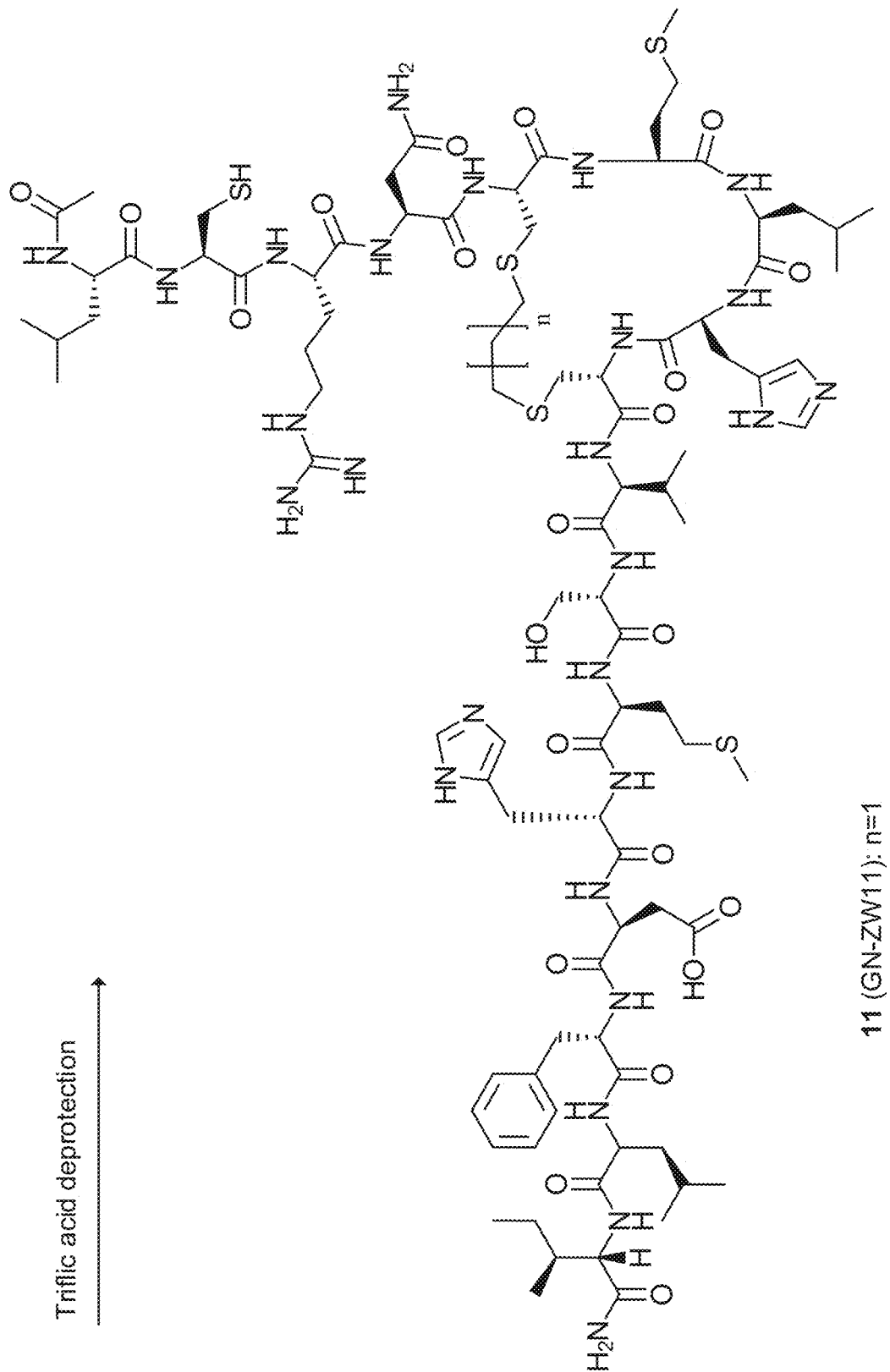

The impact of H3K27m3 inhibition on cell growth and proliferation of Caki-1 cells was investigated using healthy lung fibroblast cells IMR90 as a control. Cells were treated with compound 2 (GN-ZB2), GSK126 as a positive control, and an equimolar combination of both compounds for 72h. Proliferation assays indicated that both cyclopeptide 2 (GN-ZB2) and GSK126 are capable of significantly arresting cell 1 growth, with IC$_{50}$ values of 0.25±0.03 μM and 0.15±0.06 μM, respectively, as quantified by a colorimetric method (FIG. 3C). More notably, a combination of both compounds yielded an IC$_{50}$ value of 0.06±0.01 μM with a combination index of 0.61, indicative of a marked synergistic antiproliferative effect. Similar results were obtained in the correspondent viability assays. The compounds displayed no cytotoxicity below 15 μM in non-cancerous human fibroblast IMR90 cells (FIG. 3D).

In another embodiment, the compound has a structure given by KRV[CSEYC](CH$_2$)$_3$RLRQLKRFRRA (GN-ZB2a) given by SEQ ID NO: 34.

GN-ZW11

Using the published crystal structure of an active PRC2 ortholog from yeast, four macrocycles (compounds 8, 9, 11 (GN-ZW11) and 12) were strategically designed and synthesized according to FIG. 4A, FIG. 4B, FIG. 4C, FIG. 4D and FIG. 4E, FIG. 4F, FIG. 4G, FIG. 4H, FIG. 4I. The solvent-exposed residues were replaced by cysteines for the planned stapling reaction.

Figure 5B:
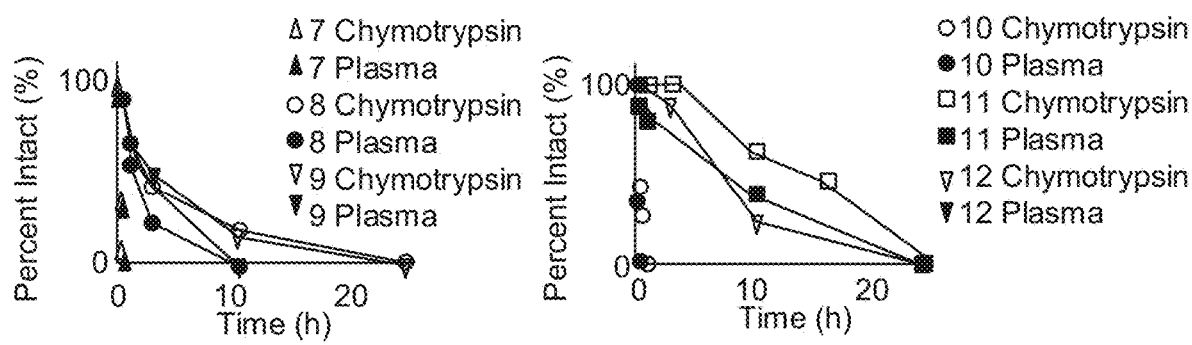
FIG. 5B both Chymotrypsin-based proteolytic degradation and the plasma assay show enhanced stability of i, i+4 bisthioether stapled peptides.
Figure 5C:
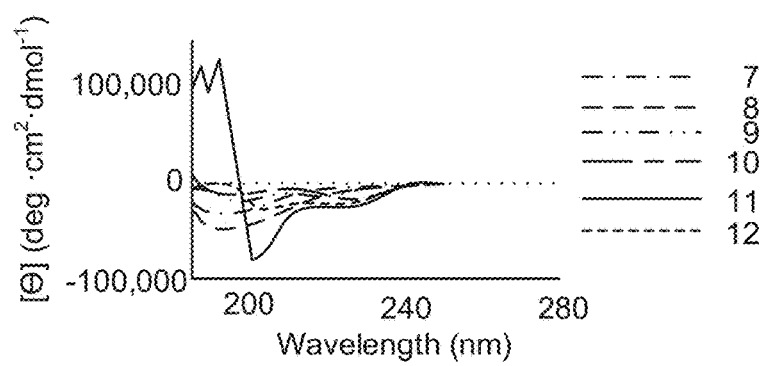
FIG. 5C is a CD spectra of stapled peptides and their linear counterparts measured in water at 20° C.

The proteolytic stability of these compounds was investigated by subjecting them to both a chymotrypsin and a plasma stability assay. For comparison, their linear counterparts were also studied. HPLC and LC/MS analysis showed in both assays marked protection of the i, i+4 cyclopeptides to proteolysis, in contrast to their respective linear analogues, which were fully degraded after a few minutes in both conditions (FIG. 5A and FIG. 5B). The impact of the staple on the secondary structure of the synthesized macrocycles was measured by circular dichroism (CD). This analysis indicated that stapling through a three-methylene hydrocarbon brace resulted in remarkable enhancement of the helical character for both series, more pronounced for compound 11 (GN-ZW11), which showed an overall helicity of 95% (FIG. 5A and FIG. 5C).

Figure 5D:
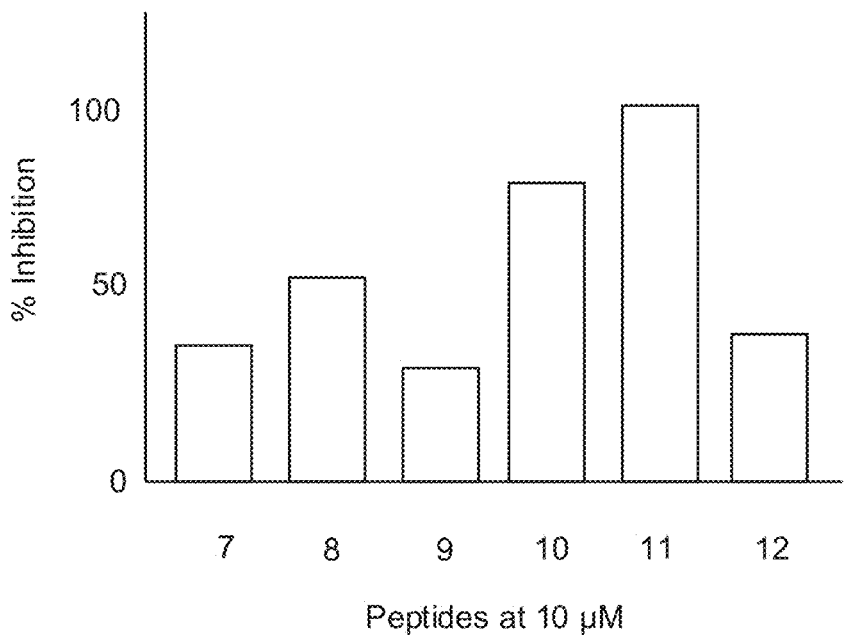
FIG. 5D shows inhibition of PRC2 catalytic function (H3K27Me3) as determined in an enzymatic assay using endogenous PRC2 extracted from a human clear cell renal carcinoma cell line (Caki-1), at peptide concentration of 10 µM.
Figure 5E:
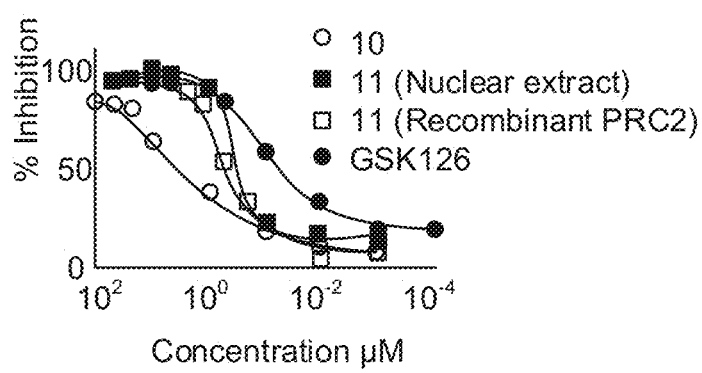
FIG. 5E is a plot of H3K27me3 inhibition obtained in an enzymatic assay using endogenous PRC2 extracted from Caki-1 cells and recombinant PRC2 complex (for compound 11)

To test if this induction of helical conformation correlated with biological activity, the cyclopeptide's ability to inhibit H3K27me3 in an enzymatic assay was investigated using as catalytic complex endogenous PRC2 extracted from a human clear cell renal carcinoma cell line (Caki-1). A well-characterized EZH2-SET domain inhibitor (GSK126) was used as a positive control for determining optimal assay conditions. A first screening at 10 μM peptide concentration showed that all compounds were capable of inhibiting H3K27me3. In line with the CD results, cyclopeptide 11 (GN-ZW11) resulted the more potent of both series (FIG. 5A and FIG. 5D). Further testing of this compound showed concentration dependent inhibition of PRC2 catalytic function with an IC50 value of 0.32±0.10 μM, resulting virtually as potent as GSK126 in the same assay conditions. The specificity of 11 (GN-ZW11) for targeting PRC2 complex assembly and function was then confirmed by performing the same enzymatic assay with pure recombinant PRC2 complex, which yielded almost the same result (FIG. 5E).

Figure 6A:
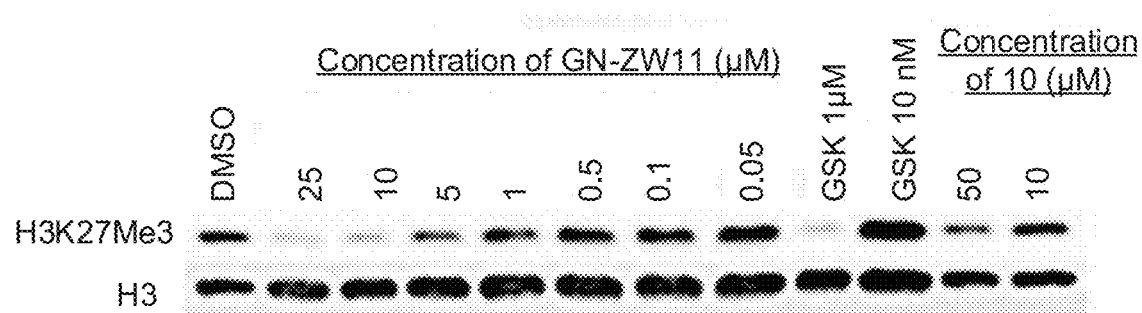
FIG. 6A is a Western blot analysis shows dose dependent response of H3K27me3 within metastatic Caki-1 cells, after treatment with stapled peptide 11 (GN-ZW11) once daily for 72h. Single concentration treatment with GSK126 (positive control) and linear wild type sequence 10 (negative control) are also shown.
Figure 6B:
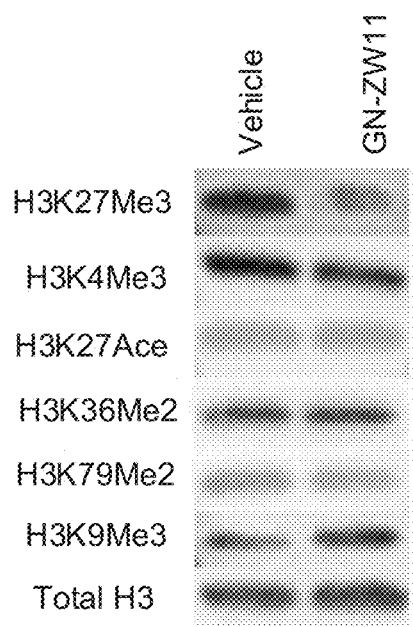
FIG. 6B shows selectivity of H3K27 trimethylation inhibition over a broad panel of histone post-translational modifications. Cells were treated with stapled peptide 11 (GN-ZW11, 5 µM) or vehicle, once daily for 72h.
Figure 7A:
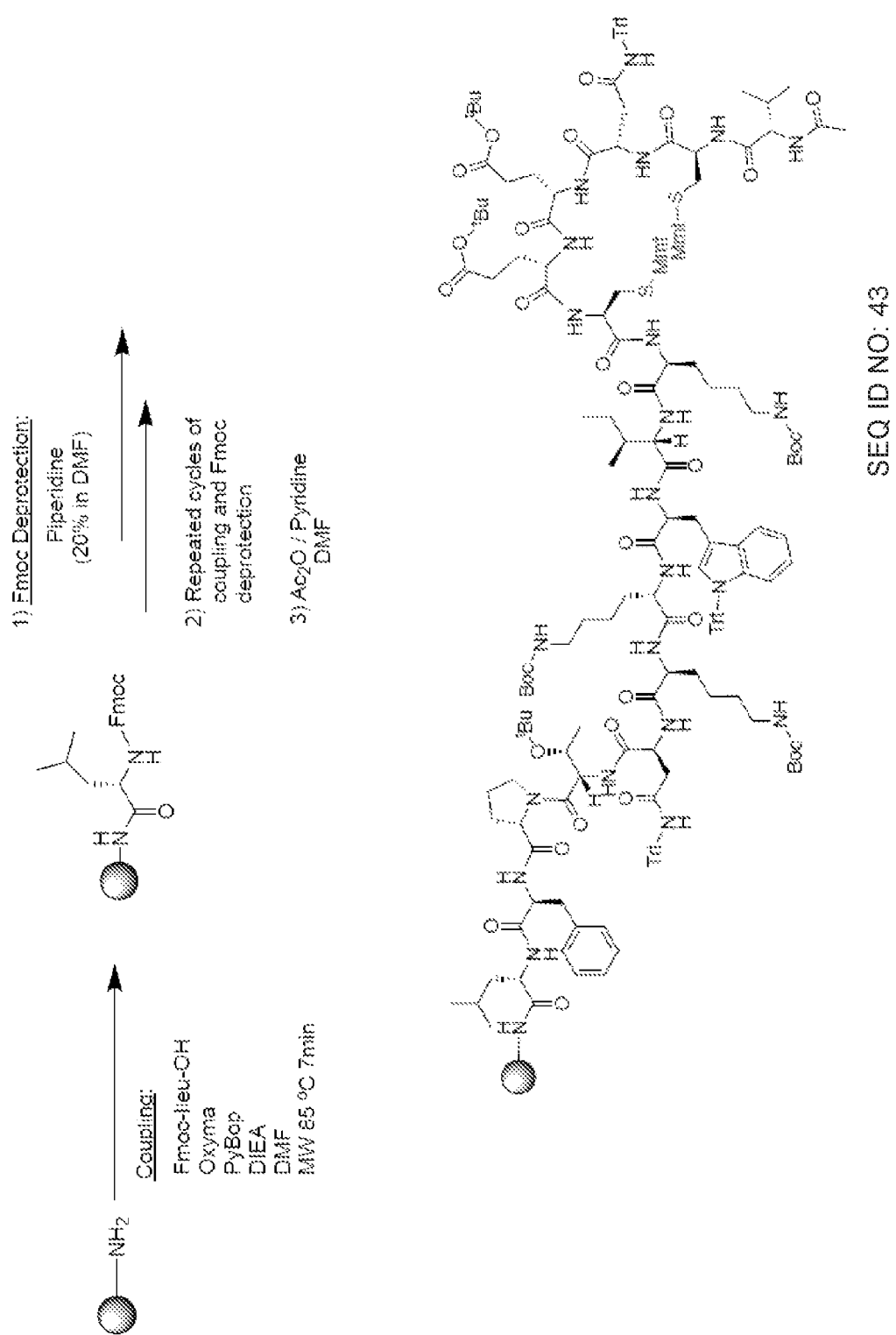
FIG. 7A, FIG. 7B, FIG. 7C and FIG. 7D depicts a synthetic scheme for the preparation of single turn stapled peptides (i, i+4) mimetics of the helix a1 of Nurf55, residues 20-35, targeting the SUZ12-NBE domain.
Figure 7B:
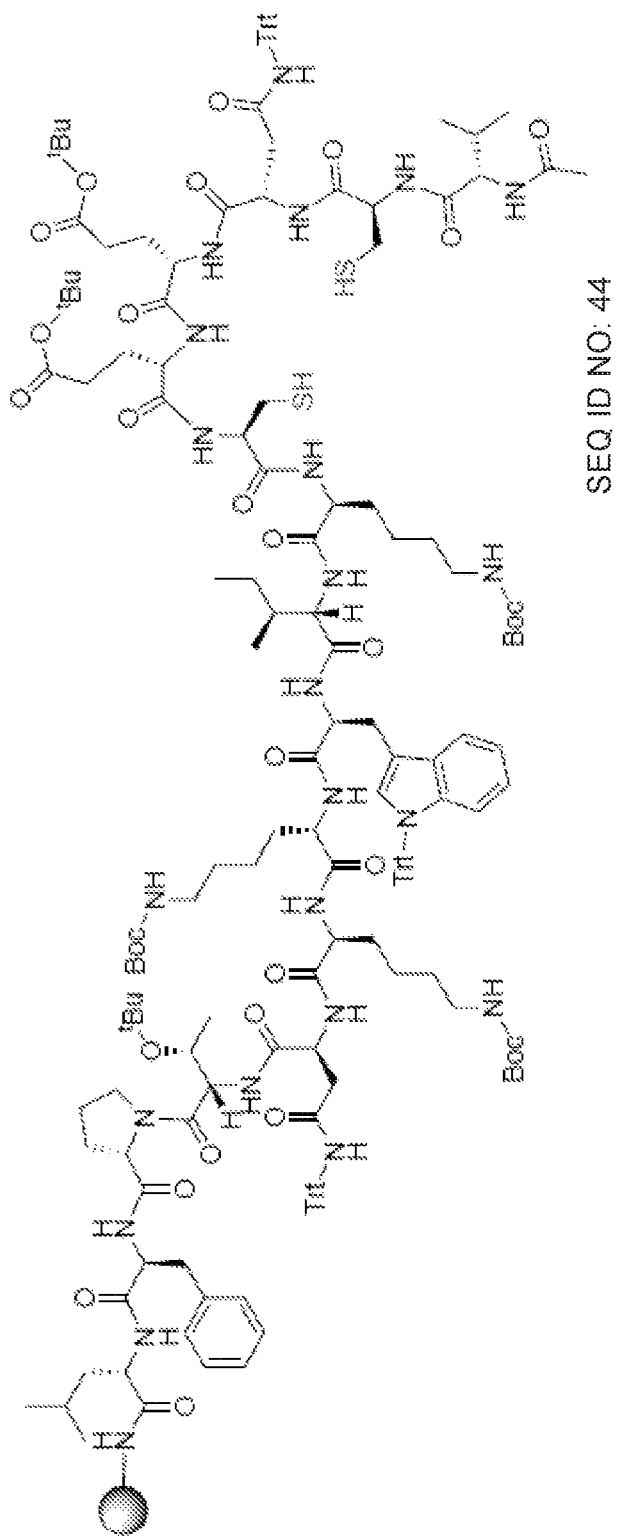
Figure 7C:
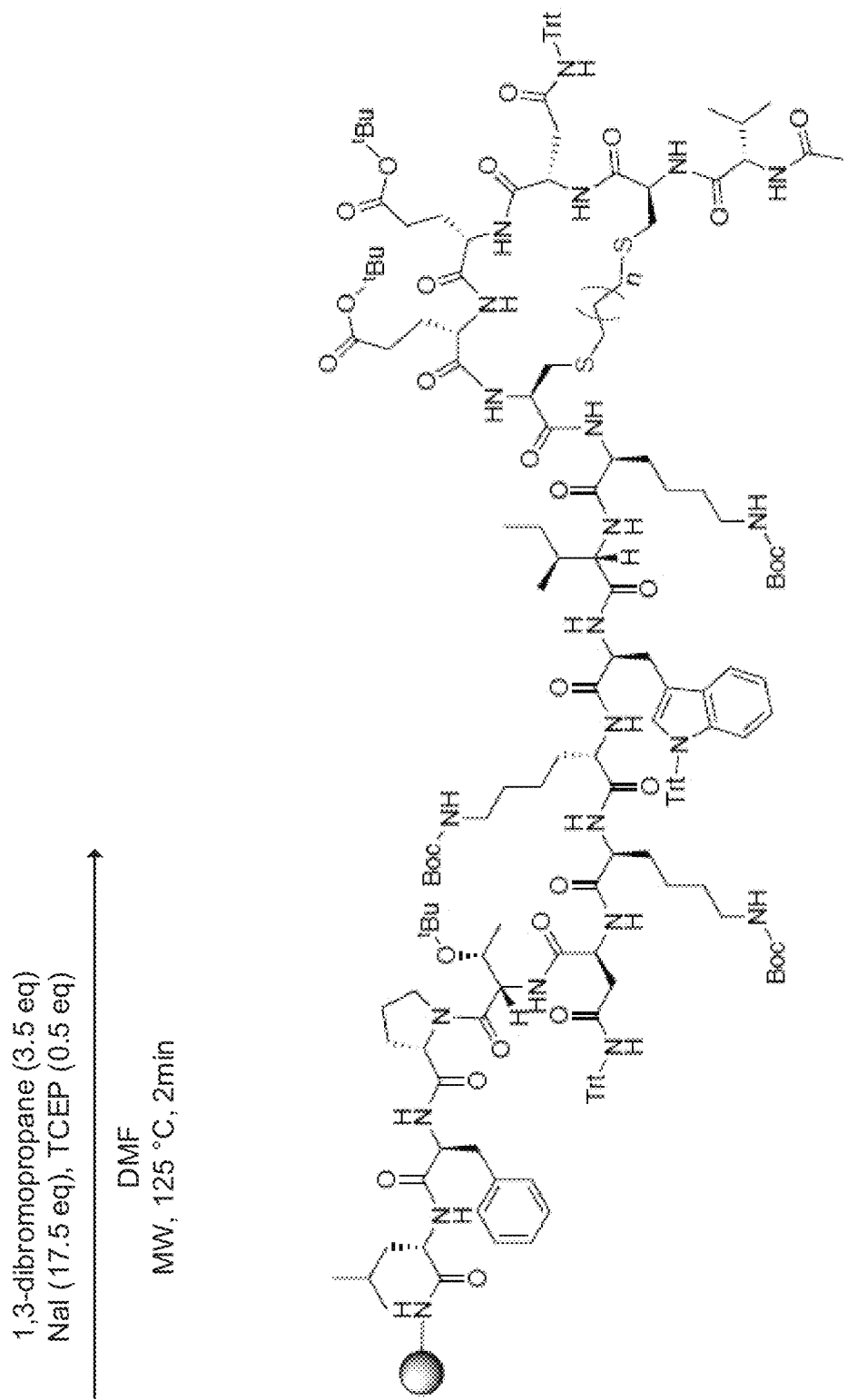
Figure 7D:
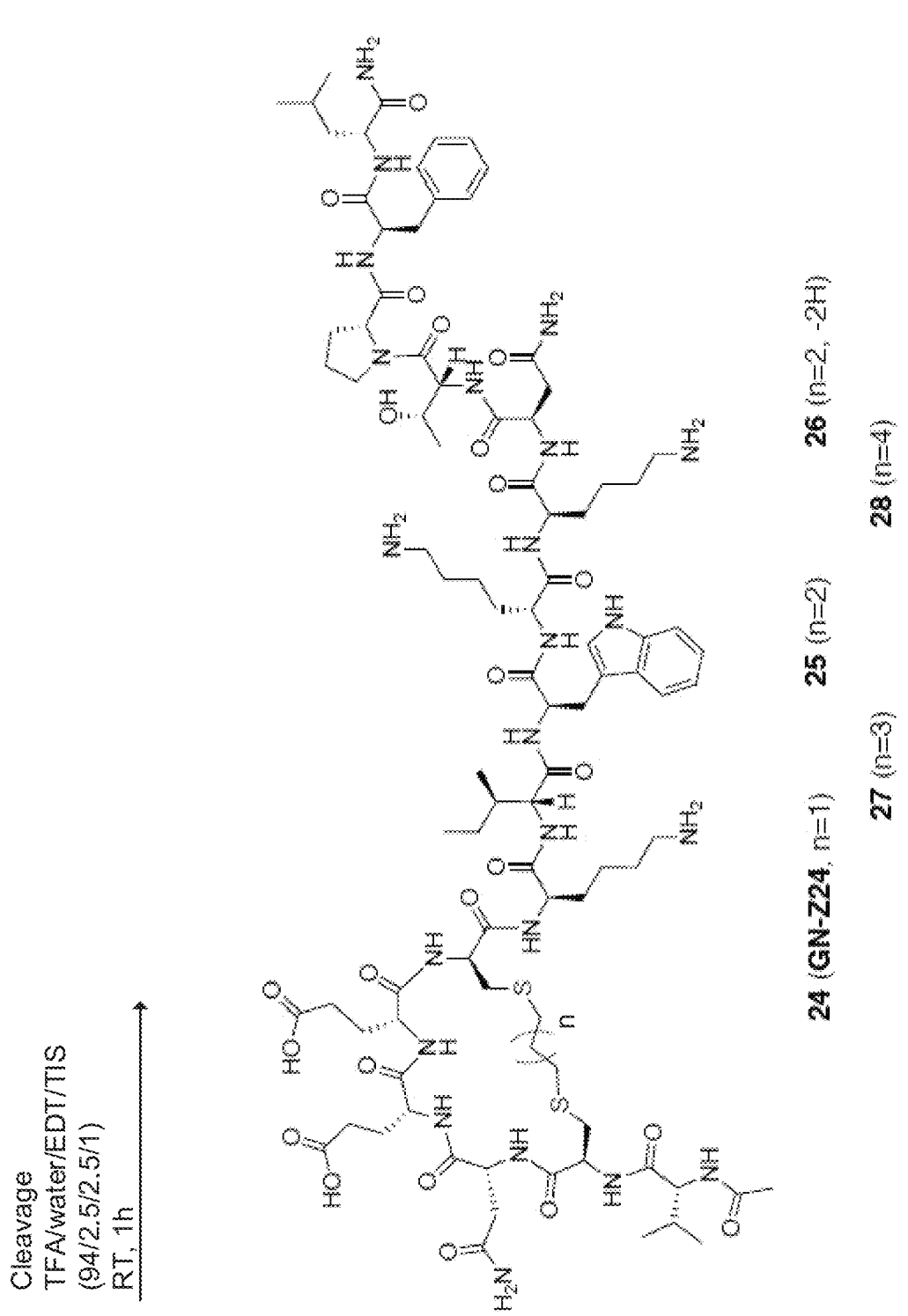

The cellular uptake of 11 (GN-ZW11) was explored by confocal microscopy, using an FITC-labeled derivative of it. Confocal imaging after incubation of caki-1 cells with fluorescently-tagged 11 (GN-ZW11) showed that it penetrates the cell membrane, and more importantly that it reaches the nuclei, where the targeted PRC2 complex is localized. Encouraged by these results, the ability of 11 (GN-ZW11) to target and functionally block PRC2-mediated H3K27me3 in Caki-1 cells was studied. Western blot analysis after cell treatment for 72h with varying concentrations of 11 (GN-ZW11) indicated a clear dose-response inhibition of H3K27me3 (FIG. 6A). Further quantitation of H3K27me3 by an absorbance-based colorimetric assay yielded an IC$_{50}$ of 1.04±1.34 μM, similar to that obtained in the enzymatic assay. To test the selectivity of the compound for PRC2 catalytic activity, its effect on different post-translational modifications was investigated. Cyclopeptide 11 (GN-ZW11) showed exceptional selectivity for H3K27Me3 inhibition. Thus, western blot analysis of histones isolated from cells treated with either high concentration of 11 (GN-ZW11, 5 µM) or vehicle control showed no effect on H3K4me3, H3K9me3, H3K36me2, H3K79me2 and H3K27Ac, whereas total inhibition of H3K27me3 was observed in the same experimental conditions (FIG. 6B). Altogether, this data confirmed that the stapled peptide is cell permeable and a potent selective inhibitor of the relevant physiological methylation of the PRC2 substrate.

GN-Z24

Twenty-one different macrocycles were designed to test four different families of stapled peptides crosslinked at four different positions in the native peptide sequence. A representative synthetic scheme, used for the preparation of peptides 23-28, it shown in FIG. 7A, FIG. 7B, FIG. 7C and FIG. 7D. All the designed peptides were synthesized on solid phase, via orthogonal Fmoc strategy. The all-hydrocarbon staples were installed chemoselectively on solid phase, by forming a bisthio-ether linkage, after selectively deprotecting the Mmt (4-methoxyltrityl) protecting groups from the corresponding cysteines residues. Following cyclization, the cyclopeptides were cleaved off the resin with a trifluoroacetic acid (TFA) cocktail (TFA/EDT/Water/TIS=94/2.5/2.5/1) and precipitated from diethyl ether. Finally, the resulting stapled peptides were purified by semipreparative HPLC. Characterization was performed by analytical HPLC and LC/MS.

Figure 8B:
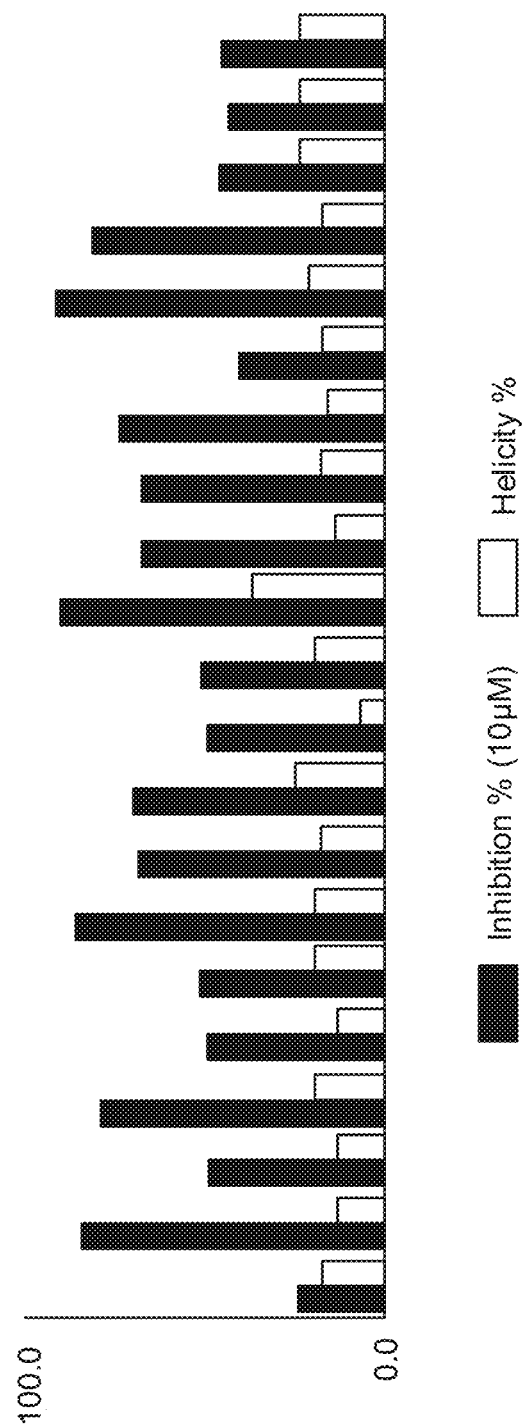
FIG. 8B shows helicities and percentages of H3K27me3 inhibition at 10 µM peptide concentrations, for all the synthesized stapled peptides and the linear analogue 13.
Figure 8C:
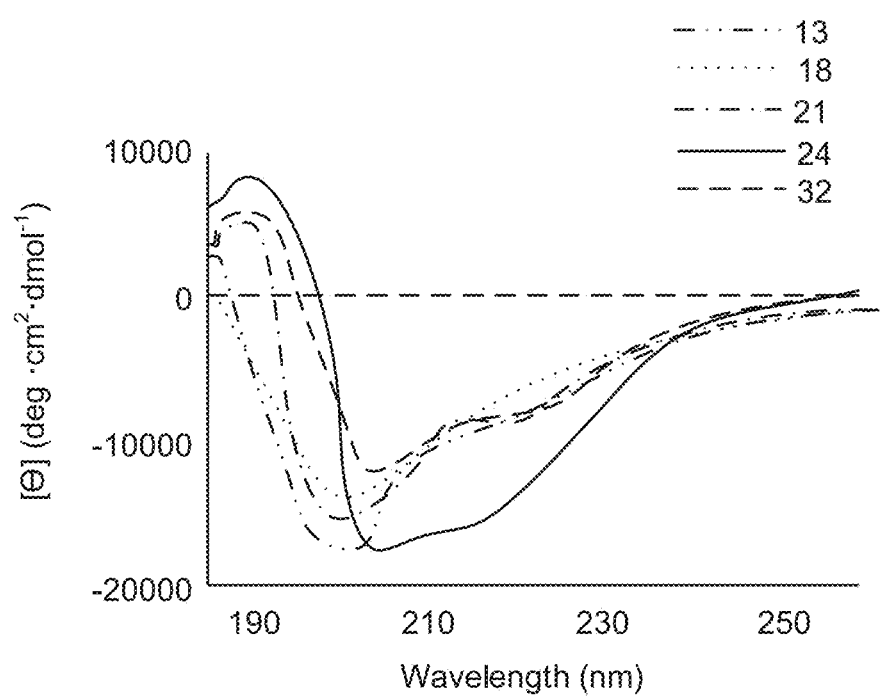
FIG. 8C shows CD spectra of each of the peptides that showed the higher helical character from each family, measured in water at 20° C.

The effect on the helicity of incorporating bis-thioether staples of different lengths and at different positions in the sequence of the resulting macrocycles were measured by circular dichroism (CD). As expected, both the position and the length of the linker resulted key factors on stabilizing the alpha-helical conformation of the peptide. Compound 24 (GN-Z24) showed the highest helical character of the whole series, with an improvement of 20% over that of the parent linear peptide 13 (FIG. 8A and FIG. 8B).

The effect on the helicity of incorporating bis-thioether staples at different positions in the sequence of the resulting macrocycles was explored by circular dichroism (CD). As expected, both the position and the length of the linker resulted key factors on stabilizing the alpha-helical conformation of the peptide. Compound 24 (GN-Z24) showed the highest helical character of the whole series, with an improvement 1 of 20% over that of the parent linear peptide 13 (FIG. 8A and FIG. 8B). To determine if such conformational effects would translate into a potent inhibition of PRC2 methyltransferase activity, all the synthesized macrocycles were subjected to an enzymatic assay specific for H3K27Me3, using as catalytic complex endogenous PRC2 extracted from a human clear cell renal carcinoma cell line (Caki-1). A well-characterized EZH2-SET domain inhibitor (GSK126) was used as a positive control for determining optimal assay conditions. An initial screening of all the compounds at a concentration of 10 µM showed a high correlation between helical character and inhibitory activity (FIG. 8B). Interestingly, the more potent compound in each of the four series was the cyclopeptide resulting from stapling through a three-methylene hydrocarbon linker.

Figure 9A:
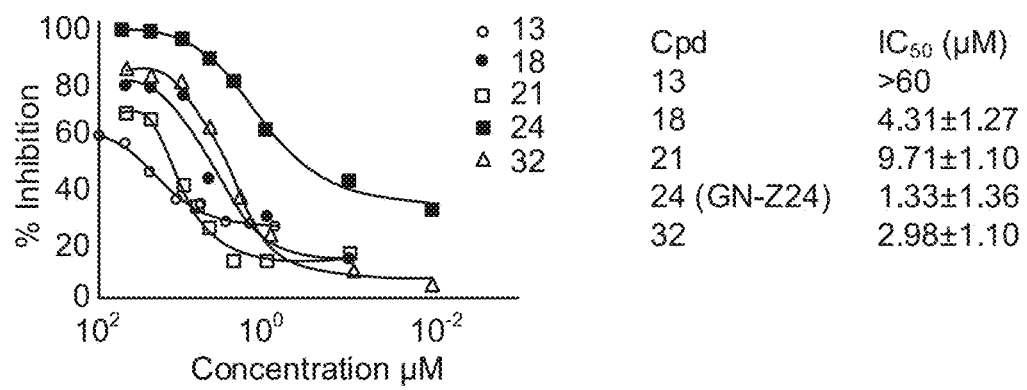
FIG. 9A depicts a graph of inhibition of PRC2 catalytic function (H3K27Me3) by the most potent stapled peptides of each series, as determined in an enzymatic assay using endogenous PRC2 extracted from a human clear cell renal carcinoma cell line (Caki-1)
Figure 9B:
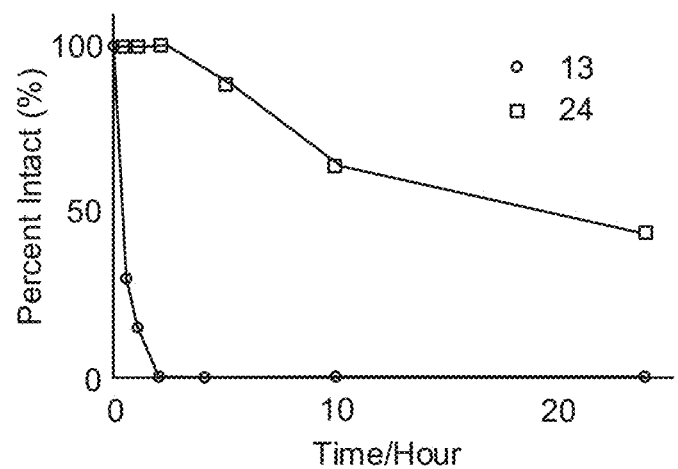
FIG. 9B shows a Chymotrypsin-based proteolytic degradation assay show enhanced stability of the i, i+4 bisthioether stapled peptide 24 (GN-Z24)

Further testing of these compounds under the same enzymatic assay confirmed that they were potent inhibitors of PRC2 catalytic activity with $IC_{50}$ values in the low micromolar range. In particular, cyclopeptide 24 (GN-Z24) showed the strongest inhibition with an $IC_{50}$ of 1.33±1.36 µM, markedly superior to that of its linear parent peptide 13 (FIG. 9A and FIG. 9B). Given such encouraging results, the feasibility of compound 24 (GN-Z24) to be used in functional assays was investigated by exploring both its proteolytic stability and its cell penetrating properties. Proteolytic stability was studied by subjecting peptide 24 (GN-Z24) to a chymotrypsin stability assay. For comparison, its linear counterpart 13 was studied in the same conditions. HPLC and LC/MS analysis showed marked protection of 24 (GN-Z24) to proteolysis ($t_{1/2}$=20.5 h), in contrast to its respective linear analogue, which was fully degraded in half an hour ($t_{1/2}$=0.5 h, FIG. 9B). Cellular uptake was studied by live confocal microscopy using a fluorescently labeled derivative of 24 (GN-Z24-FITC). Notably, confocal imaging after incubation of Caki-1 cells with FITC-tagged 24 (GN-Z24-FITC) showed its favorable cell penetrating properties, and more importantly that it localizes mainly in the nuclei, where the targeted PRC2 complex is located.

Figure 10A:
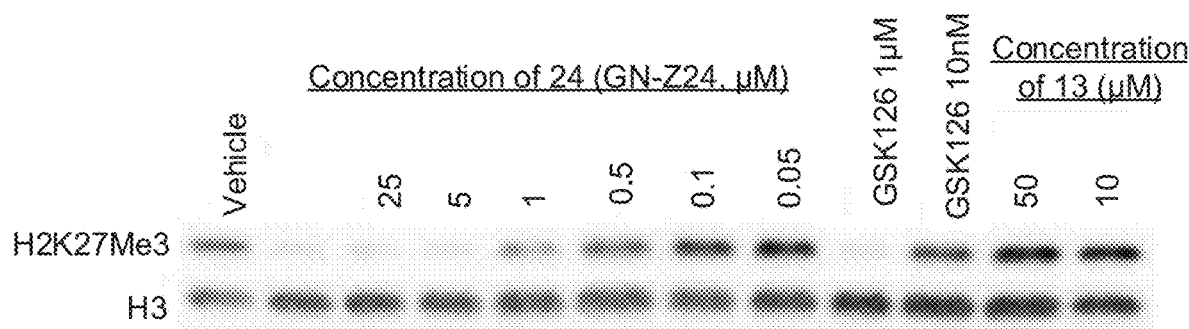
FIG. 10A is a Western blot analysis shows dose-dependent response of H3K27me3 within metastatic human clear cells renal carcinoma cells (Caki-1), after treatment with stapled peptide 24 (GN-Z24) once daily for 72h. Single concentration treatment with GSK126 (positive control) and linear wild type sequence 13 (negative control) in the same experimental conditions are also shown.
Figure 10B:
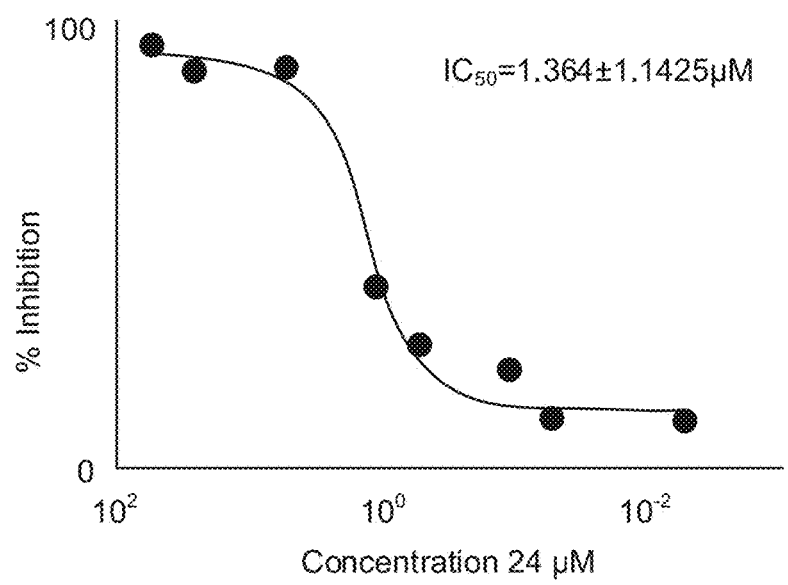
FIG. 10B shows quantitation of H3K27me3 using and absorbance-based colorimetric assay yielded an IC50 value of 1.36±1.14 µM. Protein loading was accurately corrected by measuring total H3 using an absorbance-based colorimetric assay.
Figure 10C:
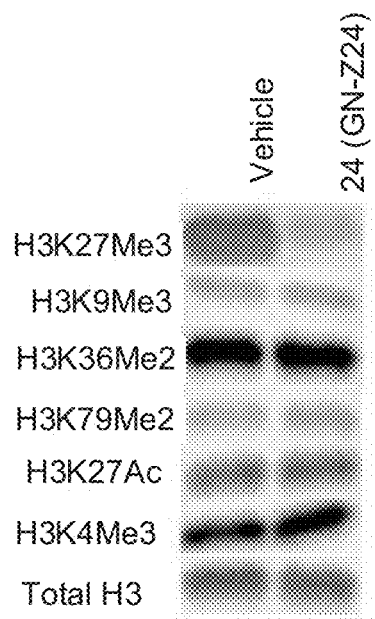
FIG. 10C demonstrates selectivity of H3K27 trimethylation inhibition over a broad panel of histone post translational modifications. Cells were treated with stapled peptide 24 (GN-Z24, 5 µM) or vehicle, once daily for 72h.
Figure 10D:
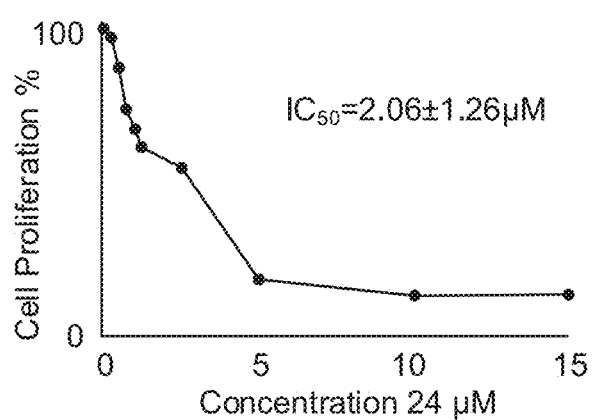
FIG. 10D shows the results of treatment of Caki-1 cells with cyclopeptide 24 (GN-Z24) significantly inhibits cell proliferation. Proliferation was measured after 72h of daily treatment with the correspondent compound. The data is presented as a mean of two independent experiments each with triplicate measurements.
Figure 11A:
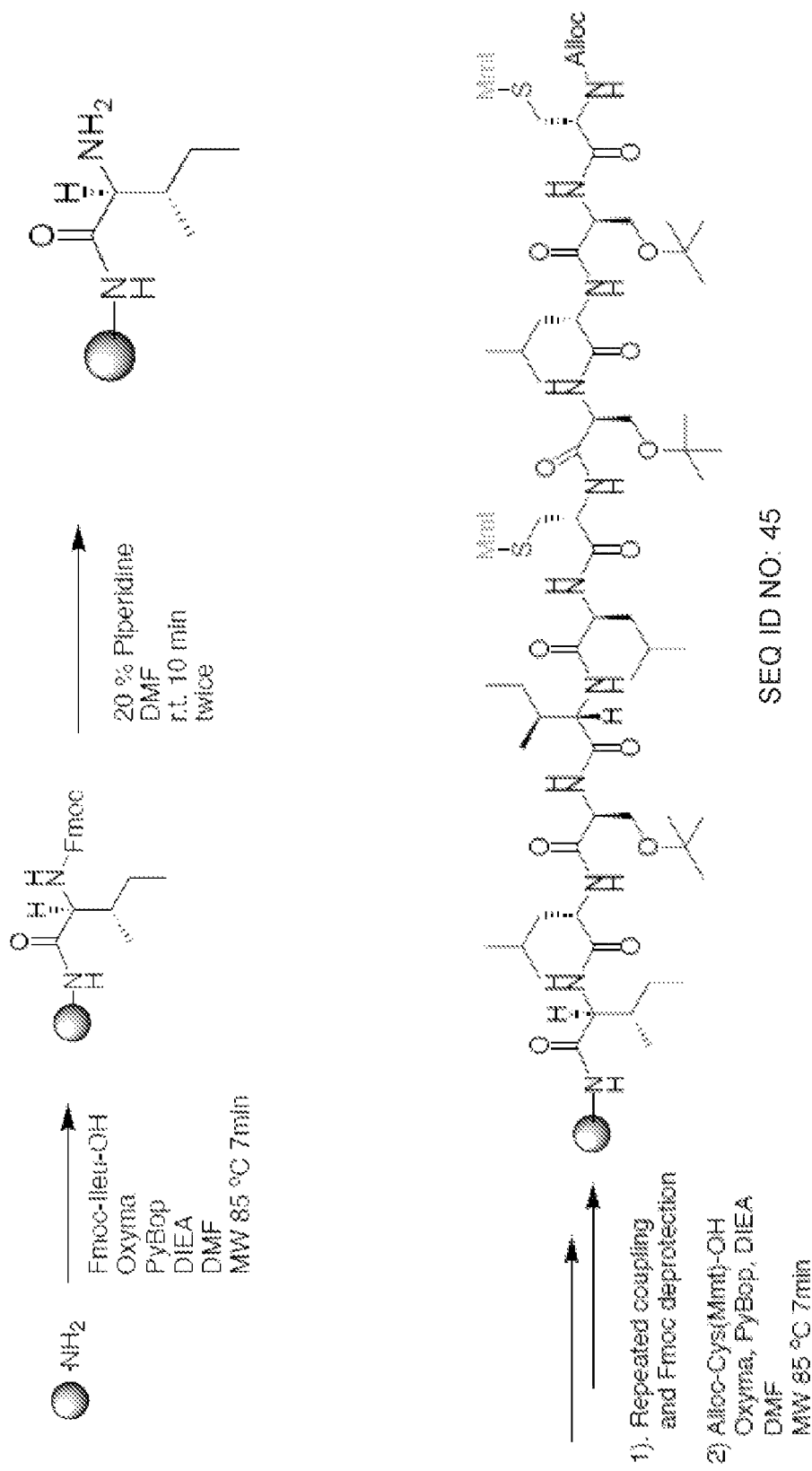
FIG. 11A, FIG. 11B, FIG. 11C, FIG. 11D and FIG. 11E is a synthetic scheme initially designed to study the stapling reaction on a 10mer linear peptide.
Figure 11B:
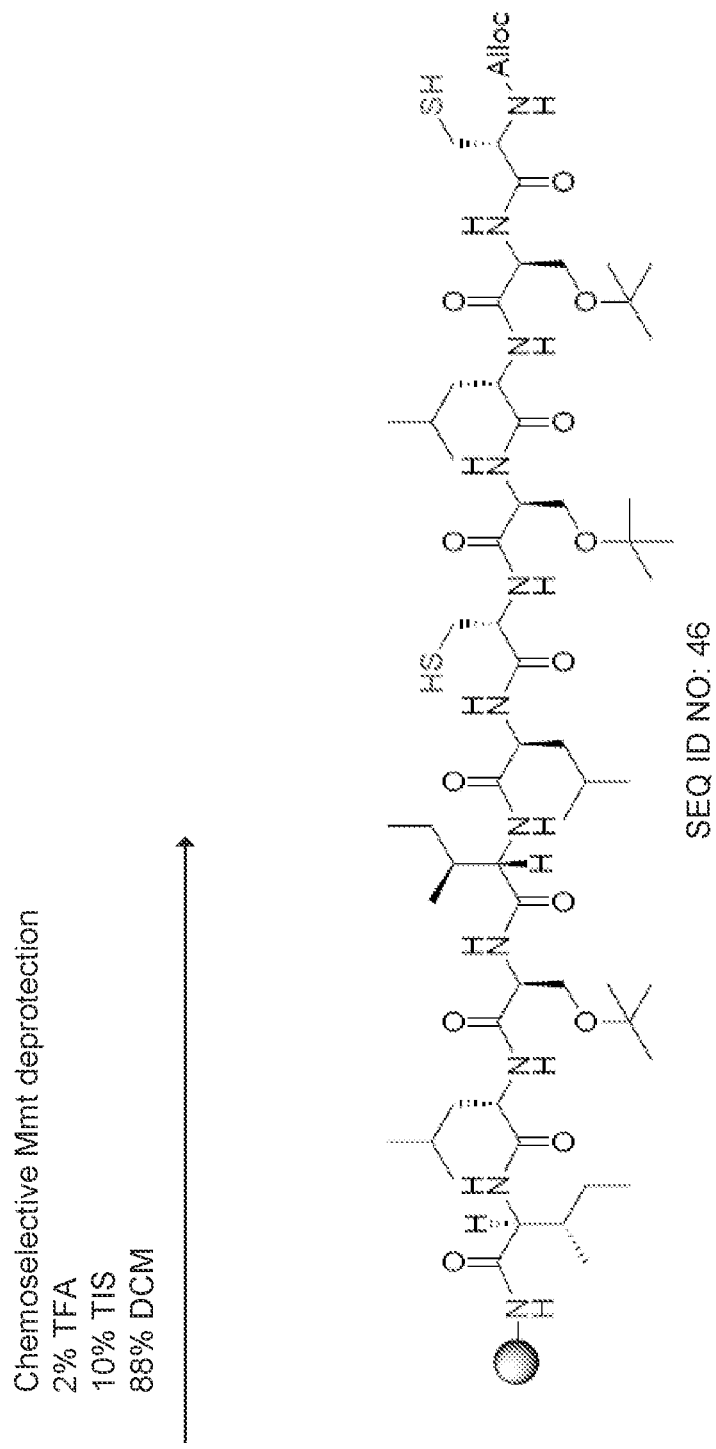
Figure 11C:
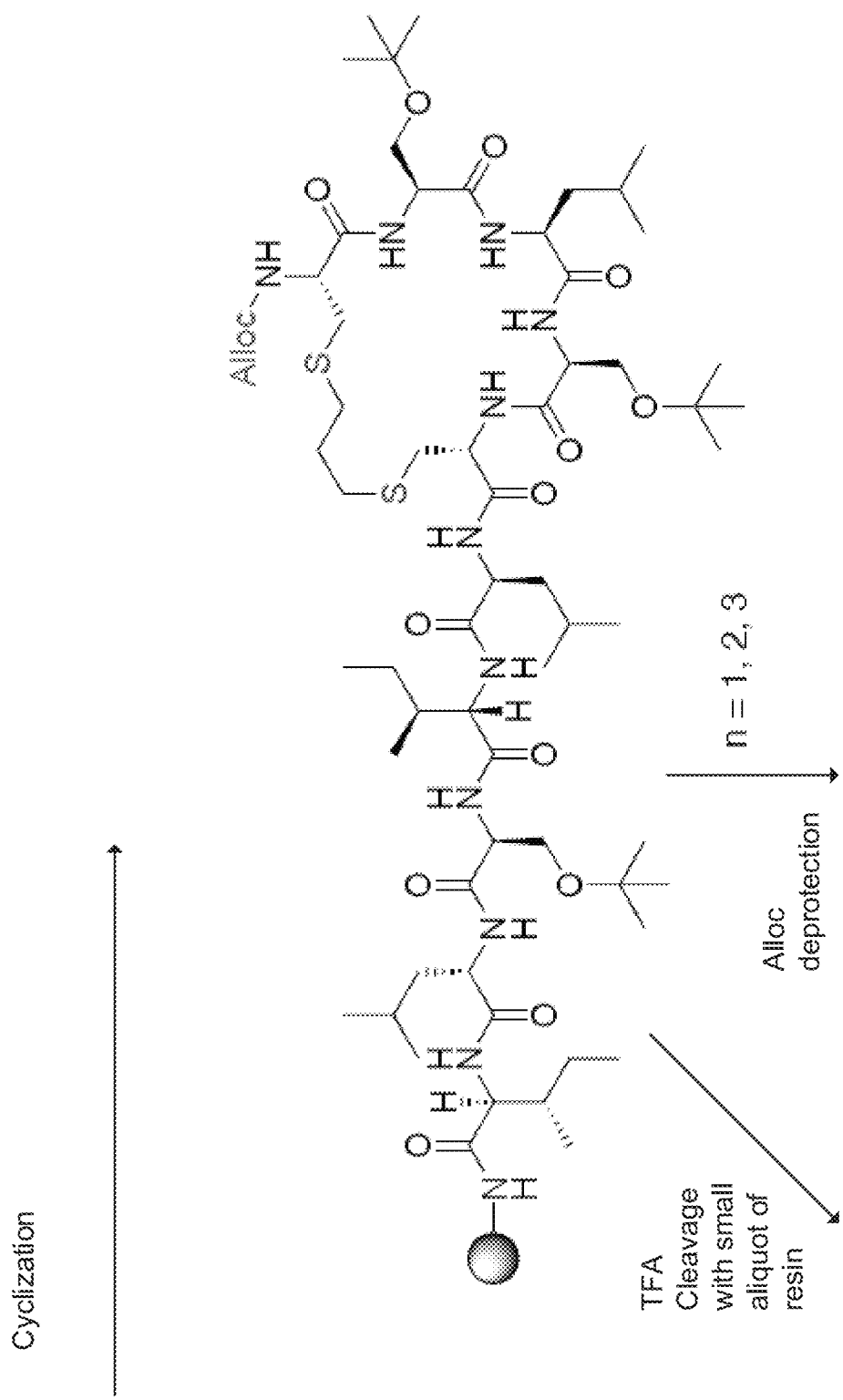
Figure 11D:
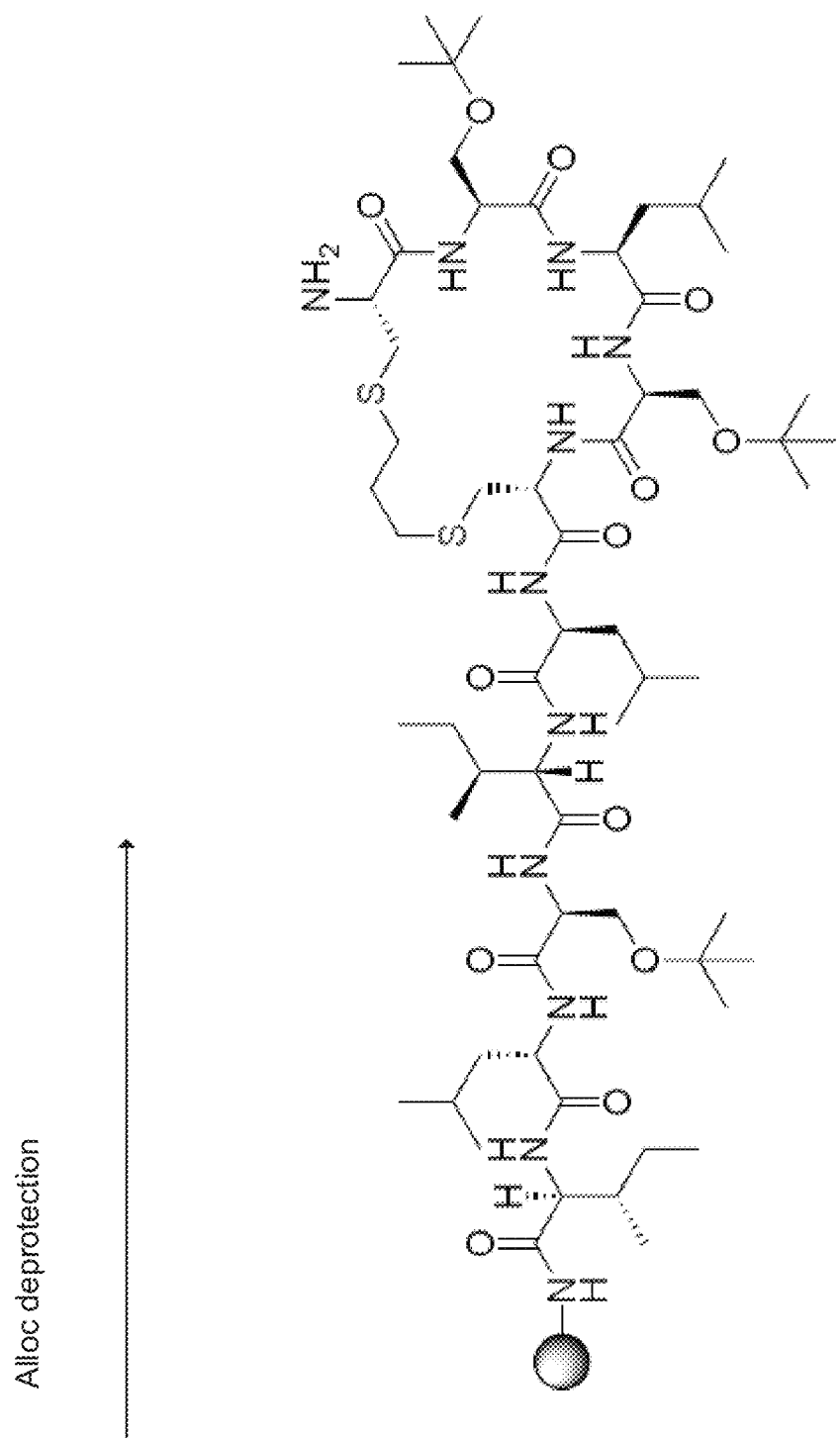
Figure 11E:
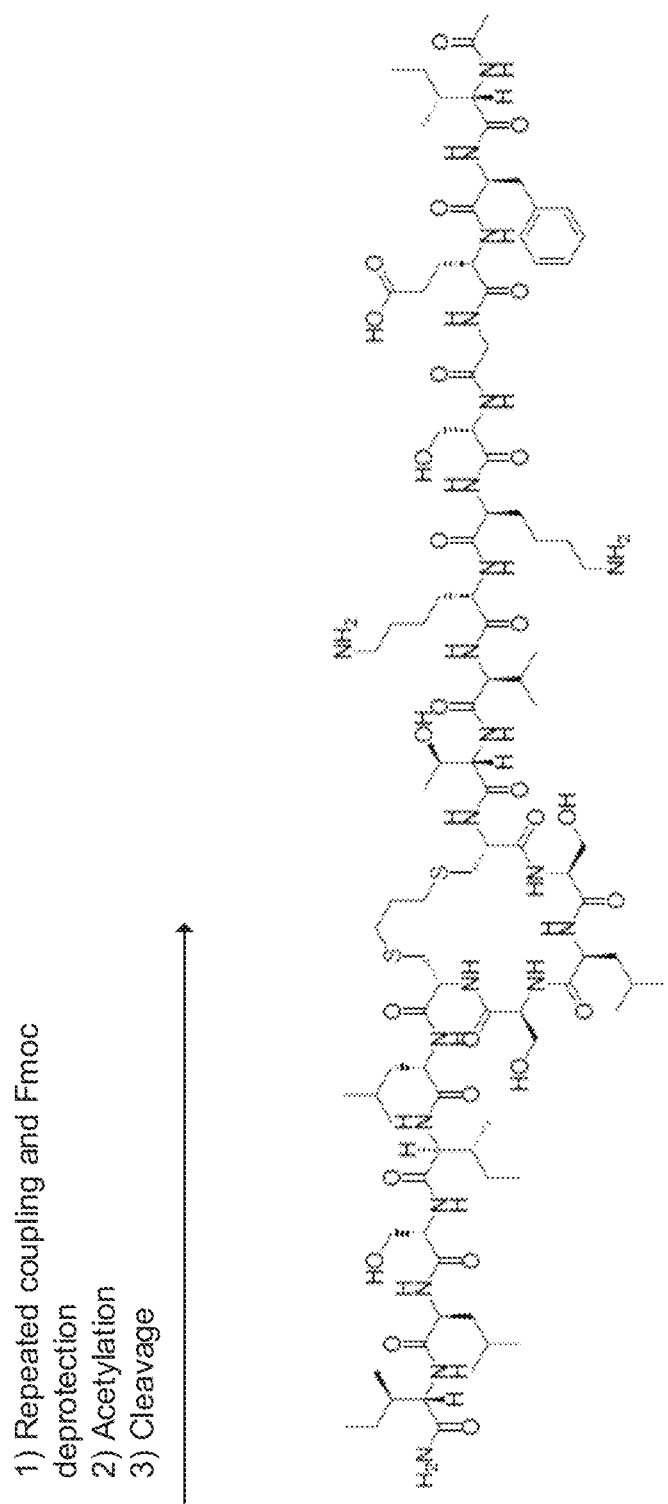
Figure 12A:
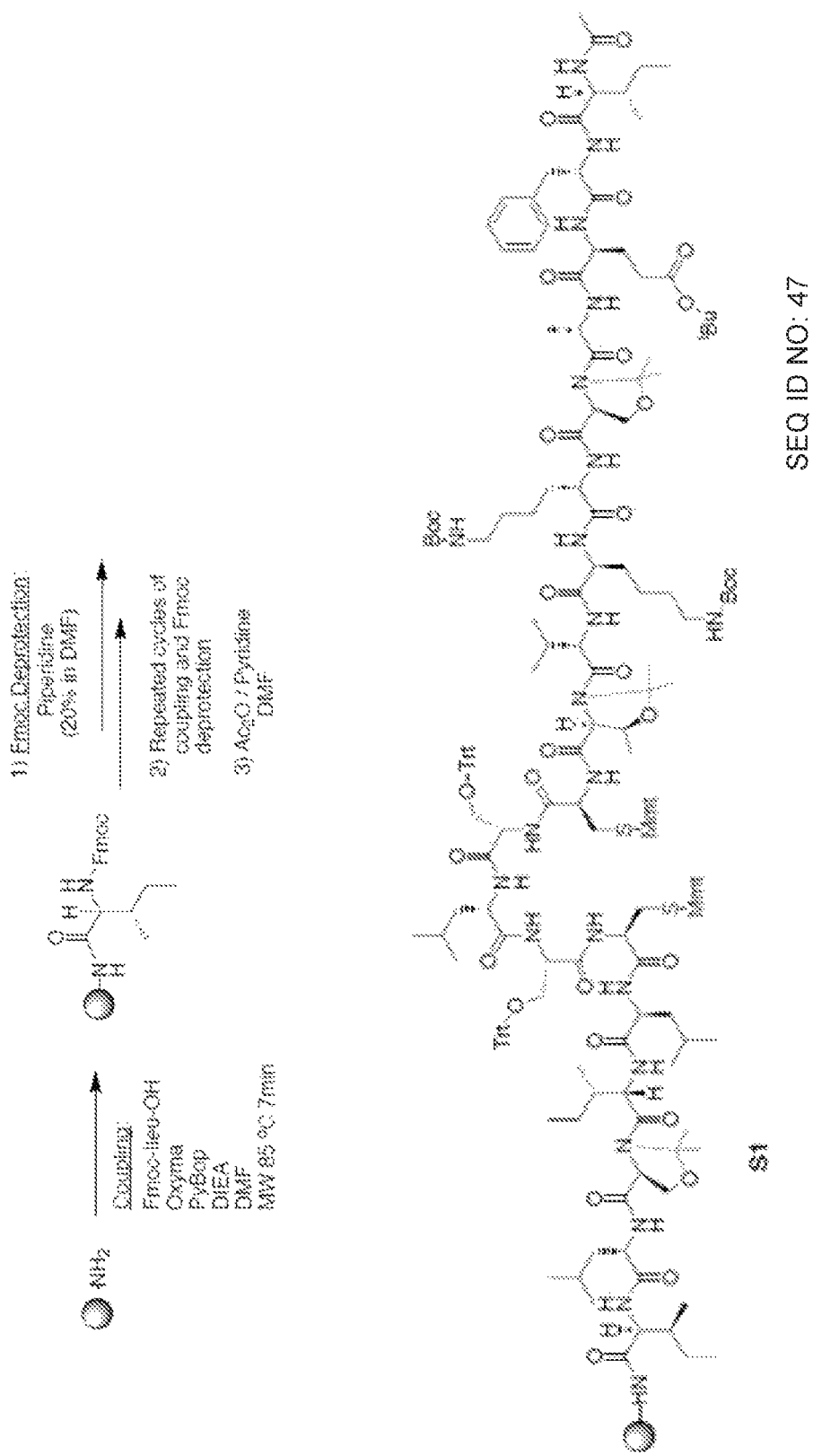
FIG. 12A, FIG. 12B, FIG. 12C and FIG. 12D is a synthetic scheme designed to study the stapling reaction on a 19mer linear peptide.
Figure 12B:
Figure 12B:
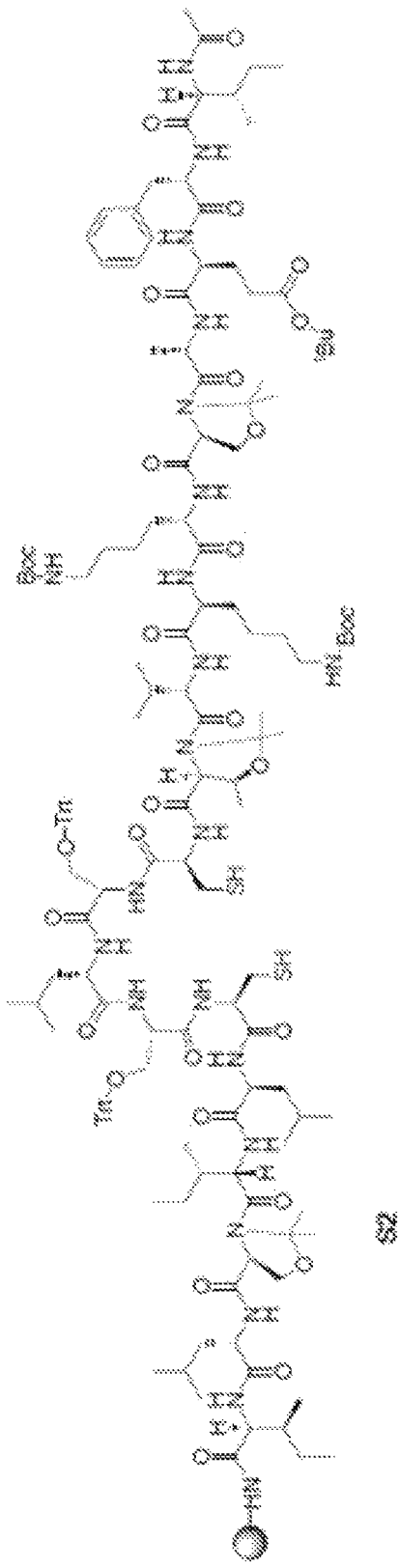
Figure 12C:
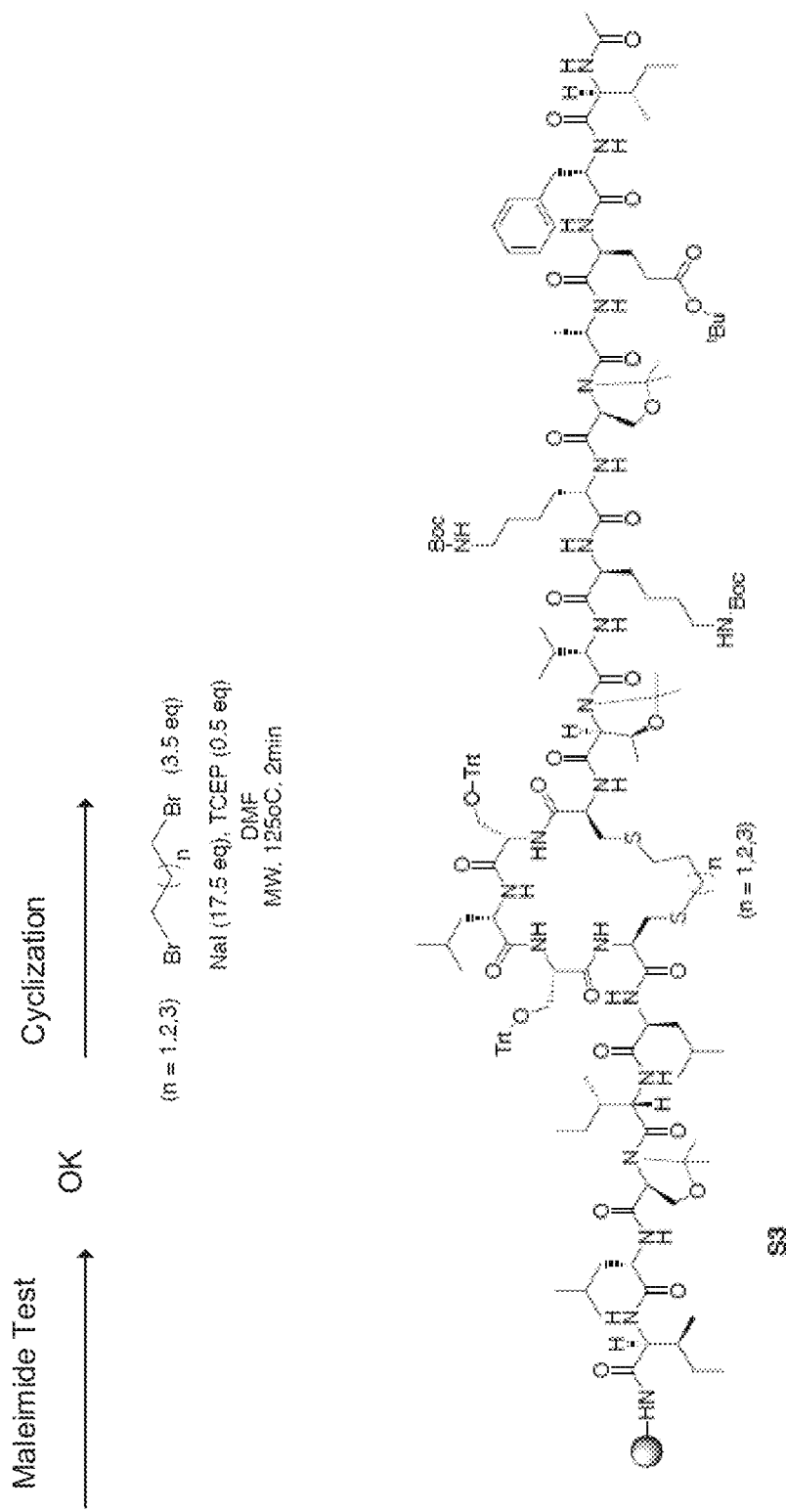
Figure 12D:
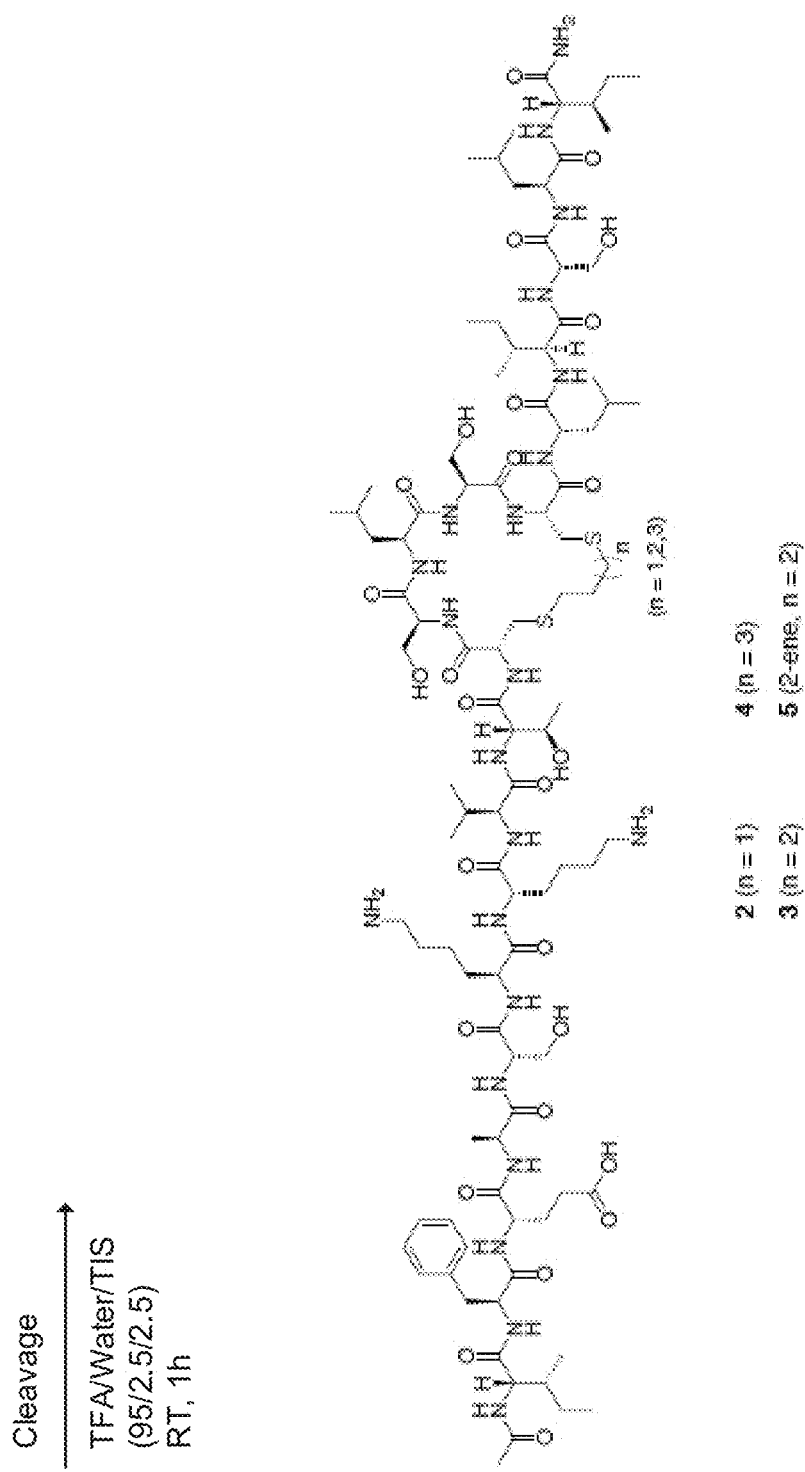
Figure 13A:
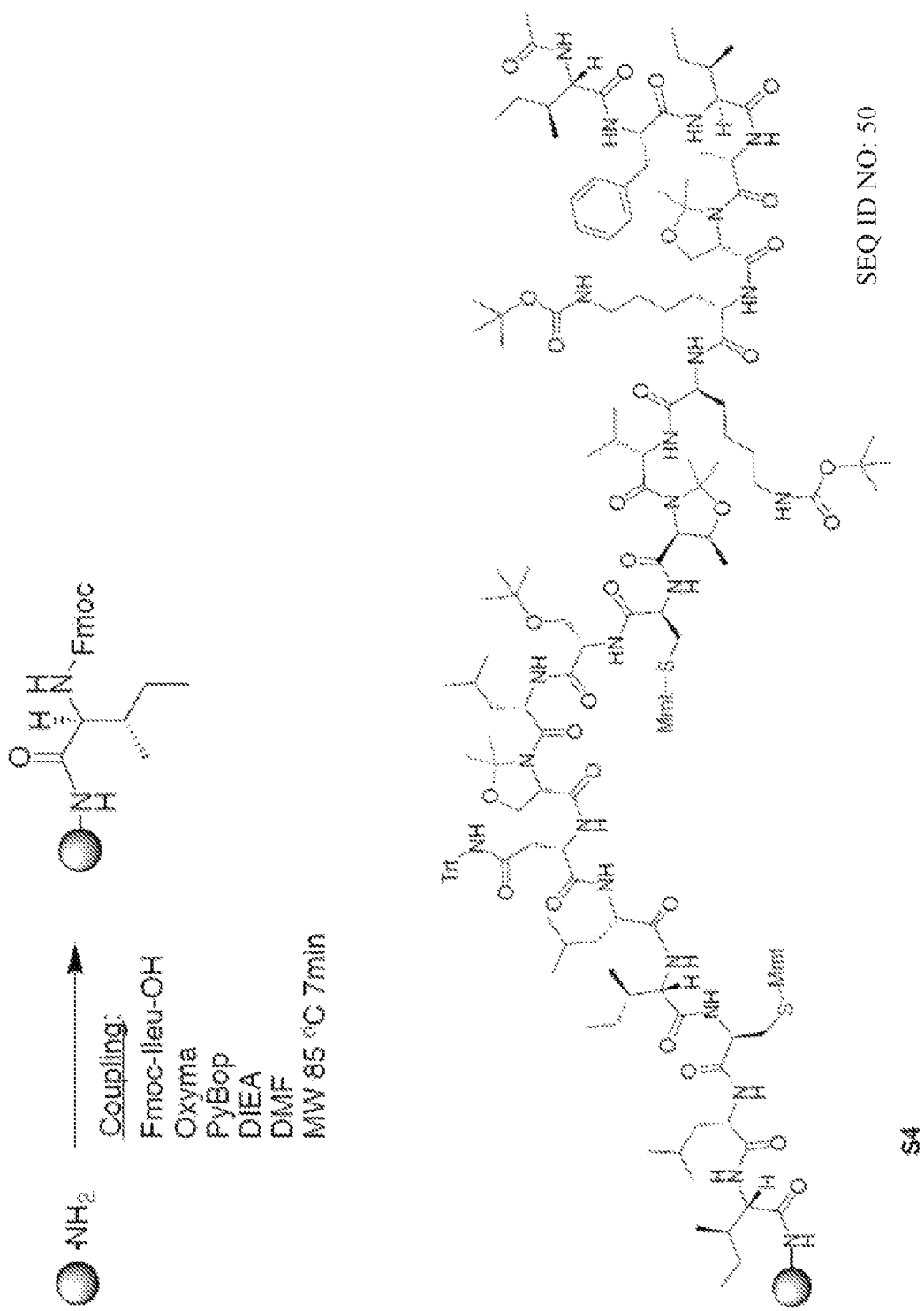
FIG. 13A, FIG. 13B, FIG. 13C and FIG. 13D depicts a synthetic scheme for the preparation of double turn stapled peptides (i, i+7) bearing linkers of different lengths. Pseudoproline dipeptides were used for the elongation of the precursor linear peptide.
Figure 13B:
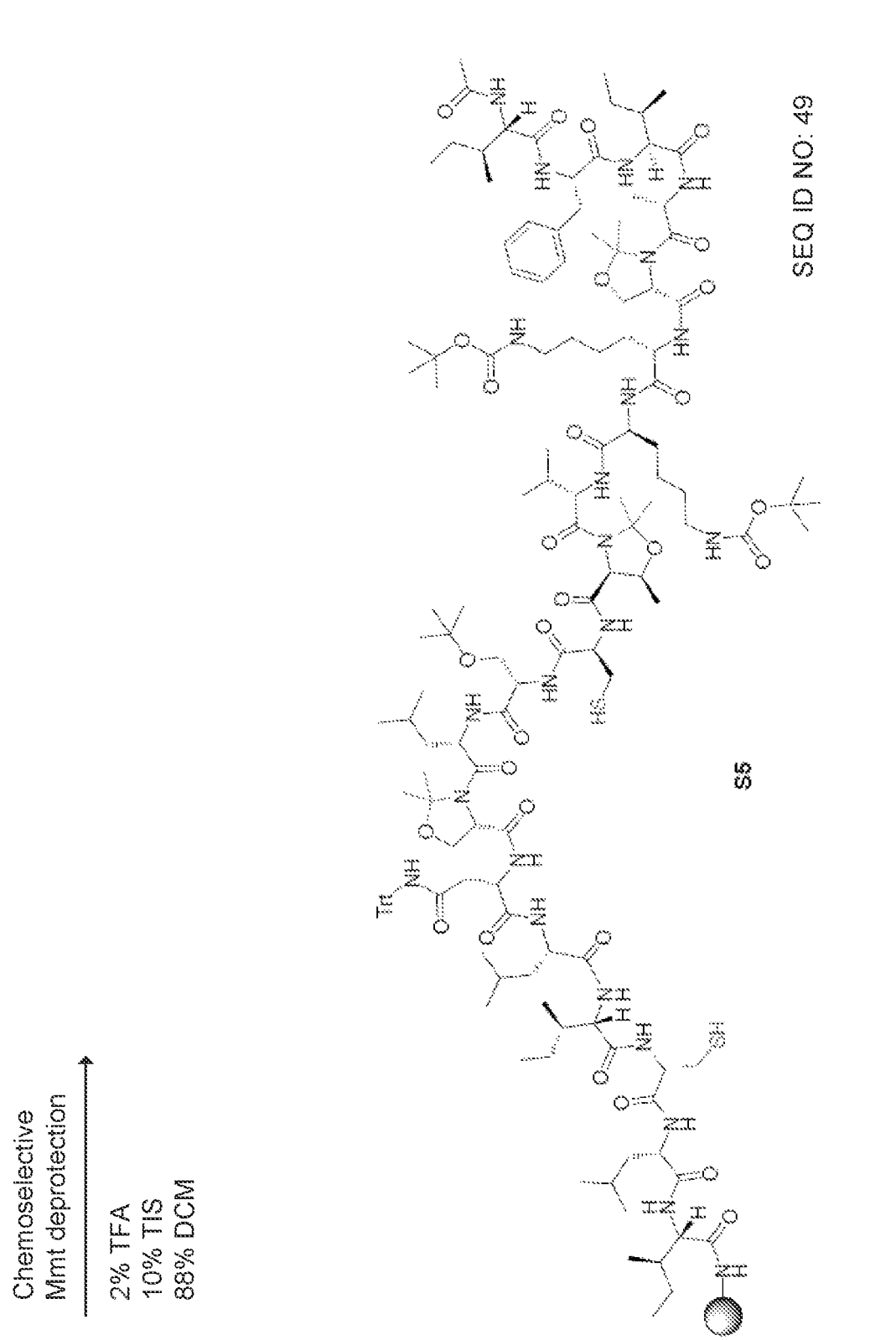
Figure 13C:
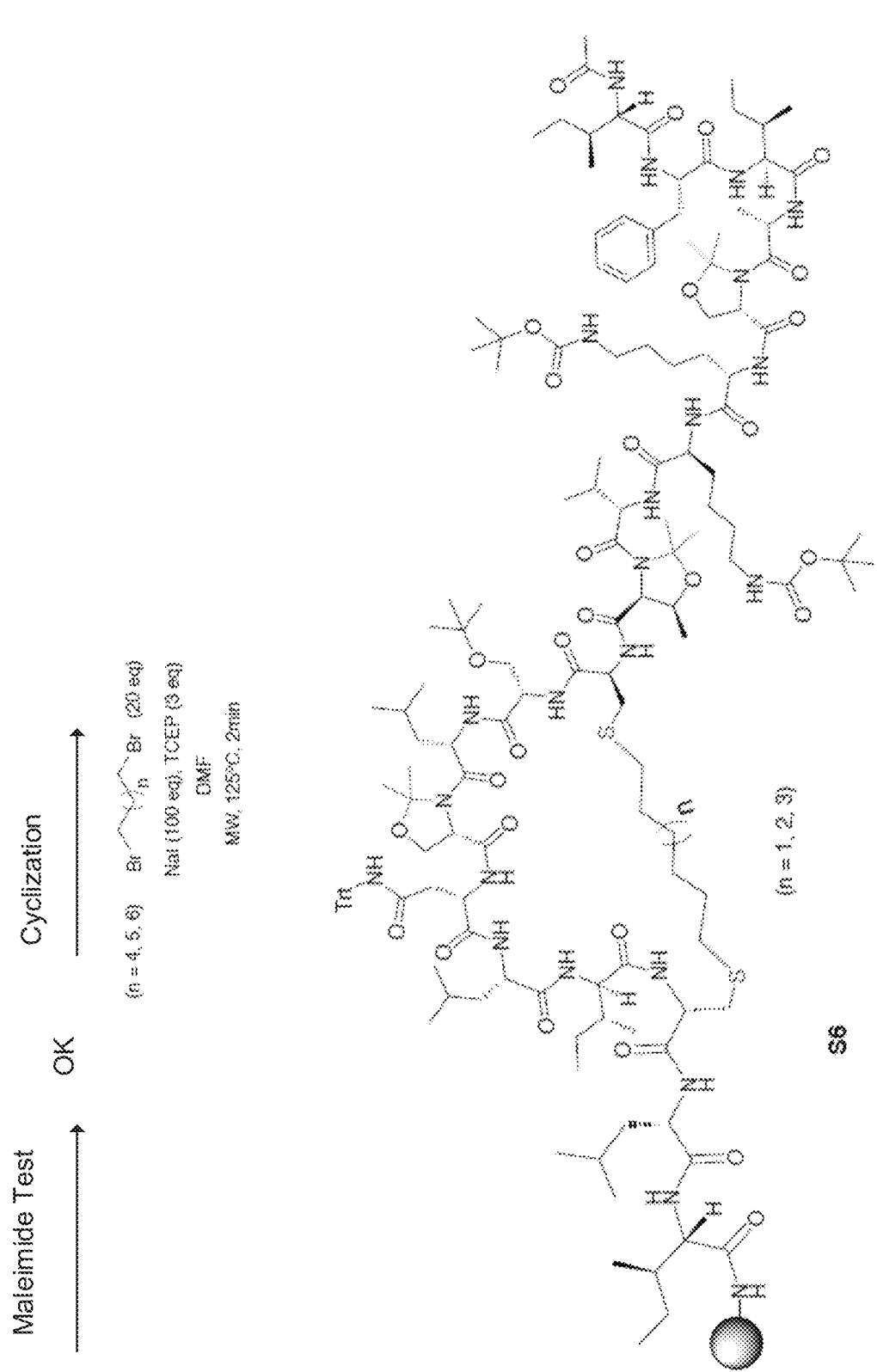
Figure 13D:
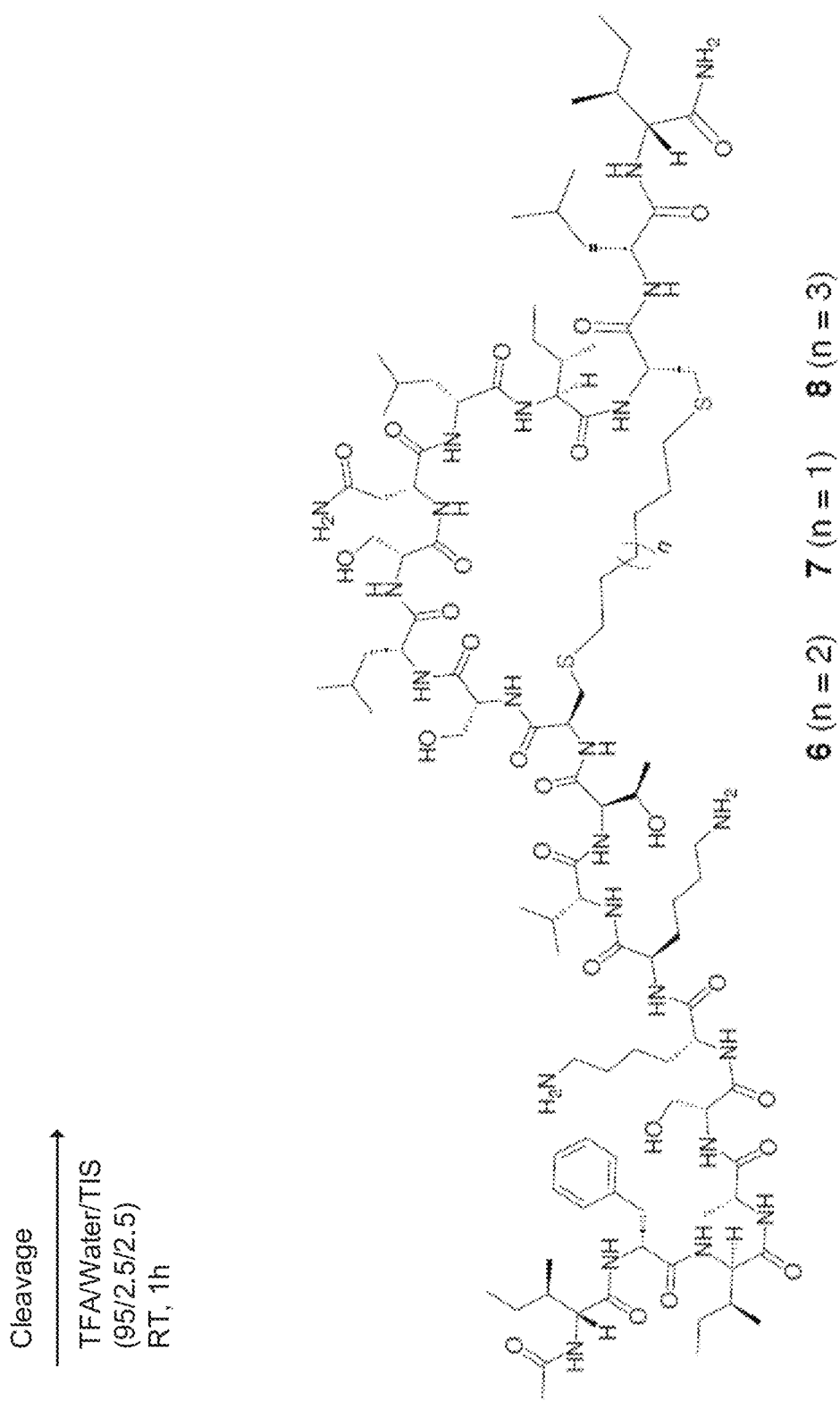
Figure 14A:
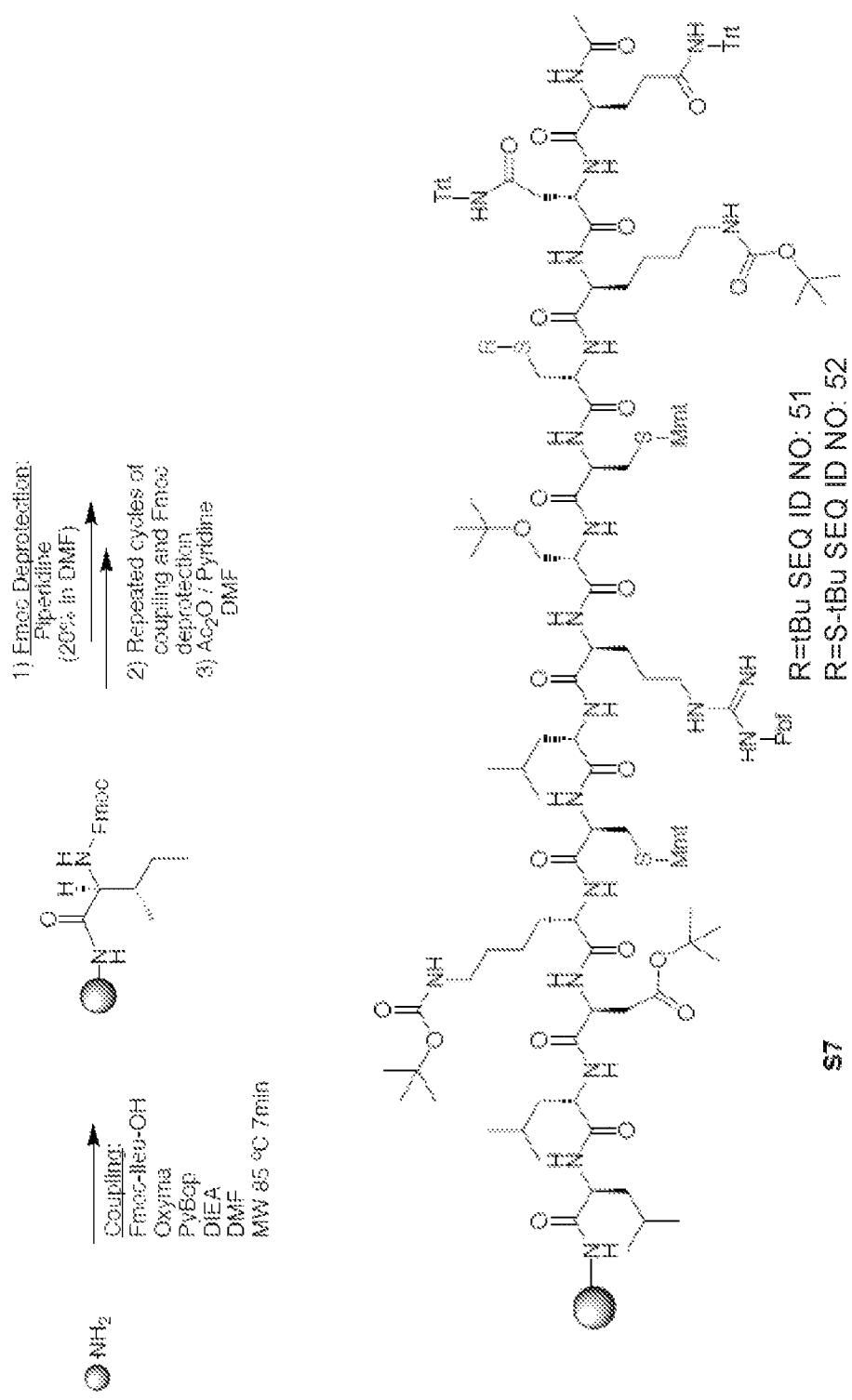
FIG. 14A, FIG. 14B, FIG. 14C and FIG. 14D depicts a synthetic scheme for the preparation of single-turn stapled peptides containing an additional cysteine residue in the sequence (i, i+4, +Cys)
Figure 14B:
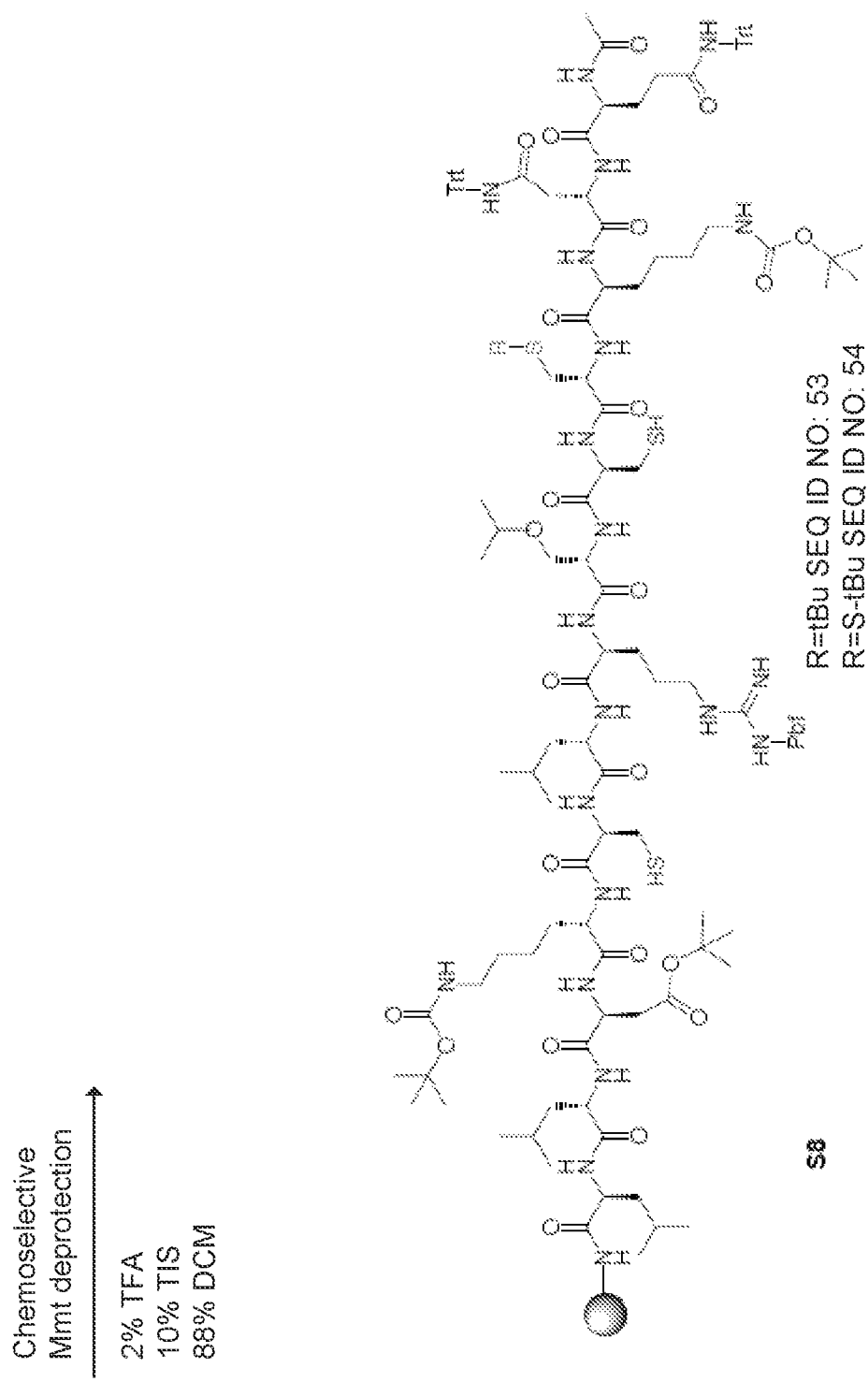
Figure 14C:
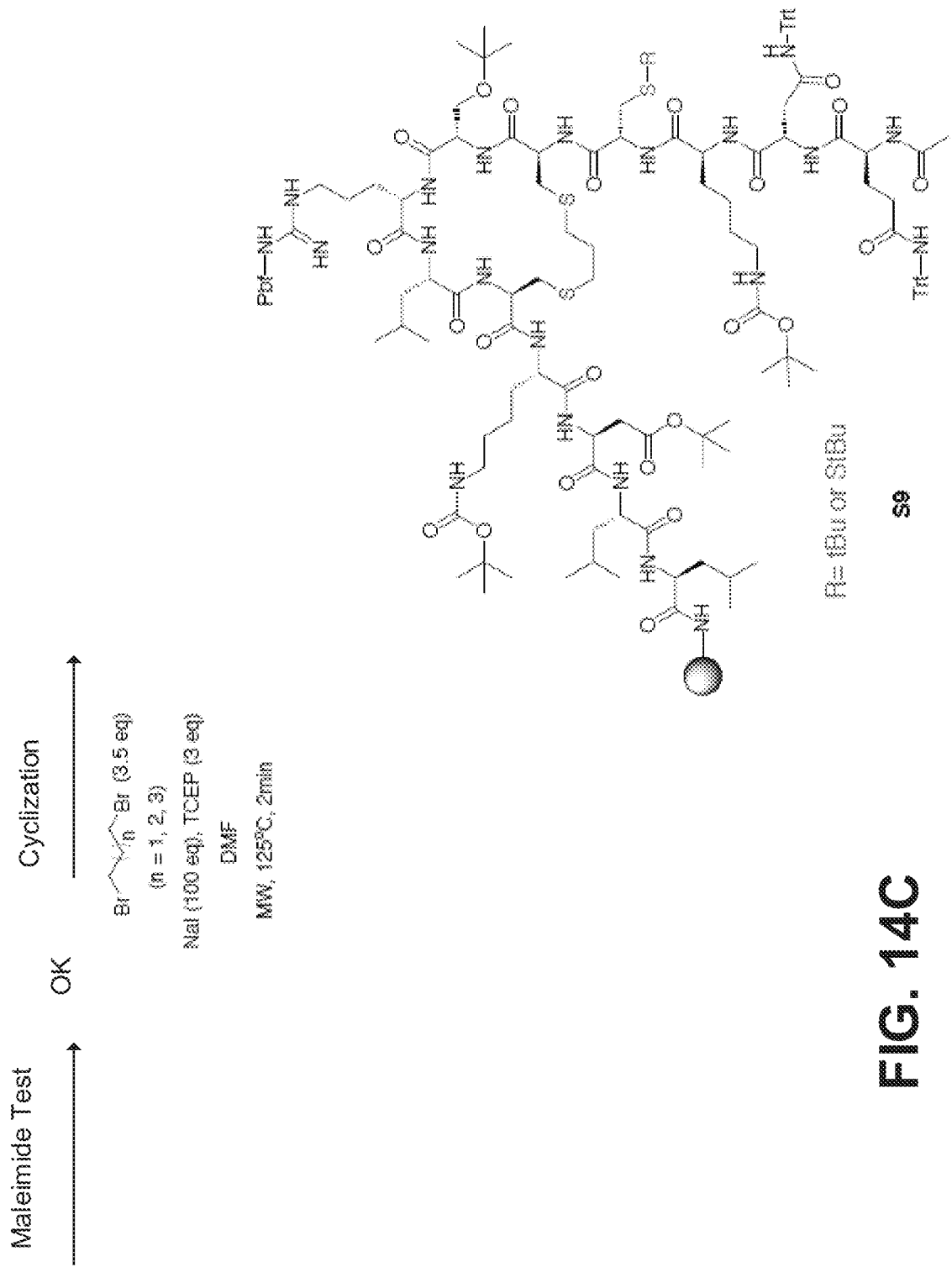
Figure 14D:
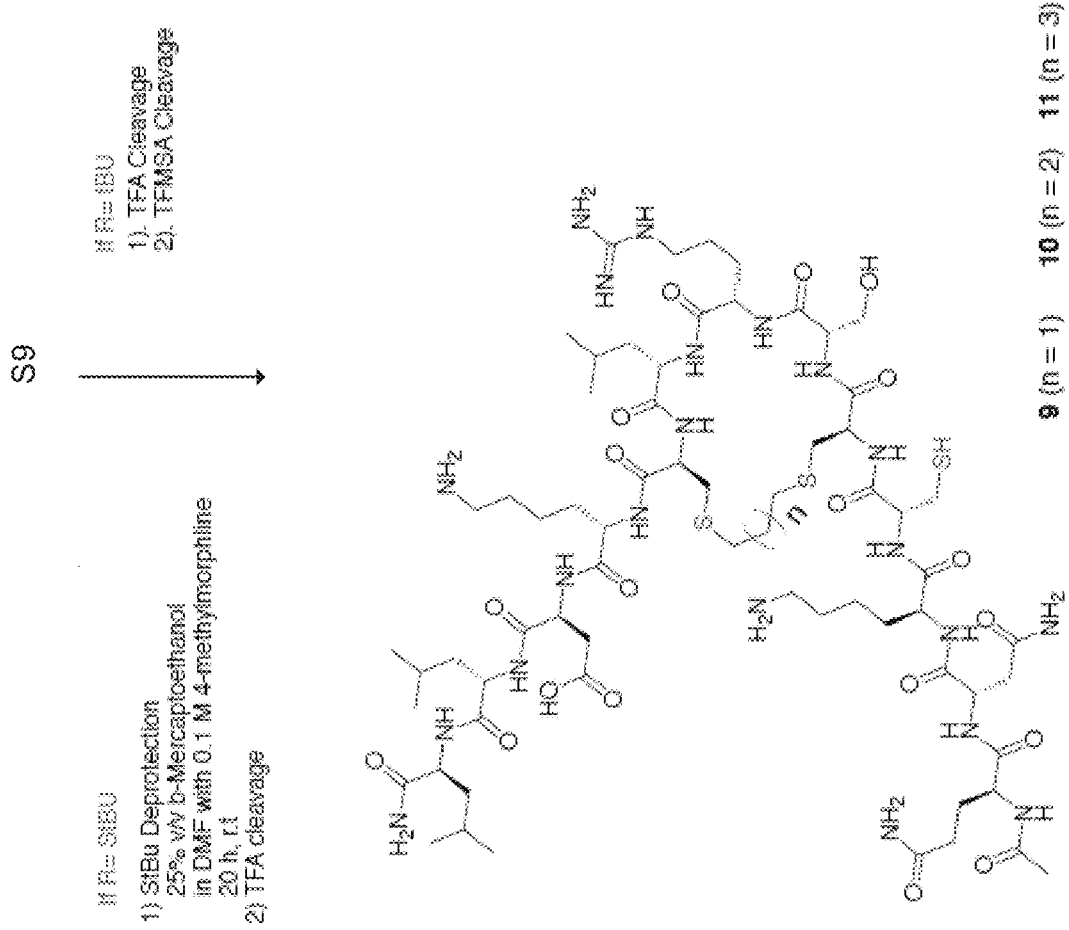
Figure 15A:
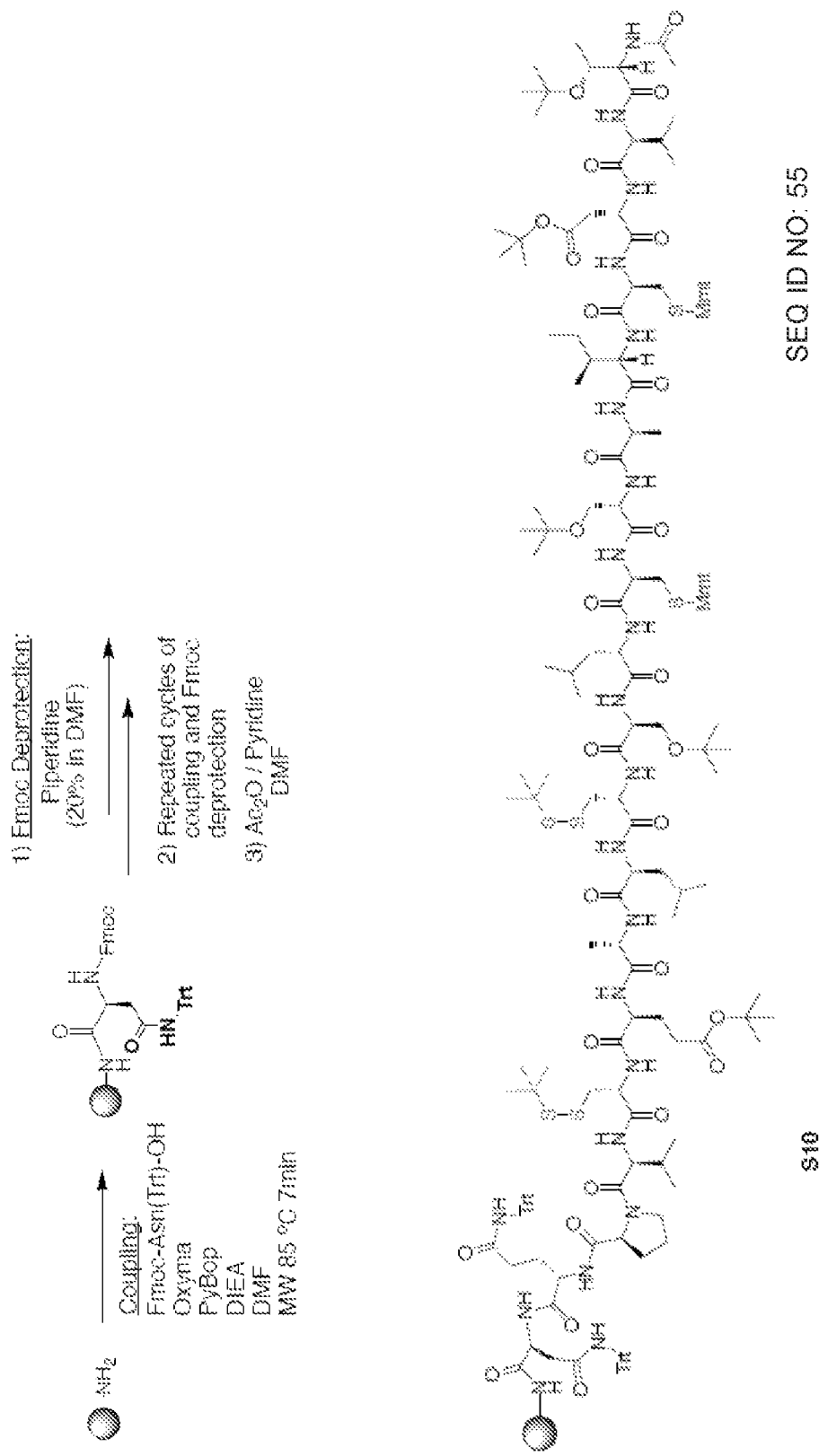
FIG. 15A, FIG. 15B, FIG. 15C, FIG. 15D, FIG. 15E and FIG. 15F depicts a synthetic scheme for the chemoselective preparation of "stitched" peptides or double-turn stapled [2×(i, i+4)].
Figure 15B:
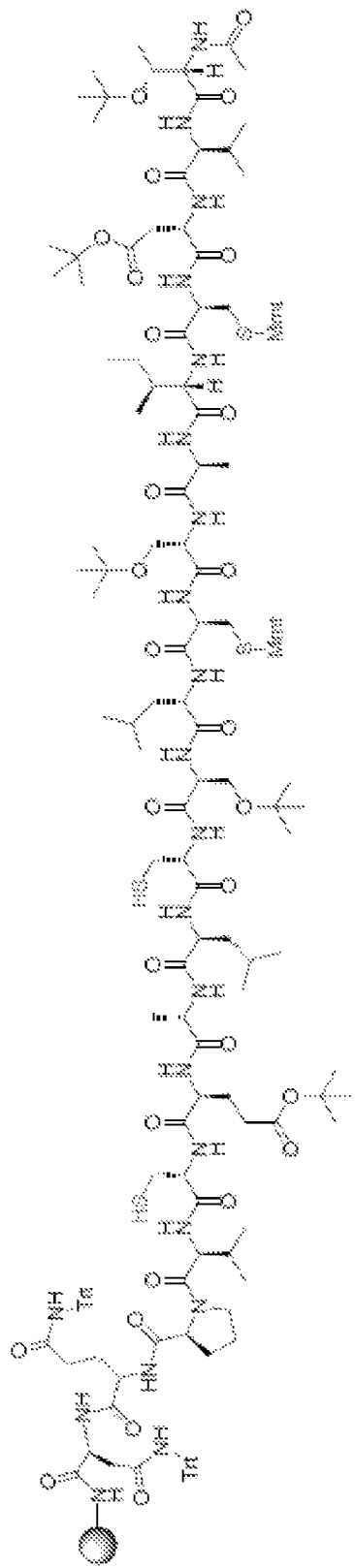
Figure 15C:
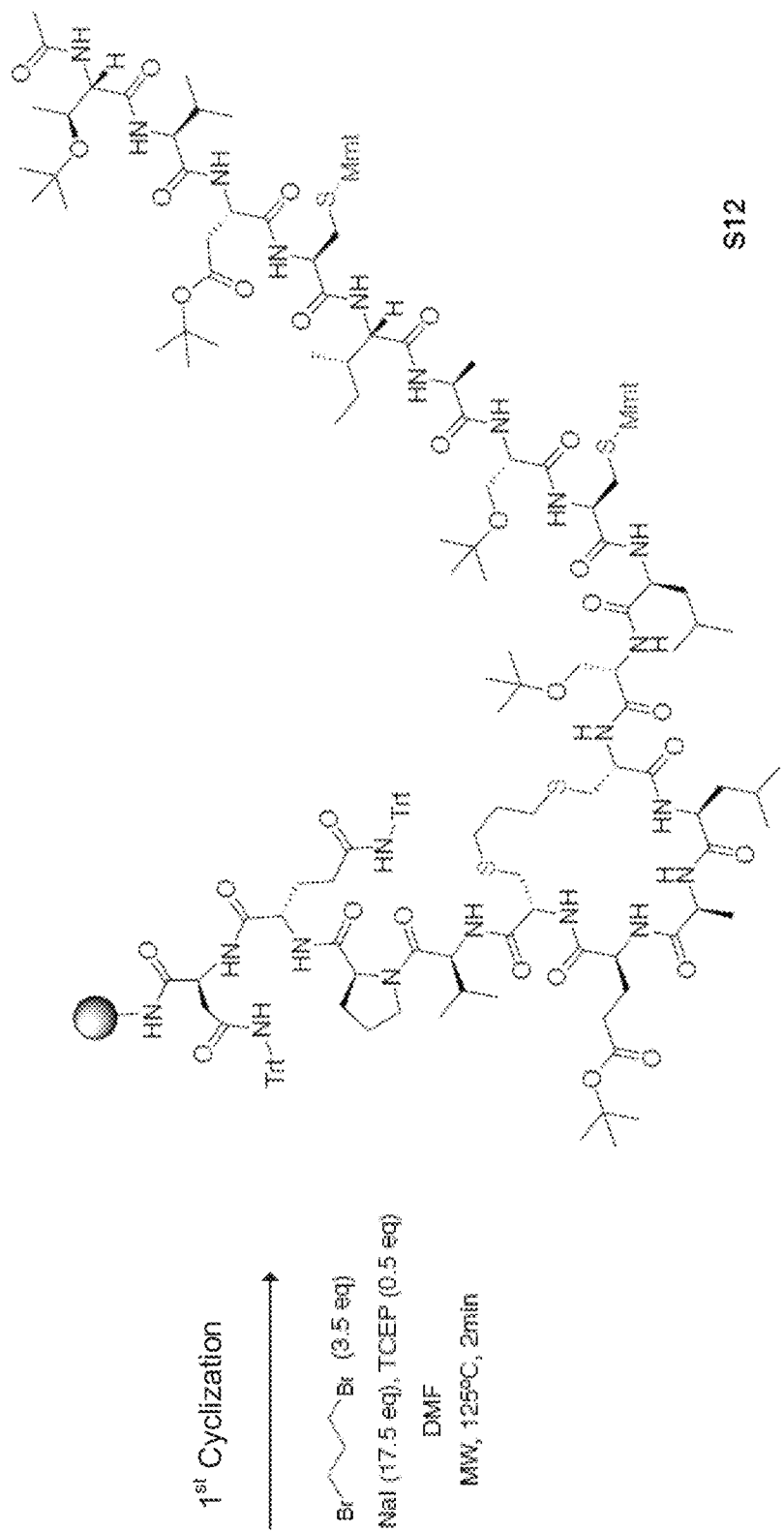
Figure 15D:
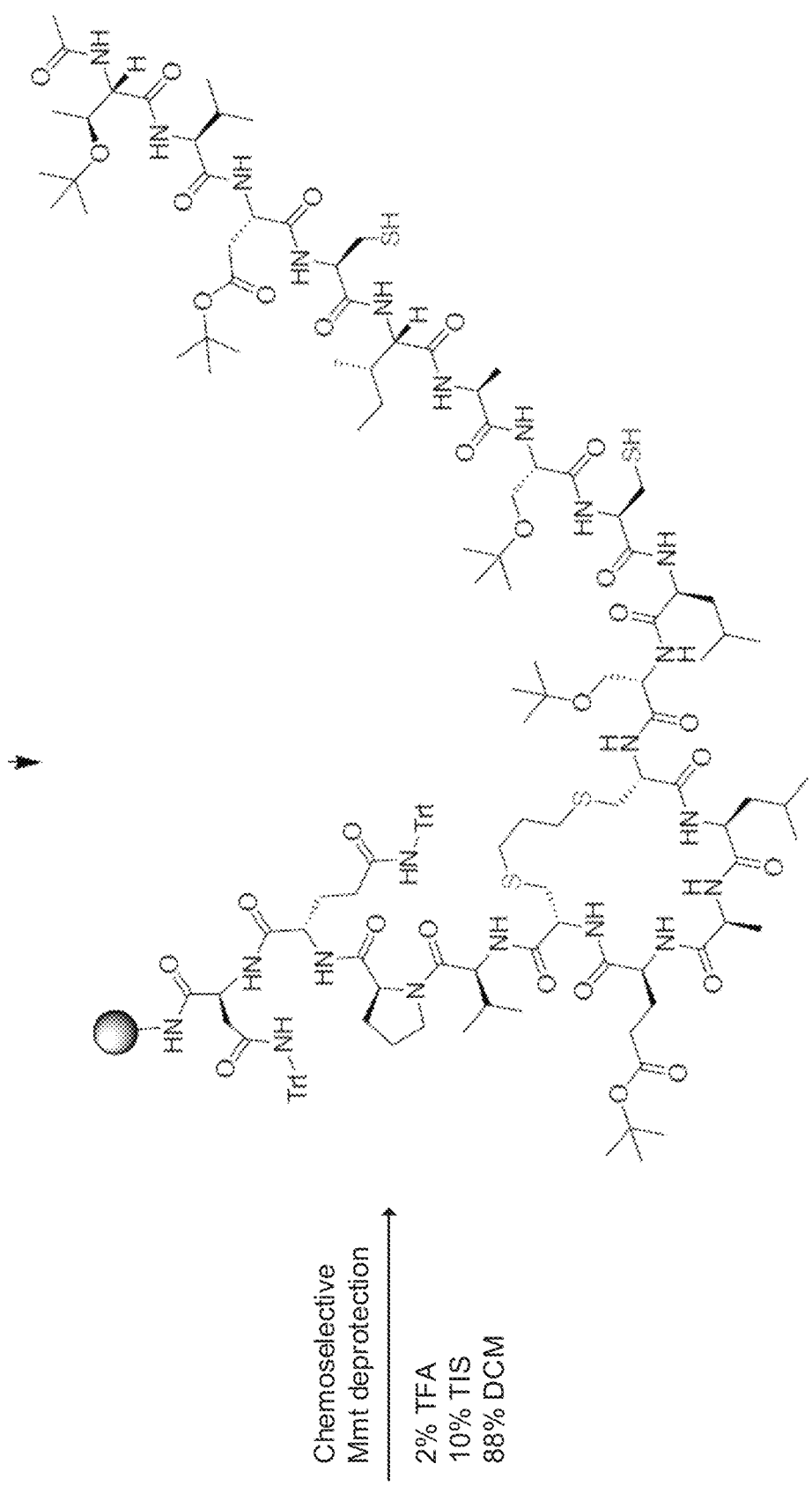
Figure 15E:
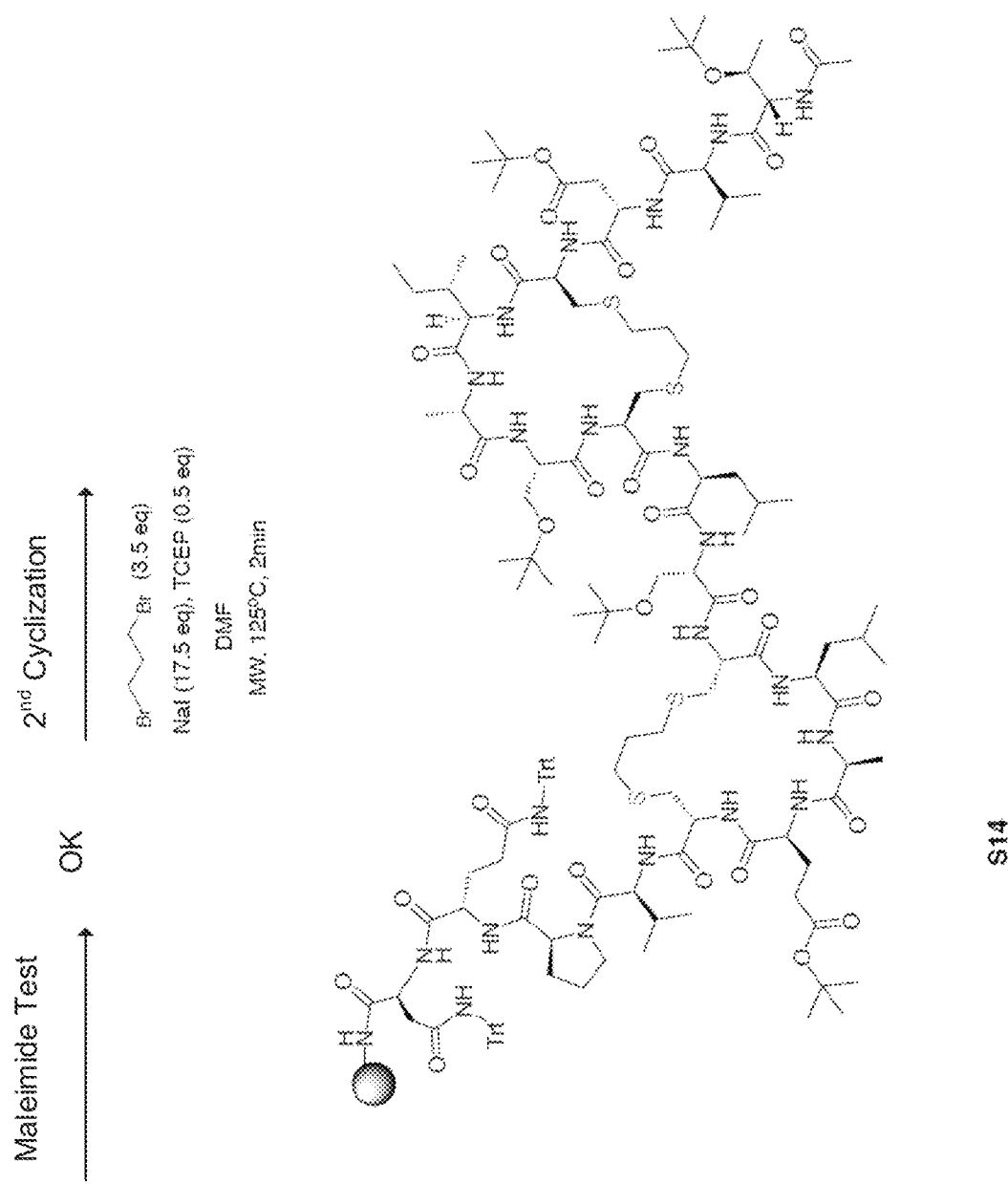
Figure 15F:
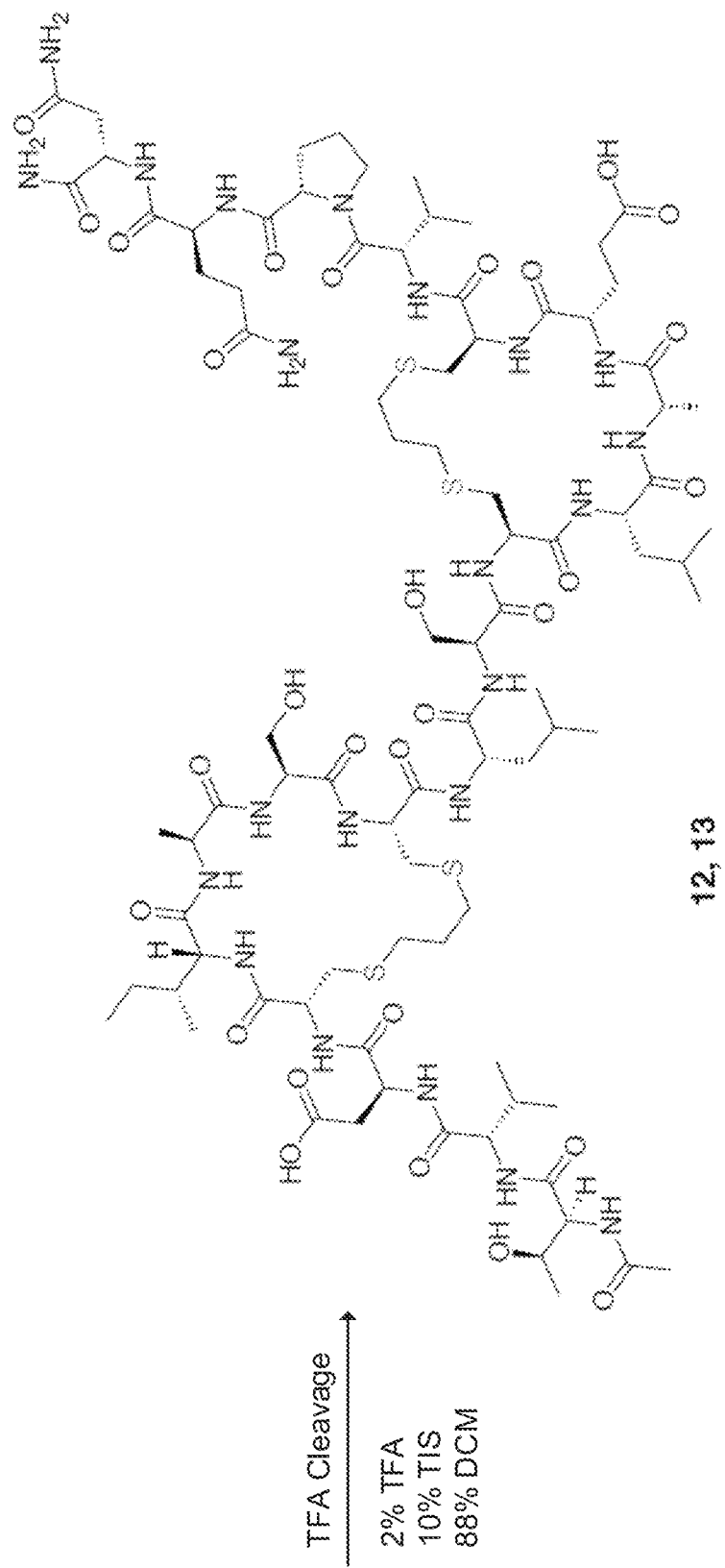

The favorable physicochemical profile of 24 (GN-Z24) motivated a study of its ability to target and functionally block PRC2-mediated H3K27me3 in Caki-1 cells. Treatment with varying concentrations of 24 (GN-Z24) for 72h, followed by western blot analysis of the extracted histone proteins, showed a clear dose-response inhibition of H3K27me3 (FIG. 10A). Further quantitation of H3K27me3 by an absorbance-based colorimetric assay yielded an $IC_{50}$ of 1.36±1.14 µM, similar to that obtained in the enzymatic assay (FIG. 10B). The selectivity of compound 24 (GN-Z24) for PRC2 methyltransferase activity was tested by monitoring its effect on several others post-translational modifications. The stapled peptide showed exquisite selectivity for H3K27Me3 inhibition. Thus, treatment of caki-1 cells with either high concentration of 24 (GN-Z24, 5 µM) or vehicle, and subsequent western blot analysis of histones isolated from the cell lysate, indicated no effect on H3K4me3, H3K9me3, H3K36me2, H3K79me2 and H3K27Ac. On the other hand, total inhibition of H3K27me3 was observed in the same experimental conditions (FIG. 10C). Altogether, this data demonstrates that the stapled peptide 24 (GN-Z24) is resistant to proteolysis, cell permeable and a potent selective inhibitor of the relevant physiological methylation substrate of PRC2.

Methods

Solid Phase Peptide Synthesis. All peptides were manually synthesized on 4-alkoxy-2,6-dimethoxybenzyl-amine resin (PAL, 0.5 mmol/g). Coupling steps were performed under Microwave irradiation, using a combination of PyBOP/Oxyme as coupling reagents. Fmoc deprotection was accomplished at room temperature with a piperidine solution, 20% in DMF.

4-methoxytrityl (Mmt) Deprotection and Maleimide test. Mmt deprotection was carried out with a deprotection solution (15 mL per 0.5 g of resin, 2% TFA, 10% TIS, 88% DCM) at room temperature for 5 min. The resin was then washed with DCM (5×) and treated repeatedly with the same solution until its color changed from orange to light yellow. Maleimide test was next performed. To this end, a small aliquot of Mmt deprotected resin was neutralized with 3 mL of 5% DIEA in DMF for 5 min, and washed with DMF (2 mL, 3×), DCM (3 mL, 3×) and DMF (3 mL, 2×). The neutralized clean resin 14 was subsequently mixed with N-methylmaleimide (5 eq. from a 20 mg/mL DMF stock solution), and DIEA (5 eq.) in a 2-mL microwave vial with a stir-bar, and reacted under microwave irradiation at 85° C. for 15 min. Next, the suspension was transferred into a SPPS vessel, washed (DMF 2 mL 3×, DCM 2 mL 3×) and treated with the proper cleavage cocktail. The resulting peptide is finally precipitated/washed with cold diethyl ether and analyzed by LC/MS to quantitate the extent of the deprotection step (Scheme S4). If the Mmt-deprotection is incomplete, additional deprotection rounds are repeated until completion of the reaction. After total Mmt removal is achieved, the resin is neutralized with 5% DIEA in DMF for 5 min, washed with DMF (3×) and DCM (3×), and dried under vacuum for storage or used directly for the cyclization step.

Stapling Reaction. The resin containing the precursor Cys-thiol free linear peptide was transferred into a microwave reaction vial containing a stir-bar, to which NaI (100 eq for i+7 sequences, 17.5 eq for i+4 sequences) and DMF (1 mL per 20 mg of resin for i+7 sequences, 1 mL per 10 mg of resin for i+4 sequences) were added subsequently, while keeping the mixture stirring at all times, followed by TCEP (3 eq for i+7 sequences, 0.5 eq for i+4 sequences, from an aqueous stock solution of 300 mg/mL). The vial was then capped with a MW vial cap equipped with a rubber septum and the resulting suspension bubbled under N2 for 15 min. Next, DIEA (35 eq.) was added (by syringe), keeping the stirring under N2 for another 30 min, after which, the dibromoalkyl electrophile was injected (20 eq for i+7 sequences, 3.5 eq for i+4 sequences). The suspension is finally reacted under microwave irradiation for 2 min at 125° C., transferred into the SPPS reaction vessel and washed with water (5×, soak if necessary to remove residual NaI), DMF (5×) and DCM (5×). The efficiency of the stapling step was confirmed by cleaving a small aliquot of resin and analyzing the precipitated/washed peptide pellet by LC/MS and HPLC.

Circular Dichroism (CD)

Circular dichroism spectra were recorded on a CHIRASCAN™ spectrometer. Peptides were dissolved in deionized water, at a concentration of 25 μM. CD signal was monitored at 1 nm intervals from 180 to 260 nm with a 1-mm path quartz cuvette. The data reported is the average of three scans, subtracting the background. The helical content of each peptide was determined using prism 7 software, with molar ellipticity $[\theta][deg \cdot cm^2 dmol^{-1}]$ being calculated using the following formula: $[\theta]=1000000\times\theta/(C\times\#of\ residues \times l)$, where θ is the ellipticity read out from Chirascan, C is the concentration of peptide samples in μM, l is the pathlength of the cuvette measured in mm. The percentage helicity was calculated with formula:% Hellicity=$100\times[\theta]_{222}/[\theta]_{max222}$, where $[\theta]_{max222}=-31500\times[1-(-2.5\times\#of\ residues)]$.

Chymotrypsin Stability Test

Assays were performed using freshly prepared α-chymotrypsin from bovine pancreas type II, ≥40 U/mg. The enzyme was initially reconstituted in HCl 1M (1 μg/μL), and kept in ice until used. Peptides stock solutions were prepared in assay buffer (50 mM Tris.HCl pH=8.0, 560 μM calcium chloride, 0.1% Tween-20) containing <3% of DMSO. The reactions were performed at a 200 μL scale, in assay buffer, at final concentrations of 50 μM for peptide and 60 μM for α-chymotrypsin (10 μL from the reconstitution solution). The mixture was incubated at 37° C. and aliquots were withdrawn in portions of 25 μL at different time points for analysis. The removed aliquots were mixed with 25 μL of water 1% TFA, and then treated with a column for detergent removal following the manufacturer's protocol (Pierce, Catalog #:87776). The rate of peptide proteolysis was monitored by HPLC and HPLC-MS analysis. Control experiments were carried out under the same conditions but using BSA instead of α-chymotrypsin.

Plasma Stability Test 1 mM stock solution of the corresponded peptide was prepared in PBS buffer (pH 7.4). Next, 50 μL from 28 this solution were added to 1 mL of human plasma (Sigma-Aldrich, P9523). The mixture was incubated at 37° C. with mechanical shaking at 300 rpm. Aliquots were withdrawn in portions of 150 μL at different time points for analysis and mixed with 60 μL ACN/EtOH (1:1 v/v) for plasma protein precipitation. After centrifugation at 12000 rpm for 5 min, the supernatant was collected and analyzed by HPLC and HPLC-MS.

Enzymatic Functional Assay to Quantify Inhibition of H3K27me3.

All peptide candidates were evaluated for their ability to inhibit H3K27 trimehtylation in vitro with an EpiQuik Histone Methyltransferase Activity/Inhibition Assay Kit (H3K27) (Epigentek, P-3005). The enzymatic reactions were performed using PRC2 complex extracted as a component of the nuclear extracts from a human clear cell renal carcinoma cell line (Caki-1). Protein concentration in the nuclear extracts was first optimized in order to have the suitable concentration of functional PRC2 to produce a strong signal (Control, A=0.9) with a reliable assay window (Blank, A=0.15). The assays were validated by using GSK-126, a well-characterized Ezh2 inhibitor, as a positive control. The trimethylation reaction was performed in vitro using immobilized recombinant oligonucleosomes and then quantified by absorbance, following the manufacturer's protocol. Experiments were carried out using several concentrations of inhibitors, always including a 100% inhibition control of 0.1 μM GSK126. The data were fit into a standard Langmuir isotherm for inhibition and are the result of the average and standard deviation of three independent experiments.

Cell Culture

Metastatic human clear cell renal carcinoma cell line (Caki-1) were used to extract the active PRC2 complex used in the enzymatic assays. Caki-1 cells and healthy control lung fibroblast cell (IMR90) cell lines were used to study the cytotoxic activity of compounds 9, 10, GSK126 and 24. The cells were all obtained from the American Type Culture Collection (ATCC) (Manassas, Va.). All of the cells were grown adherently. The Caki-1 cells were cultured in Roswell Park Memorial Institute (RPMI-1640) (Mediatech Inc., Manassas, Va.) medium, while IMR90 cells were maintained in Dulbecco's modified Eagle's medium (DMEM) (Mediatech Inc., Manassas, Va.); all media were supplemented with 10% foetal bovine serum (FBS, Life Technologies, Grand Island, N.Y.), 1% Minimum Essential Media (MEM) nonessential amino acids (Mediatech), and 1% penicillin-streptomycin (Mediatech). All cells were cultured at 37° C. under 5% $CO_2$ and 95% air in a humidified incubator.

Nuclear Extraction

Active PRC2 was isolated as a component of the nuclear extracts from Caki-1 cells, using EpiQuik Nuclear Extraction kit (Epigentek OP-0002-1) and following the manufacturer's protocol.

Inhibition of H3K27me3 in Caki-1 Cells

The ability of the cyclopeptides to inhibit H3K27me3 in cells was studied by treating Caki-1 cells with different concentrations of the corresponding stapled peptide containing a maximum DMSO concentration of 1%. The cells were treated for 72h, fresh cyclopeptide solution was provided every 24h. Wild type linear peptides (100 μM and 25 μM), GSK126 (1 μM) and media containing 1% DMSO were used as controls. After treatment, the cells were lysed and the histone extracted using the EpiQuik Total Histone Extraction Kit (Epigentek OP-0006-100), following the instructions provided by the manufacturer. Total H3 concentrations were then measured for all the extracted samples using the EpiQuik Total Histone H3 Quantification Kit (Colorimetric, P-3062). Finally, trimethylation levels were evaluated by Western blot. To this end, 10 ng of each histone extract lysate were added on a 12% Mini-PROTEAN® TGX™ Precast Gels (Biorad). Electrophoresis was then carried out with Mini-PROTEAN® Tetra Vertical Electrophoresis Cell (Biorad) at 200 V for 30 min. Next, protein bands were transferred onto Nitrocellulose Membrane (Biorad, 0.2 μm) with Trans-blot SD Cell (Biorad) at 150 mA for 45 min. Downstream process of the membrane included blocking (50% Li-COR Odyssey® Blocking Buffer PBS, 60 min at RT on orbital shaker), incubation with primary antibody (Cell Signaling: Trimethyl-H3K27 Rabbit mAb #9733, and Histone H3 mouse mAb #3638, overnight at 4° C.), washing with PBST buffer, and incubation with secondary antibody (IRDye® 800CW Donkey anti-Mouse IgG, and IRDye® 800CW Donkey anti-Rabbit IgG) at RT for 60 min on an orbital shaker. Blotting imagines were obtained with Odyssey® FC Imaging System (700 nm channel for H3K27me3 and 800 nm channel for H3).

Alternatively, the levels of H3K27me3 in the extracted histones were quantified using the EpiQuick Global Trimethyl Histone H3K27 Quantification Kit (Colorimetric, Epigentek P-3042). The calculated values were normalized to the previously determined values for the corresponding total H3. The data were fit into a standard Langmuir isotherm for inhibition and are the result of the average and standard deviation of three independent experiments.

Confocal Microscopy

Caki-1 cells ($0.8 \times 10^5$ cells/well) were cultured for 24h on Millicell EZ SLIDE (Milliporesigma, PEZGS0416) in 1 mL complete RPMI supplemented with 10% FBS and 2 mM L-glutamine, 1% Minimum Essential Media (MEM) nonessential amino acids (Mediatech), and 1% penicillin-streptomycin (Mediatech). The cells were then seeded, on fresh medium, with fluorescent peptide (final concentration 5 μM, 1% DMSO) or vehicle (1% DMSO) and incubated for 5h at 37° C. under 5% $CO_2$ and 95% air in a humidified incubator. Next, the medium was removed, and each well washed with 1 mL PBS (3×, 5 min each time), followed by fixation with 4% paraformaldehyde in PBS (500 μL, Alfa Aesar), at room temperature for 15 min. After removal of the fixation solution, the slides were washed with PBS (3×, 5 min each time) and the nucleus of the cells stained with 250 μL of DAPI solution (1m/mL in PBS, Sigma-Aldrich, 28718-90-3) at room temperature for 10 min. The DAPI solution was next aspirated, the wells were washed with PBS (3×, 5 min each time), and the cellular skeleton was stained with Alexa Fluor 555 Phalloidin following the manufacturer protocol. Subsequently, the slides were washed with PBS (3×, 5 min each time), before adding 20 μL of mounting medium (Prolong Gold, Invitrogen, P10144) into each well, following the manufacturer's protocol. The slides were kept in the dark for 24 hours before imaging. The cells were visualized with an Olympus Fluoview microscope (model number: FV10i).

Antiproliferative assays. Cells were seeded at a concentration of $0.15 \times 10^6$ cells/well in 3 mL of RPMI supplemented with 10% FBS and 2 mM L-glutamine, 1% Minimum Essential Media (MEM) nonessential amino acids (Mediatech), and 1% penicillin-streptomycin (Mediatech) into tissue culture grade 6-well flat bottom plates (Fisher Scientific, Waltham, Mass.) and grown for 24 h at 37° C. under 5% $CO_2$ and 95% air in a humidified incubator. Following seeding, the cyclopeptides were dissolved in DMSO and diluted in media before addition to cell culture medium at a maximum DMSO concentration of 1%, at cyclopeptide concentrations ranging from 0.01 μM to 1.5 μM. For the following 72h, every 24 h the cell culture media was changed and fresh media containing the compounds was added, 1% DMSO was used as control. After 72h of treatment, both floating and attached cells were collected and analyzed. NucleoCounter NC-3000™ chamber (Chemometec, Allerod, Denmark) was used to determine total cell number and viability according to the manufacturer's protocol.

Characterization of peptides: Characterization data is provided in U.S. Provisional Patent Application 62/900,964 (filed Sep. 16, 2019), the content of which is hereby incorporated by reference.

Solid-Phase Synthesis

This disclosure also provides an efficient and complementary solid-phase method for the chemoselective ligation of cysteine residues with various aliphatic electrophiles, applicable to the preparation of single-turn, double-turn, and double-stapled macrocycles. The approach allows for ligation with hydrocarbon linkers of various lengths, avoiding the use of unnatural amino acids and expensive catalysts, and affords cyclopeptides with remarkable resistance to proteolytic degradation. In contrast to the currently available cysteine crosslinking methods, such a protocol allows the chemoselective ligation of sequences containing several cysteine residues and to prepare macrocycles containing multiple bisthioether staples.

The first studies were carried out on a 10-mer sequence containing two cysteines at positions i and i+4 (FIG. 11A, FIG. 11B, FIG. 11C, FIG. 11D and FIG. 11E). The peptide was elongated on a low substituted resin to avoid undesired intermolecular crosslinking during the ligation step. To allow selective deprotection on beads, both cysteines were orthogonally protected with 4-methoxytrityl (Mmt). The cyclization was initially attempted at room temperature overnight, using 1,3-dibropropane as electrophile and a mild base (DIEA), in a polar organic solvent (DMF). However, the reaction did not produce the desired cyclic peptide. Instead, a mixture of the unreacted linear precursor and the disulfide-bridged macrocycle were formed (see Table 2, Entry 1 in U.S. Patent Application 62/900,964, the entirety of which is incorporated herein by reference.). Similar results had been reported for the direct bis-alkylation of cysteines residues with all-hydrocarbon dibromoalkyl linkers, except when more reactive alkyldibromides, such as α,α'-dibromo-m-xylene were used.

To push the reaction toward the formation of the stapled peptide, the electrophilicity of the dibromoalkane was increased to prevent the dominating disulfide oxidation. The former was accomplished by using sodium iodide to induce in situ trans halogenation in the more reactive diodoalkane electrophile. To prevent the oxidation of cysteine thiols tris(2-carboxyethyl)phosphine (TCEP), a thiol-free cysteine-reducing agent, was introduced that had been successfully used for such purposes. Other non-nucleophilic organic and inorganic bases were explored as well as microwave activation, by performing combinatorial experiments with variation of one parameter at a time (Table 2 of U.S. Patent Application 62/900,964). The reactions were carried out using 20 mg of peptidyl resin and with 1,3-dibromopropane as electrophile. Based on these battery of experiments, conditions were identified that led to 98% conversion to the desired bisthioether cyclopeptide, in high purity, as determined by both LC/MS and HPLC analysis (Table 2 of U.S. Patent Application 62/900,964, Entry 7J).

The reverse approach, i.e., elongate the peptide first and perform the stapling reaction thereafter, was also studied (FIG. 12A, FIG. 12B, FIG. 12C and FIG. 12D). The sequence was assembled using pseudoproline dipeptides to avoid potential aggregation problems that may have caused the incomplete couplings observed after the cyclization of the 10-mer peptide. Subsequent Cys-Mmt deprotection and stapling of this substrate, using the previously optimized conditions, afforded the desired bis-thioether stapled peptide in high overall purity as discussed in detail in the following section.

Solid Phase Peptide Synthesis (SPPS) of Single-Turn Stapled Peptides (i, i+4). Single-turn peptide stapling was investigated using dibromoalkyl electrophiles containing three different hydrocarbon chains. The solid phase synthesis of the Cys-mutated linear precursor, which contained three different pseudoproline dipeptides, afforded a highly pure crude material. Next, Cys-Mmt deprotection was carried out, which was accurately quantitated by means of a "maleimide test" described in U.S. Patent Application 62/900,964.

Cyclization with both 1,4-dibromobutane and 1,5-dibromopentane 1 also led to the correspondent bisthioether macrocycles, bearing all-hydrocarbon linkers with four and five methylene groups, respectively (Table 2 in U.S. Patent Application 62/900,964, Entries IV-V). Interestingly, HRMS analysis of the reaction crudes also showed a significant amount of a side product of smaller molecular mass in both reactions. The structure of this compound was assigned to a bis dehydroalanine substituted peptide. Conversion of cysteine to dehydroalanine (Dha), by means of a bis-alkylation-elimination mechanism, has been reported to be particularly effective when 1,4-diodo or 1,4-dibromobutane are used as electrophiles. This is likely due to the stability of the cyclic S-bialkylated sulfonium intermediate needed for the elimination step. To avoid this unwanted transformation, trans-1,4-dibromo-2-butene was used as electrophile, since this rigid substrate would not form the key cyclic sulfonium intermediate. As expected, this reaction only afforded the desired bis-thioether stapled peptide, thus confirming the previous structural assignment (Table 2 in U.S. Patent Application 62/900,964, Entry VI, FIG. 2e).

SPPS of Double-Turn Stapled Peptides (i, i+7). Double-turn peptide stapling was performed over the same 19-mer peptide, mutated with cysteines at positions 10 and 17, respectively (FIG. 13A, FIG. 13B, FIG. 13C and FIG. 13D). The synthesis of the linear precursor included the use of pseudoproline dipeptides and yielded a highly pure crude material. After quantitative Cys-Mmt deprotection, as determined by the maleimide test, cyclization proceeded using 1,7-dibromoheptane as electrophile under the previously optimized conditions. The reaction afforded the expected macrocycle, but also the linear unreacted substrate and the disulfide oxidized product (Table 2 in U.S. Patent Application 62/900,964, Entry VII). This result was not surprising since macrocyclization to form this larger ring is likely to be more challenging due to an increase in the conformational entropy of both the linear peptide (both thiols are further apart) and the electrophile (longer hydrocarbon chain). A second round of optimization was then required to improve the outcome of this stapling reaction. From those studies, carried out using 1,7-dibromoheptane as electrophile, it was believed that increasing the number of equivalents of both the electrophile and TCEP results in a 99% conversion to the desired cyclopeptide (Table 2 in U.S. Patent Application 62/900,964, Entry VIII). The same conditions allowed the successful preparation of (i, i+7) stapled peptides bearing all-hydrocarbon linkers with six and eight methylene groups (Table 2 in U.S. Patent Application 62/900,964, Entries IX, X).

SPS of Single-Turn Stapled Peptides with Additional Cysteines in the Sequence (i, i+4, +Cys). Next, the approach was extended to the cyclization of peptides containing additional cysteine(s) residues in the sequence. The chemoselective ligation of such peptides requires orthogonal protection of the extra thiol(s), to avoid undesired crosslinking with the Cys used for ligation. Two orthogonal protecting groups were studied, tert-butylthio (S-tBu) and tert-Butyl (tBu), since they are both compatible with Fmoc and Mmt chemistries and are commercially available. Macrocyclization was carried out on a 13-mer linear precursor containing a total of three cysteines, two Mmt-protected used for stapling, and the third one blocked as either S-tBu or tBu (FIG. 14A, FIG. 14B, FIG. 14C and FIG. 14D). After selective Mmt-deprotection and quantitative cyclization, the reaction conditions were investigated for the removal of both orthogonal protecting groups. Cys-StBu was effectively deprotected using a mild reducing agent in basic conditions. In contrast, Cys-tBu removal was more effective when performed in solution, after the stapled peptide had been cleaved off the resin. Overall, both protocols yielded the correspondent selectively stapled macrocycle in good yields and high purity.

SPS of Stitched Peptides [2×(i, i+4)]. Having optimized the use of orthogonal-cysteine protection in the synthetic method, its feasibility for the chemoselective preparation of "stitched or double-stapled" peptides was explored. These studies were carried out with a different 19-mer sequence, containing two pairs of cysteine orthogonally protected as Cys-StBu and Cys-Mmt (FIG. 15A, FIG. 15B, FIG. 15C, FIG. 15D, FIG. 15E and FIG. 15F).

The total synthesis included (1) Cys-StBu deprotection (2) incorporation of first peptide staple, (3) Cys-Mmt deprotection and (4) incorporation of second peptide staple. Both Cys deprotection steps were monitored by the maleimide test. The tethering steps were monitored by LC/MS, after cleaving an aliquot of the ligated peptidyl resin. The synthetic procedure allowed the chemoselective preparation of two double stapled peptides containing linkers of different lengths, in high overall purities (Table 2 in U.S. Patent Application 62/900,964, Entries XV-XVI).

Methods

Abbreviations

All the abbreviations used for amino acids and peptides follow the rules of the IUPAC-IUB Commission of Biochemical Nomenclature in J. Biol. Chem. 247, 977-983 (1982). In addition, the following abbreviations are used: DMF: N,N-dimethylformamide, DCM: dichloromethane, Fmoc: 9H-fluorenylmethyloxycarbonyl, DIEA: N,N-diisopropylethylamine, PyBOP: (benzotriazol-1-yloxy)tripyrrolidinophosphonium hexafluorophosphate, TFA: trifluoroacetic acid, Oxyma: Ethyl cyano(hydroxyimino)acetate, NaI: Sodium Iodide, TCEP: Tris(2-carboxyethyl)phosphine hydrochloride, Boc: tert-Butyloxycarbonyl, Trt: trityl, Pbf: 2,2,4,6,7-pentamethyldihydrobenzofuran-5-sulfonyl, Mmt: 4-methoxytrityl, EDT: 1,2-ethanedithiol, Et$_2$O:diethyl ether, TFMSA: triflic acid, trifluoromethanesulfonic acid, SPPS: solid phase peptide synthesis, TIS: triisopropylsilane, ACN: acetonitrile, FA: formic Acid, HPLC-MS: high performance liquid chromatography mass spectrometry, HRMS(ESI):

high-resolution mass spectrometry (electrospray ionization), RP-HPLC; reversed phase-high performance liquid chromatography.

General Experimental Information

Microwave reactions were carried out on a Biotage Initiator+ microwave reactor, featured with an infrared temperature sensor, and automatic power adjustment to keep the reaction temperature constant throughout the entire reaction time. The reactions were performed in sodium free glass vials, sealed with a cap equipped with a rubber septum, and under magnetic stirring (stirring rate: 300 rpm). Cooling is performed automatically using compressed air, after the reaction time ends.

Reactions were monitored by both HPLC and HPLC-MS.

HPLC Characterization. HPLC chromatograms were obtained using an Agilent 1200 instrument equipped with a pump, degasser, an autosampler, a diode array detector and automatic collector. Samples were run at four different wavelengths (220 nm, 254 nm, 280 nm and 590 nm), in an Eclipse XDB-C18 5 μm column, using as solvents: Solvent A: $H_2O:CH_3CN:TFA$ (95:5:0.1%); Solvent B: $CH_3CN:H_2O$: TFA (95:5:0.087%), and either of the following methods:

Method 1: Flow rate: 1.0 mL/min., Gradient 10-40% of B in 25 min

Method 2: Flow rate: 1.0 mL/min., Gradient 15-65% of B in 25 min

Method 3: Flow rate: 1.0 mL/min., Gradient 35-85% of B in 25 min

Method 4: Flow rate: 1.0 mL/min., Gradient 10-99% of B in 25 min

HPLC-MS Characterization. Samples were first injected into an RP-HPLC (Agilent 1200) equipped with a pump, degasser, an autosampler and a diode array detector. The flow from the column was directed into the Mass Spectrometer (TOF, Agilent 6220) configured with an electrospray ionization source (ESI), using nitrogen as nebulizer gas. The acquired data was analyzed with Agilent MassHunter qualitative analysis software. Samples were run at four different wavelengths (220 nm, 254 nm, 280 nm and 590 nm), in an Eclipse XDB-C18 5 μm column, using as solvents: Solvent A: $H_2O:CH_3CN:FA$ (95:5:0.1%); Solvent B: $CH_3CN:H_2O$: FA (95:5:0.1%), and the following method: Flow rate: 0.5 mL/min., Gradient 10-99% of B in 10 min.

Calculation of Conversion to Cyclic Peptides and Purity of the Stapling Reactions: % of conversion to the desired macrocycles was calculated by HPLC. Purities were determined by both HPLC and MS (direct injection).

Quantitative Analysis by HPLC:

Reaction crudes were injected into the HPLC, after dilution with H2O:ACN (same ratio as the one used for initial running conditions in the method applied). The threshold of the spectra was set to 5%, using as reference the peak with the highest absorbance at 220 nm. Thus, only peaks with an absorbance above 5% of the highest peak were taken into account for the calculations, in order to avoid errors resulting from minor peaks due to noise or residual peaks remaining in the column from previous injections.

Conversion was calculated according to the following equation:

$$\% \text{ Conversion} = \frac{A_{SP}}{A_{LP}} \times 100$$

where $A_{SP}$ is the area underneath the peak correspondent to the stapled peptide (identified and characterized by MS, after analyzing the collected sample correspondent to that retention time), and $A_{LP}$ the area underneath the peak correspondent to the linear peptide (identified and characterized by MS, after analyzing the collected sample correspondent to that retention time).

The purity of the cyclic peptide in the reaction crude was calculated according to the following equation:

$$\% \text{ Purity} = \frac{A_{SP}}{A_{TP}} \times 100$$

where $A_{TP}$ is the sum of the areas underneath all the peaks above the threshold, excluding the injection peaks within first 2 min of the run, and $A_{SP}$ the area underneath the peak correspondent to the desired stapled peptide (identified and characterized by MS, as previously indicated).

Quantitative Analysis by Mass Spectrometry:

Samples were diluted into $H_2O:ACN$ (1:1) 1% formic acid. Reaction crudes were directly injected into the MS, bypassing the HPLC column, in order to determine accurately the ratio in between the components of the mixture. The threshold of the spectra was set to 5%, using as reference the peak with the highest intensity. Thus, only peaks with an intensity above 5% of the highest peak were taken into account for the calculations, in order to avoid minor peaks due to noise or residual peaks from previous injections.

Purity was calculated according to the following equation:

$$\% \text{ Purity} = \frac{I_{SP}}{I_{TP}} \times 100$$

where $I_{TP}$ is the sum of the intensity of all the peaks above the threshold, excluding reference peaks, and $I_{SP}$ the sum of the intensity values for all the peaks correspondent to the desired stapled peptide (including all the cyclopeptide peaks with different ionization states).

General Procedure for the Synthesis of Bisthioether Stapled Peptides

Peptide Elongation 0.500 g of the resin (PAL resin, BACHEM, f=0.5 mmol/g), were first pre-swelled in DCM (10 mL, 30 min) and then washed with DMF (5 mL, 3×) and DCM (5 mL, 3×). Next, a coupling solution containing the correspondent Fmoc-AA-OH (2.5 eq.), Oxyma (2.5 eq.), PyBop (2.5 eq.) and DIEA (5 eq.) in 10 mL DMF was added to the resin. The suspension was carefully transferred into a 20-mL microwave vial containing a magnetic stir bar, capped, and reacted under microwave irradiation at 85° C. for 7 min. Next, the mixture was transferred back to the solid phase synthesis vessel to be subsequently washed with DMF (5 mL, 3×), DCM (5 mL, 3×), EtOH (5 mL 3×) and DCM (5 mL 3×).

The efficiency of the coupling step was tested by means of the colorimetric Kaiser test. If a positive Kaiser test is obtained, indicative of an incomplete coupling reaction, the resin is treated again with the same coupling solution (freshly prepared) and reacted under the conditions described above. After the coupling is complete, the N-terminus of the peptide is Fmoc-deprotected by treating the resin with 20% Piperidine in DMF, 10 min, twice. Next, the resin is properly washed with DMF (5 mL, 3×) and DCM (5 mL, 3×), and the efficiency of the deprotection tested by the Kaiser test. This iterative process of coupling and deprotection is repeated after the incorporation of each amino acid residue, until the full peptide sequence is elongated. Finally, the N-terminus of the peptide is acetylated (after Fmoc deprotection, following the same conditions previously described), with a solution of acetic anhydride (5 eq.) and pyridine (5 eq.) under microwave irradiation at 85° C. for 5 min. For peptides sequences containing serine and/or threonine, these residues were introduced as pseudoproline dipeptides containing also the corresponding subsequent amino acid in the target peptide sequence. The identity and purity of all the synthesized peptides was assessed by LC/MS and HPLC analysis of the solution of a small peptide sample obtained after cleavage, precipitation and washed with $Et_2O$.

4-methoxytrityl (Mmt) Deprotection and Maleimide test.

Mmt deprotection was carried out with a deprotection solution (15 mL per 0.5 g of resin, 2% TFA, 10% TIS, 88% DCM) at room temperature for 5 min. The resin was then washed with DCM (5×) and treated repeatedly with the same solution until its color changed from orange to light yellow. Maleimide test was next performed. To this end, a small aliquot of Mmt deprotected resin was neutralized with 3 mL of 5% DIEA in DMF for 5 min, and washed with DMF (2 mL, 3×), DCM (3 mL, 3×) and DMF (3 mL, 2×). The neutralized clean resin was subsequently mixed with N-methylmaleimide (5 eq. from a 20 mg/mL DMF stock solution), and DIEA (5 eq.) in a 2-mL microwave vial with a stir-bar, and reacted under microwave irradiation at 85° C. for 15 min. Next, the suspension was transferred into a SPPS vessel, washed (DMF 2 mL 3×, DCM 2 mL 3×) and treated with the proper cleavage cocktail. The resulting peptide is finally precipitated/washed with cold diethyl ether and analyzed by LC/MS to quantitate the extent of the deprotection step. If the Mmt-deprotection is incomplete, additional deprotection rounds are repeated until completion of the reaction. After total Mmt removal is achieved, the resin is neutralized with 5% DIEA in DMF for 5 min, washed with DMF (3×) and DCM (3×), and dried under vacuum for storage or used directly for the cyclization step.

Stapling Reaction.

The resin containing the precursor Cys-thiol free linear peptide was transferred into a microwave reaction vial containing a stir-bar, to which NaI (100 eq for i+7 sequences, 17.5 eq for i+4 sequences) and DMF (1 mL per 20 mg of resin for i+7 sequences, 1 mL per 10 mg of resin for i+4 sequences) were added subsequently, while keeping the mixture stirring at all times, followed by TCEP (3 eq for i+7 sequences, 0.5 eq for i+4 sequences, from an aqueous stock solution of 300 mg/mL). The vial was then capped with a MW vial cap equipped with a rubber septum and the resulting suspension bubbled under $N_2$ for 15 min. Next, DIEA (35 eq.) was added (by syringe), keeping the stirring under $N_2$ for another 30 min, after which, the dibromoalkyl electrophile was injected (20 eq for i+7 sequences, 3.5 eq for i+4 sequences). The suspension is finally reacted under microwave irradiation for 2 min at 125° C., transferred into the SPPS reaction vessel and washed with water (5×, soak if necessary to remove residual NaI), DMF (5×) and DCM (5×). The efficiency of the stapling step was confirmed by cleaving a small aliquot of resin and analyzing the precipitated/washed peptide pellet by LC/MS and HPLC.

Final Cleavage

The peptidyl resin is mixed with the proper TFA cleavage cocktail (TFA/Water/TIS=95/2.5/2.5 for non-cysteine containing peptides and TFA/Water/TIS/EDT=95/2.5/2.5 for cysteine containing sequences). The suspension is then allowed to react on an orbital shaker for 1 h at room temperature or under microwave irradiation at 85° C. for 5 min. Next, TFA is evaporated under a stream of nitrogen and the peptide precipitated with ice cold $Et_2O$. The resulting pellet is finally washed with ice cold $Et_2O$ (5×) and isolated by centrifugation. In a typical experiment, 5 mL cleavage cocktail were used per each 100 mg of resin.

Cleavage Protocol for Sequences Containing St-butyl protected cysteine(s)

StBu deprotection was carried out with a deprotection solution (15 mL per 0.5 g of resin, 25% β-Mercaptoethanol) at room temperature overnight. Maleimide test was next performed to test the efficiency of the reaction. To this end, a small aliquot of Mmt deprotected resin was neutralized with 3 mL of 5% DIEA in DMF for 5 min, and washed with DMF (2 mL, 3×), DCM (3 mL, 3×) and DMF (3 mL, 2×). The neutralized clean resin was subsequently mixed with N-methylmaleimide (5 eq. from a 20 mg/mL DMF stock solution), and DIEA (5 eq.) in a 2-mL microwave vial with a stir-bar, and reacted under microwave irradiation at 85° C. for 15 min. Next, the suspension was transferred into a SPPS vessel, washed 1 (DMF 2 mL 3×, DCM 2 mL 3×) and treated with the proper cleavage cocktail. The resulting peptide is finally precipitated/washed with cold diethyl ether and analyzed by LC/MS to quantitate the extent of the deprotection step. If the deprotection is incomplete, additional deprotection rounds are repeated until completion of the reaction. After total StBu removal is achieved, the resin washed with DMF (3×) and DCM (3×) and dried under vacuum for storage or used directly for the cyclization step.

Cleavage Protocol for Sequences Containing t-Butyl Protected Cysteine(s)

The peptide is cleaved, precipitated and properly washed, following the protocol described above (Final Cleavage Protocol). The resulting dry pellet, still containing t-butyl protected cysteine(s), is then dissolved in a cocktail composed by thiolanisole (4%), EDT (12%) and TFA (84%) (960 μL of cocktail per 100 mg of peptidyl resin). Next, the mixture is cooled down in an ice bath to 5° C., after which, TFMSA (10% v/v of TFA) is added dropwise (avoiding generation of excessive heat). The solution is kept in the ice bath for another 10 min, and then allowed to react at room temperature for 1 hour. Finally, the deprotected peptide is precipitated by adding ice cold $Et_2O$ to the mixture (5× sample volume). To achieve high precipitation yields, the sample may be left at 0° C. for another 30 min. The crude is isolated by centrifugation and subsequently washed with ice cold $Et_2O$ (5×).

Characterization of peptides: Characterization data is provided in U.S. Provisional Patent Application 62/900,964 (filed Sep. 16, 2019), the content of which is hereby incorporated by reference.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A composition of matter with a structure of:
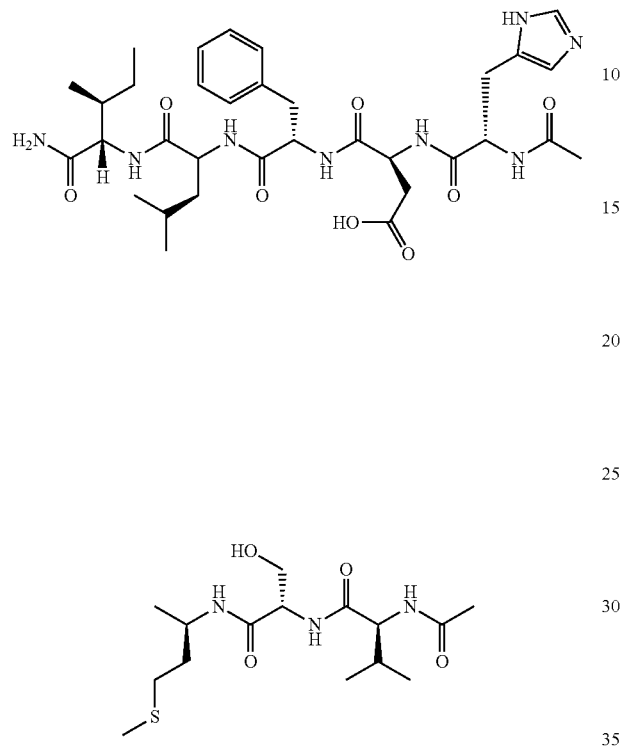
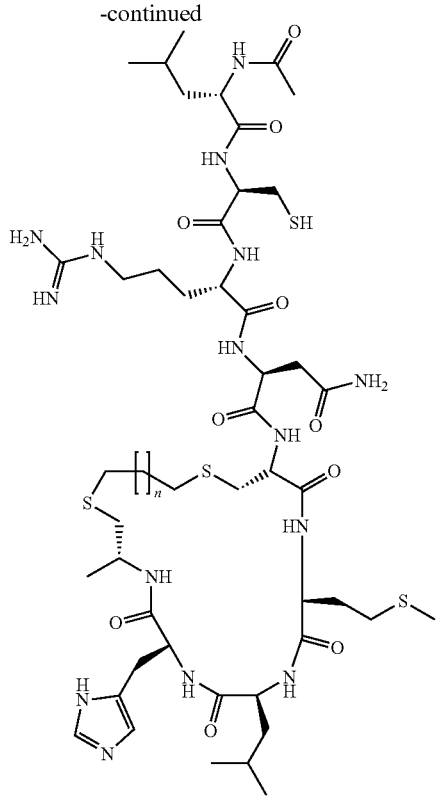
wherein n is 1 or 3.
2. The composition of matter as recited in claim 1, wherein n is 1.
* * * * *